United States Patent
Lee

(10) Patent No.: US 10,327,870 B2
(45) Date of Patent: Jun. 25, 2019

(54) METHOD, DEVICES AND ARTICLES FOR CONDUCTING SUBPERIOSTEAL MINIMALLY INVASIVE AESTHETIC JAW BONE GRAFTING AUGMENTATION

(71) Applicant: Ernesto A. Lee, Bryn Mawr, PA (US)

(72) Inventor: Ernesto A. Lee, Bryn Mawr, PA (US)

(*) Notice: Subject to any disclaimer, the term of this patent is extended or adjusted under 35 U.S.C. 154(b) by 0 days.

(21) Appl. No.: 15/644,387

(22) Filed: Jul. 7, 2017

(65) Prior Publication Data

US 2017/0319298 A1 Nov. 9, 2017

Related U.S. Application Data

(63) Continuation-in-part of application No. PCT/US2017/025478, filed on Mar. 31, 2017.
(Continued)

(51) Int. Cl.
*A61F 2/28* (2006.01)
*A61C 8/02* (2006.01)
(Continued)

(52) U.S. Cl.
CPC ........ *A61C 8/0006* (2013.01); *A61B 17/1673* (2013.01); *A61C 8/0089* (2013.01);
(Continued)

(58) Field of Classification Search
CPC ..... A61F 2002/2835; A61F 2002/2889; A61B 17/1673; A61C 8/0089
See application file for complete search history.

(56) References Cited

U.S. PATENT DOCUMENTS 4,315,745 A 2/1982 Murata
4,340,060 A 7/1982 Berke et al.
(Continued)

FOREIGN PATENT DOCUMENTS

WO WO2014033898 A1 4/2004
WO WO2006010507 2/2006
(Continued)

OTHER PUBLICATIONS

Efraim Kfir, DDS, et al.; "Minimally Invasive Guided Bone Regeneration"; Journal of Oral Implantology, vol. XXXIII, No. Four, 205-210, 2007.*
(Continued)

*Primary Examiner* — Christopher D. Prone
(74) *Attorney, Agent, or Firm* — Bonini IP Law, LLC; Frank J. Bonini, Jr.

(57) ABSTRACT

Methods and devices for subperiosteal minimally invasive aesthetic ridge augmentation and reconstruction, including of the mandible and maxilla. Implementation of procedures that manipulate the tissue to accept an implantable article are carried out. The reconstruction or augmentation involves selecting a surgical site at which an implantable article is to be installed, making one or more incisions in the tissue remote from the selected site, developing a tunnel leading to the site, forming a pouch under the periosteum at the site, and positioning an implantable article, such as a bone graft, in the pouch using the tunnel as the passageway. Implementations may include forming a customized bone graft to address a specific defect, and providing specially configured instruments for use in carrying out the method.

27 Claims, 24 Drawing Sheets

Related U.S. Application Data

(60) Provisional application No. 62/316,140, filed on Mar. 31, 2016.

(51) Int. Cl.

| | | |
|---|---|---|
| *A61C 8/00* | (2006.01) | |
| *A61F 2/00* | (2006.01) | |
| *A61B 17/16* | (2006.01) | |
| *A61B 17/58* | (2006.01) | |
| *A61B 90/00* | (2016.01) | |

(52) U.S. Cl.
CPC .......... *A61F 2/0059* (2013.01); *A61F 2/2803* (2013.01); *A61B 17/58* (2013.01); *A61B 2090/062* (2016.02); *A61F 2002/2835* (2013.01); *A61F 2002/2889* (2013.01)

(56) References Cited

U.S. PATENT DOCUMENTS

| | | | |
|---|---|---|---|
| 4,753,223 | A | 6/1988 | Bremer |
| 4,798,205 | A | 1/1989 | Bonomo et al. |
| 4,820,306 | A | 4/1989 | Gorman et al. |
| 4,911,641 | A | 3/1990 | Detsch |
| 4,968,317 | A | 11/1990 | Tormala |
| 5,372,503 | A | 12/1994 | Elia |
| 5,585,166 | A | 12/1996 | Boniface et al. |
| 5,674,074 | A | 10/1997 | Angelo, Jr. |
| 5,695,338 | A | 12/1997 | Robert |
| 5,885,290 | A | 3/1999 | Guerro |
| 5,899,939 | A | 5/1999 | Boyce et al. |
| 6,033,378 | A | 3/2000 | Lundquist et al. |
| 6,086,592 | A | 7/2000 | Rosenberg et al. |
| 6,102,932 | A | 8/2000 | Kurz |
| 6,273,720 | B1 | 8/2001 | Spalten |
| 6,309,219 | B1 | 10/2001 | Robert |
| 6,478,825 | B1 | 11/2002 | Winterbottom et al. |
| 6,554,803 | B1 | 4/2003 | Ashman |
| 6,575,749 | B1 | 6/2003 | Greenwald |
| D487,151 | S | 2/2004 | Schulter et al. |
| 6,926,699 | B2 | 8/2005 | Stone |
| 6,994,548 | B2 | 2/2006 | Perret, Jr. |
| 7,357,789 | B2 | 4/2008 | Bills |
| 7,662,188 | B2 | 2/2010 | Yamada |
| 7,771,482 | B1 | 8/2010 | Karmon |
| 8,007,278 | B2 | 8/2011 | Chao |
| 8,100,930 | B2 | 1/2012 | Stfanchik |
| 8,202,092 | B2 | 6/2012 | Chao |
| 8,308,727 | B2 | 11/2012 | Hernandez et al. |
| 8,419,737 | B2 | 4/2013 | Yamada |
| 8,486,009 | B2 | 7/2013 | Shih |
| 8,864,841 | B2 | 10/2014 | Karmon |
| 8,968,323 | B2 | 3/2015 | McKay |
| 9,125,624 | B2 | 9/2015 | Dekel et al. |
| D745,241 | S | 12/2015 | Doerr |
| 9,402,691 | B2 | 8/2016 | Merritt et al. |
| 9,744,057 | B2 | 8/2017 | Karmon |
| 2002/0119417 | A1 | 8/2002 | Ashman |
| 2002/0151769 | A1 | 10/2002 | Kim |
| 2003/0104339 | A1* | 6/2003 | Fromovich .......... A61C 8/0033 433/215 |
| 2003/0105469 | A1 | 6/2003 | Karmon |
| 2004/0068234 | A1 | 4/2004 | Martin et al. |
| 2006/0275738 | A1 | 12/2006 | Flanagan |
| 2007/0031788 | A1 | 2/2007 | Chao |
| 2007/0042326 | A1 | 2/2007 | Cardoso |
| 2009/0259227 | A1 | 10/2009 | Ahn |
| 2011/0045438 | A1 | 2/2011 | Alghamdi |
| 2011/0117519 | A1 | 5/2011 | Yamada |
| 2011/0183287 | A1 | 7/2011 | Lee |
| 2012/0330368 | A1 | 12/2012 | Dunn |
| 2014/0234798 | A1 | 8/2014 | Lim |
| 2015/0054195 | A1 | 2/2015 | Greyf |
| 2016/0074127 | A1 | 3/2016 | Merritt et al. |
| 2016/0151117 | A1 | 6/2016 | Gibbs et al. |
| 2016/0228221 | A1 | 8/2016 | Cho |
| 2017/0014209 | A1 | 1/2017 | Jeong |
| 2017/0319298 | A1 | 11/2017 | Lee |

FOREIGN PATENT DOCUMENTS

| | | |
|---|---|---|
| WO | WO2015037838 | 3/2015 |
| WO | WO2016090476 A1 | 6/2016 |

OTHER PUBLICATIONS

Michael S. Block, DMD et al.; Horizontal Ridge Augmentation Using Human Mineralized Particulate Bone: Preliminary Results; American Association of Oral Maxillofacial Surgeons, 2004; J Oral Maxillofac Surg 62:67-72, 2004, Suppl 2.

Oscar Hasson, DDS et al.; "Augmentation of deficient lateral alveolar ridge using the subperiosteal tunneling dissection approach"; Kaplan Medical Center; Oral Surg Oral Med Oral Pathol Oral Radiol Endod 2007, vol. 103, No. 3, e14-e19.

Marc I. Nevins, DMD, MMSc et al.; "Minimally Invasive Alveolar Ridge Augmentation Procedure (Tunneling Technique) Using rhPDGF-BB in Combination with Three Matrices A case Series", The International journal of Periodontics & Restorative Dentistry, vol. 29, No. 4, 370-385, 2009, Quintessence Publishing Co. Inc.

Feng Xuan, MD, et al.; "Vertical Ridge Augmentation Using Xenogenous Bone Blocks: A Comparison Between the Flap and Tunneling Procedures"; 2014 American Association of Oral and Maxillofacial Surgeons; J Oral Maxillofac Surg 72:1660-1670, 2014.

Carlo Mazzocco, MD, DDS, et al.; "The Tunnel Technique: A Different Approach to Block Grafting Procedures"; The International Journal of Periodontics & Restorative Dentistry; vol. 28, pp. 44-53, No. 1, 2008; Quintessence Publishing Co, Inc., © 2008.

Ernesto A. Lee, DMD, et al.; "Lingualized Flapless Implant Placement into Fresh Extraction Sockets Preserves Buccal Aveolar Bone: A Cone Beam Computed Tomography Study"; The International Journal of Periodontics & Restorative Dentistry; vol. 34, pp. 60-68, No. 1, 2014; Quintessence Publishing Co, Inc. © 2014.

Yifen, Li, et al.; "Minimally traumatic alveolar ridge augmentation with a tunnel injectable thermos-sensitive alginate scaffold"; Journal of Applied Oral Science; vol. 23(2), Mar.-Apr. 2015; 23(2): 215-223.

* cited by examiner

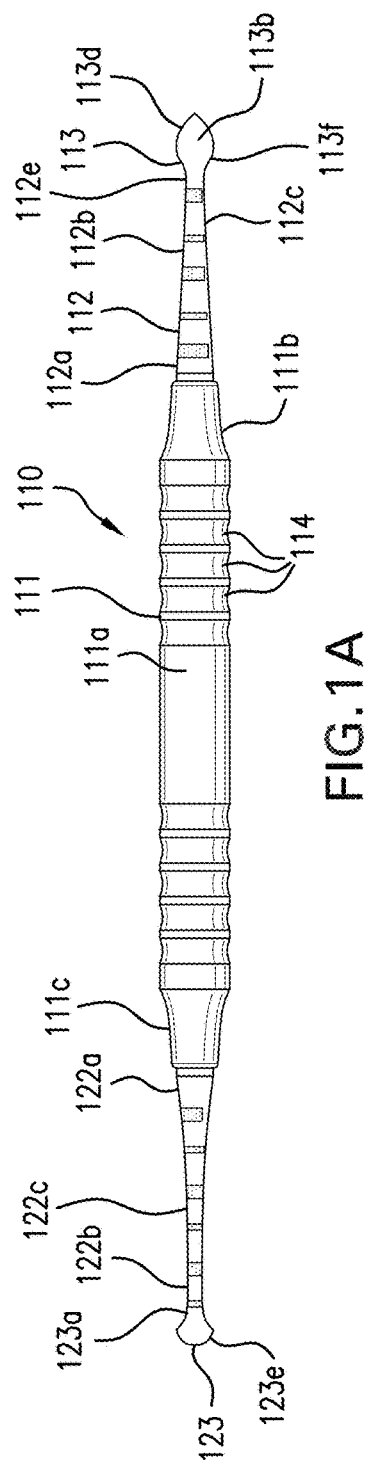
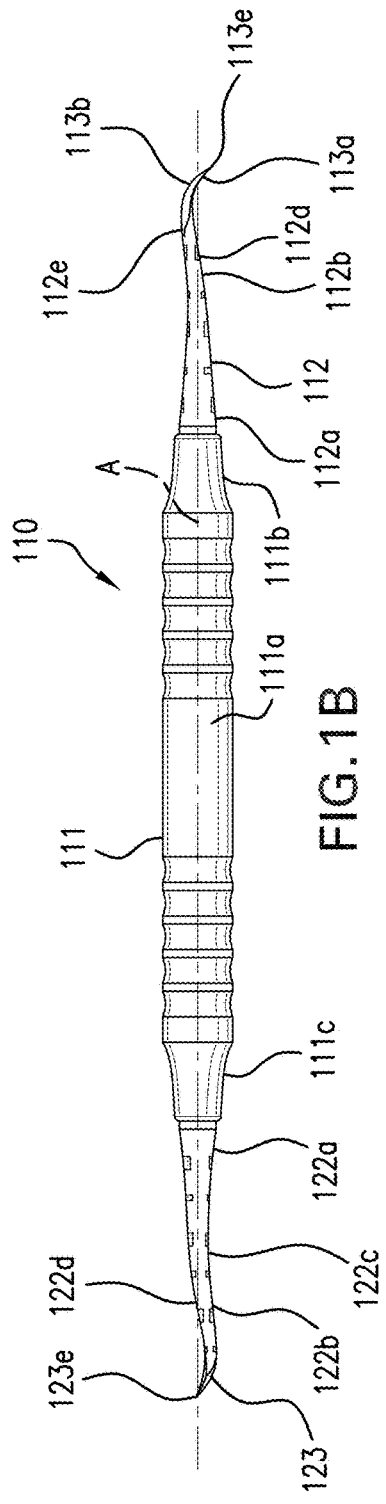
FIG. 1A
FIG. 1B

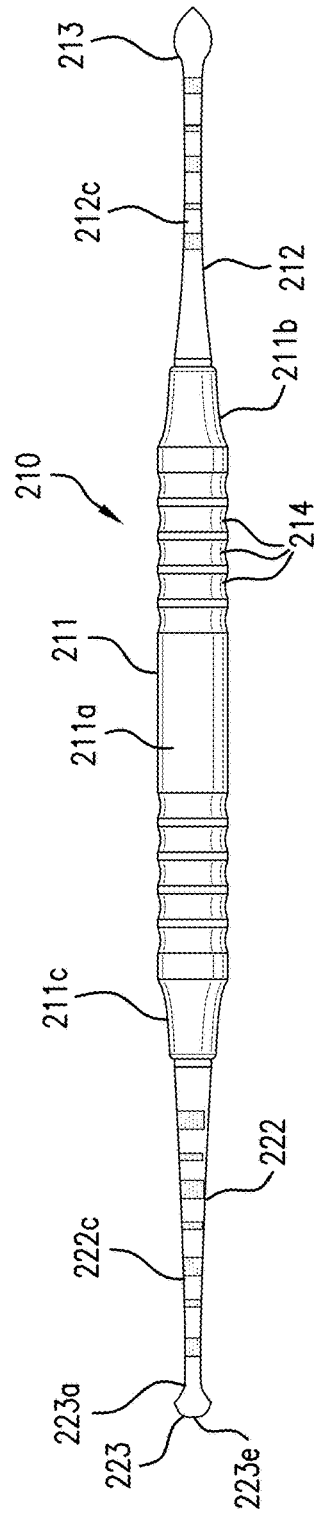
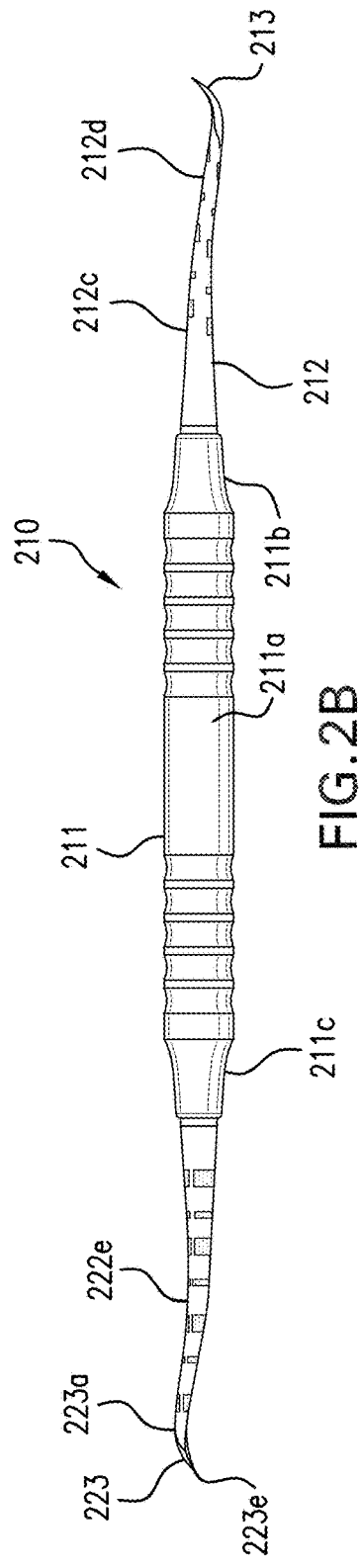
FIG. 2A
FIG. 2B

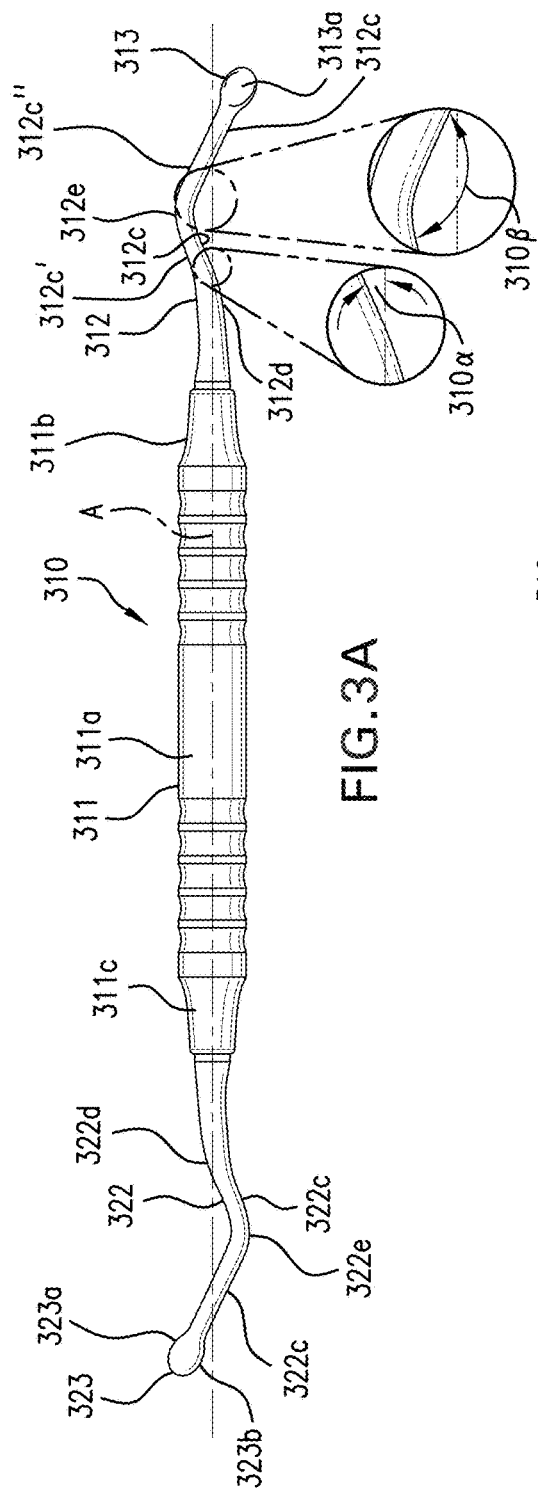
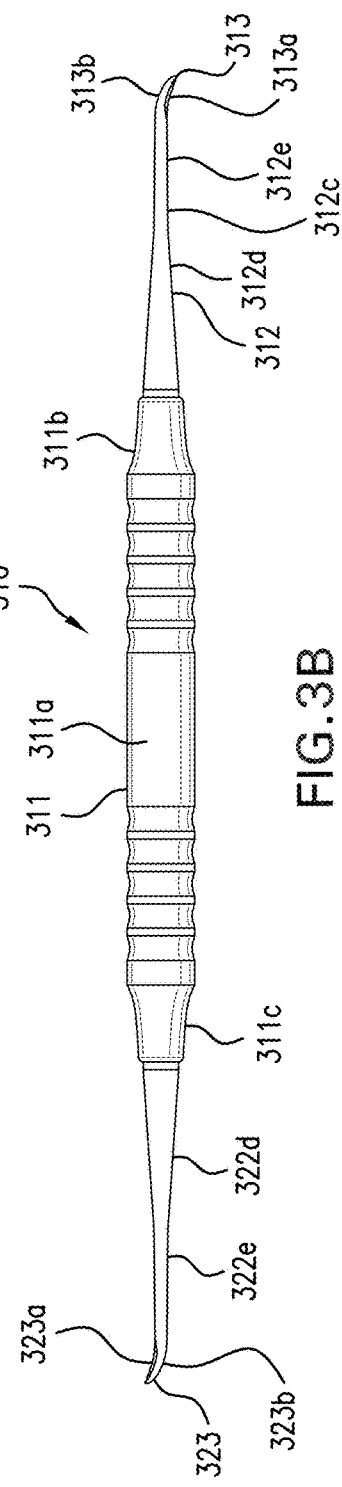
FIG. 3A
FIG. 3B

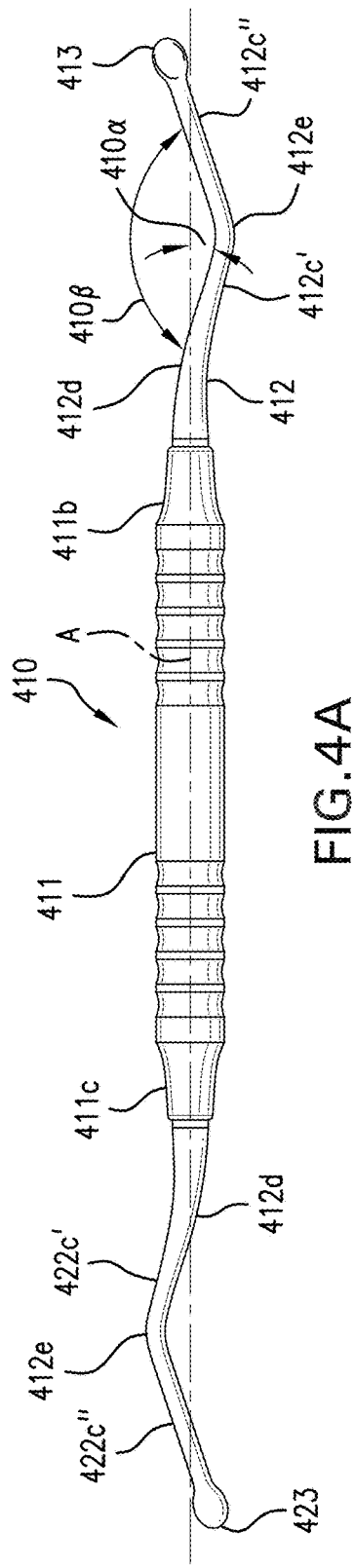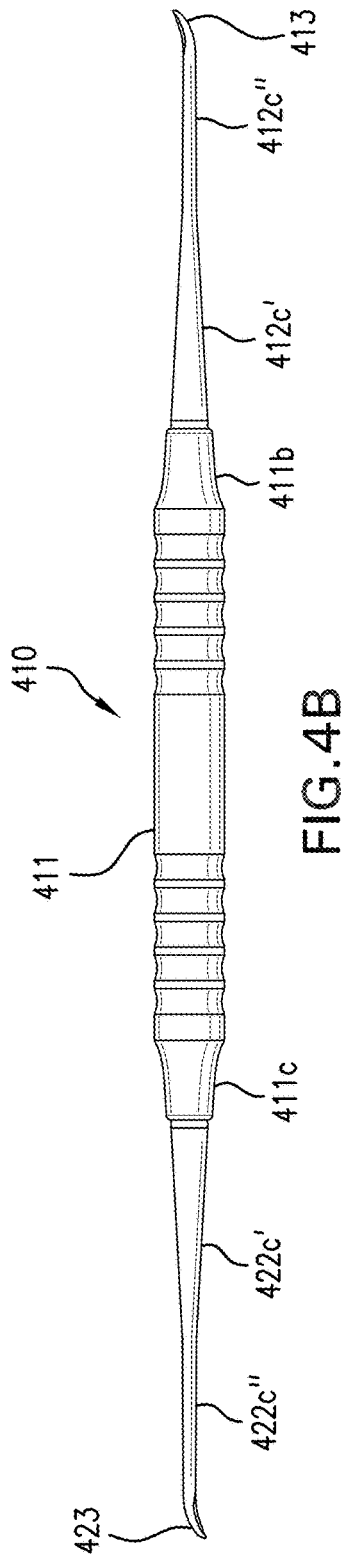
FIG.4A
FIG.4B

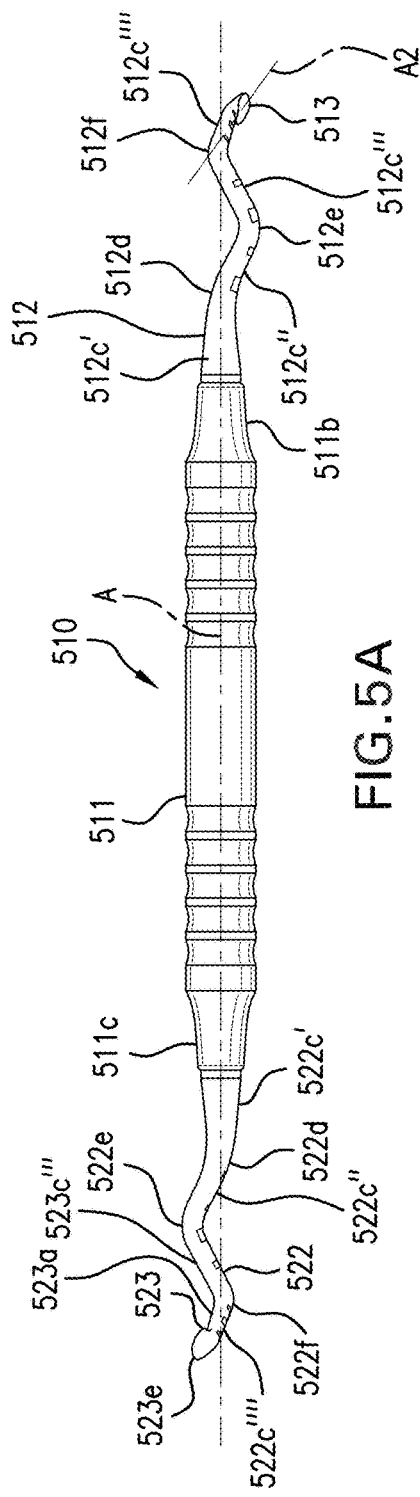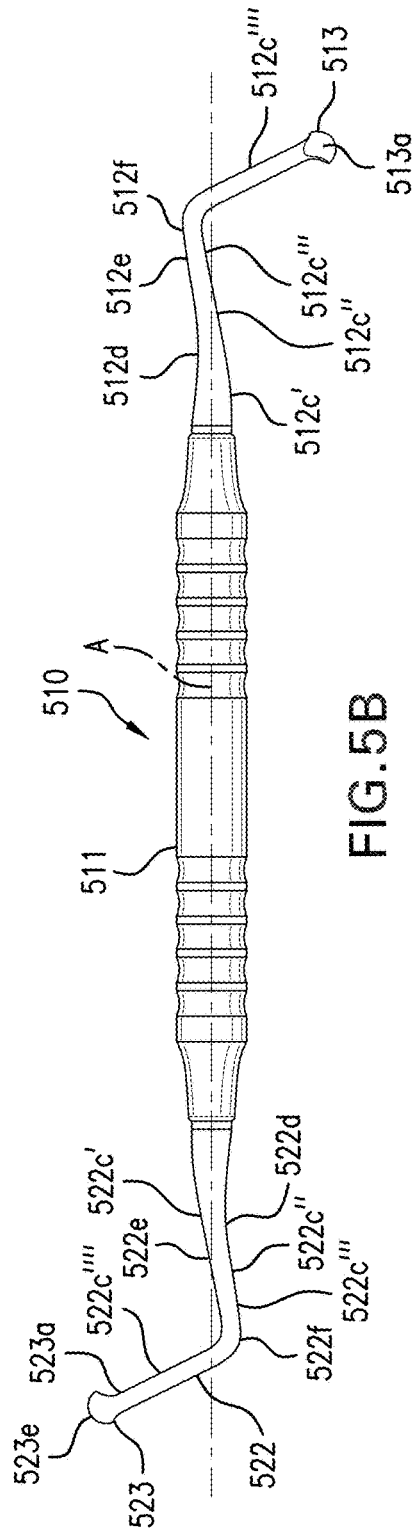
FIG.5A
FIG.5B

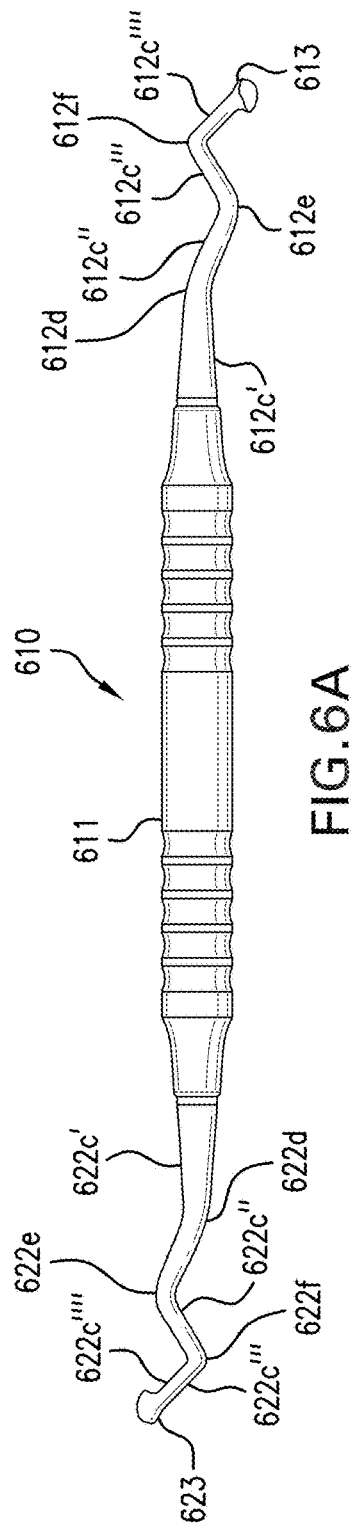
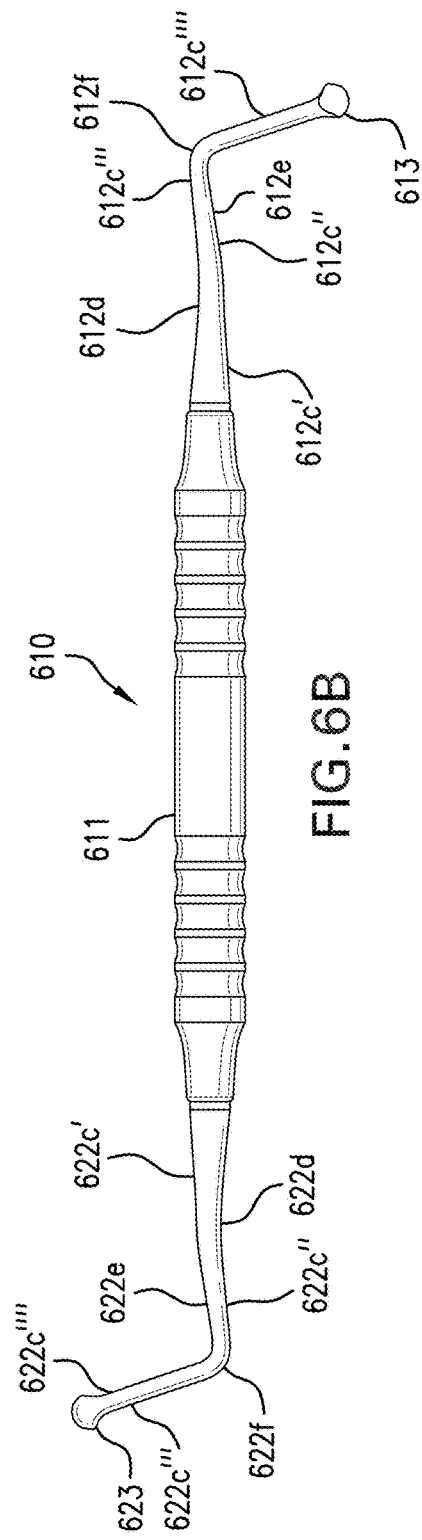
FIG.6A
FIG.6B

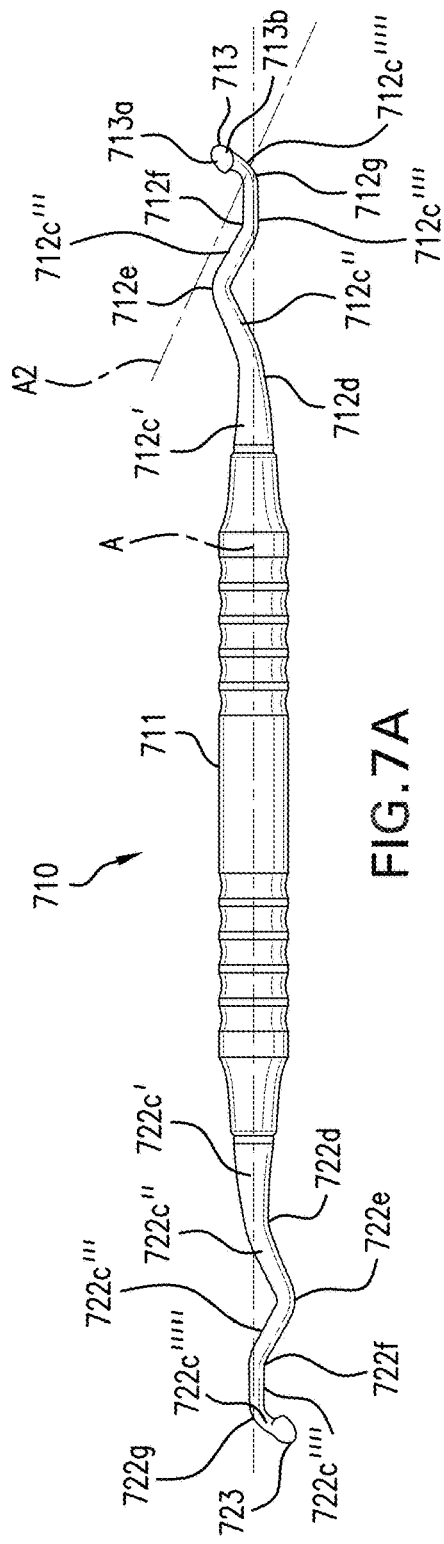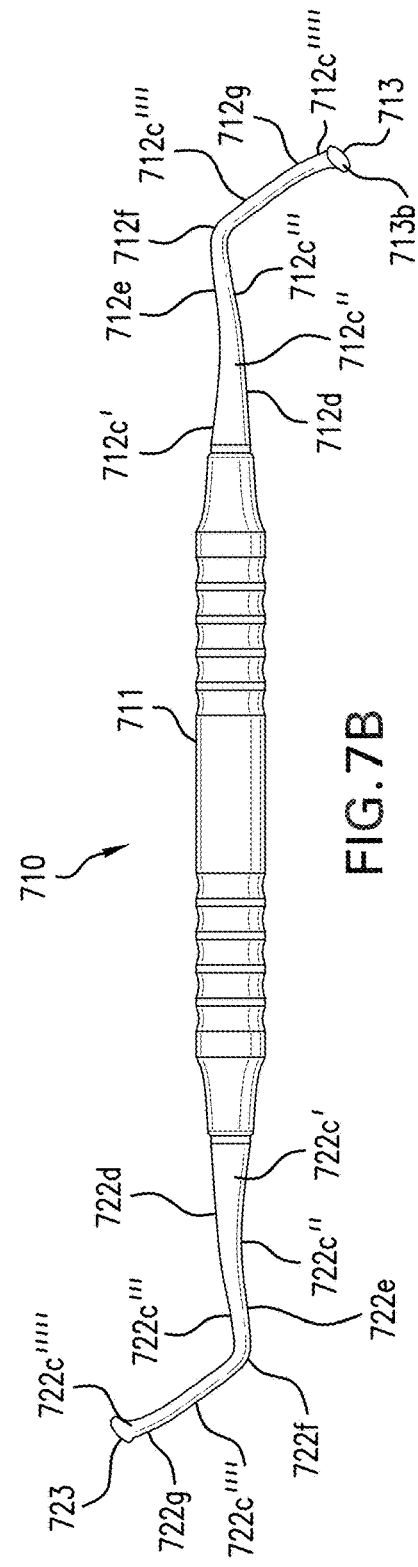
FIG.7A
FIG.7B

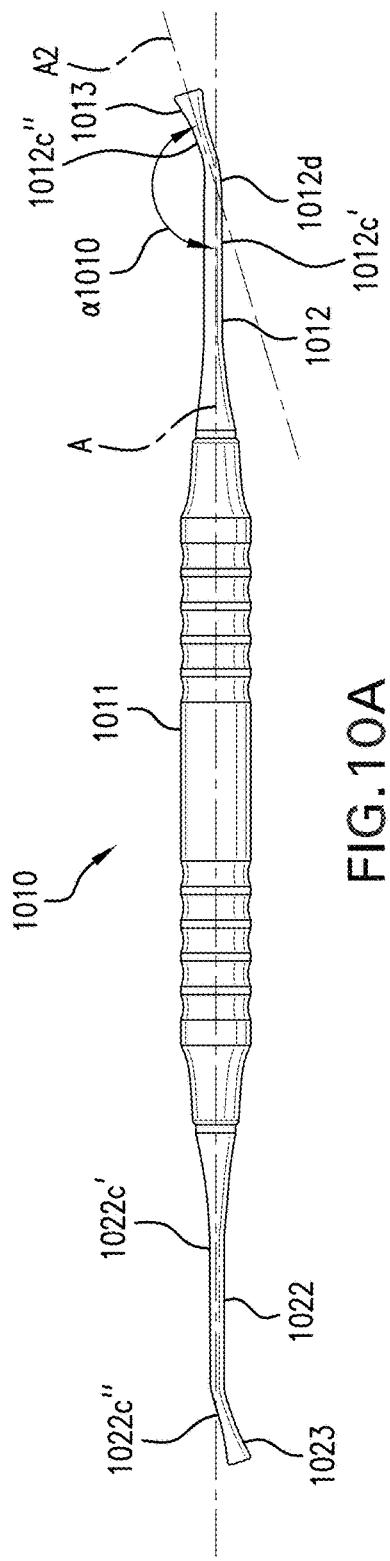
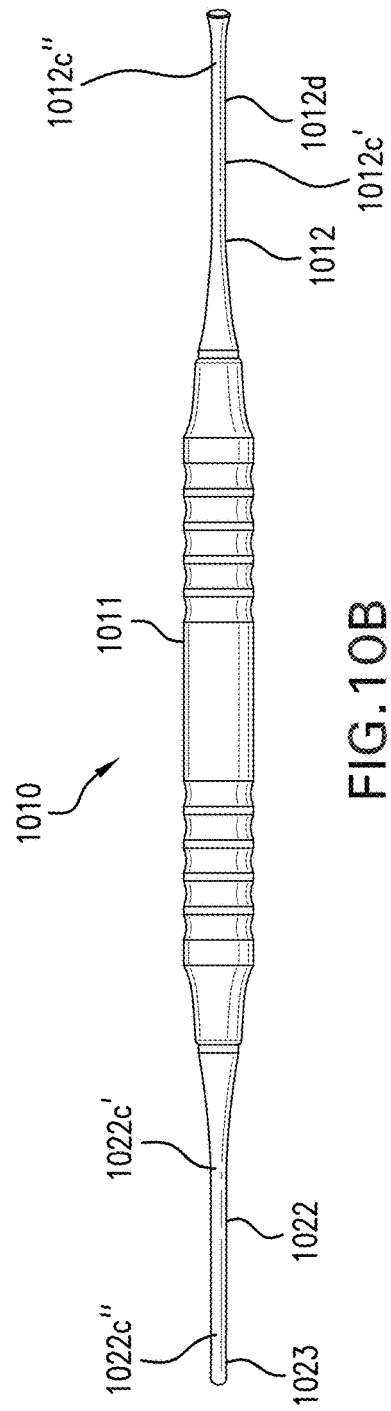
FIG. 10A
FIG. 10B

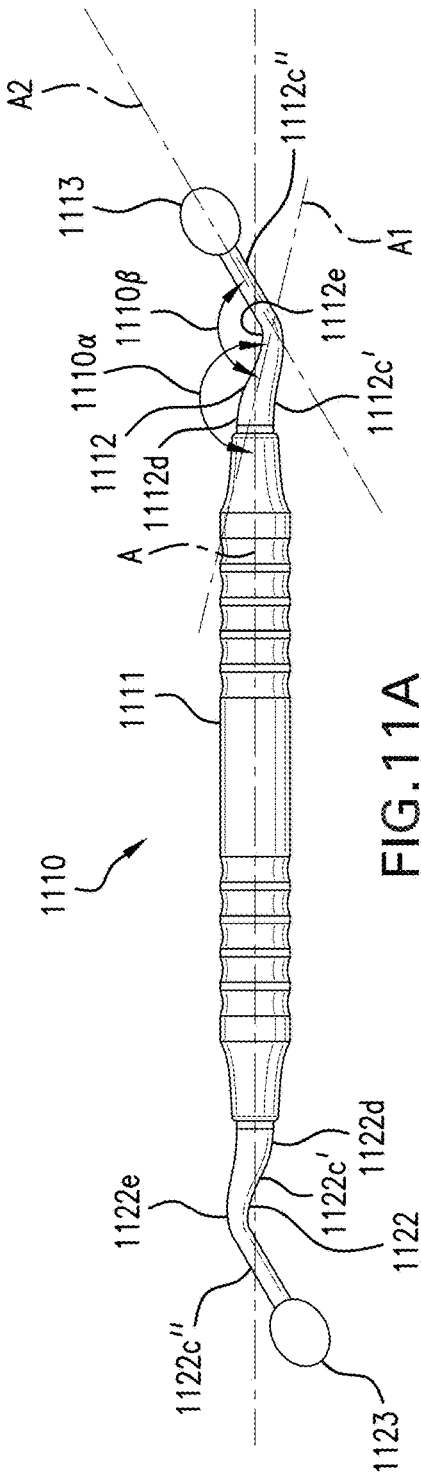
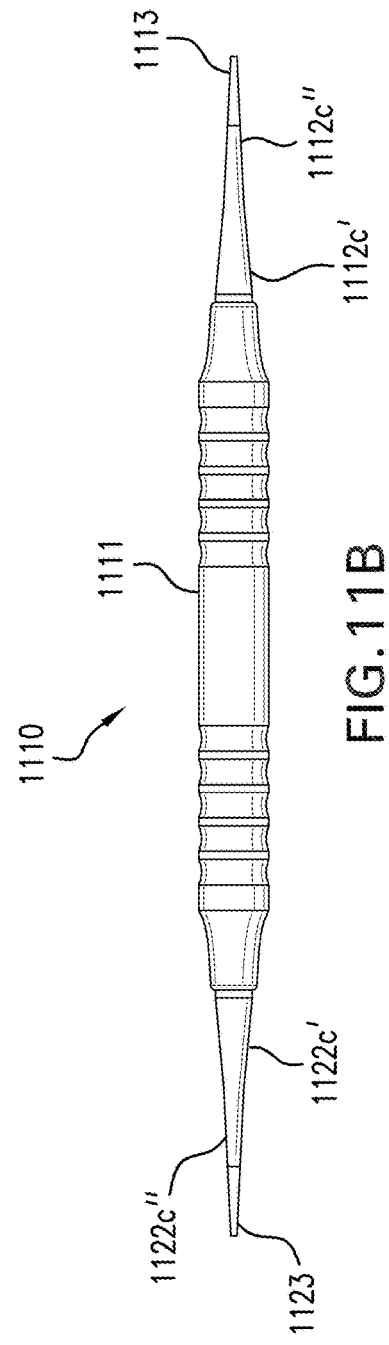
FIG. 11A
FIG. 11B

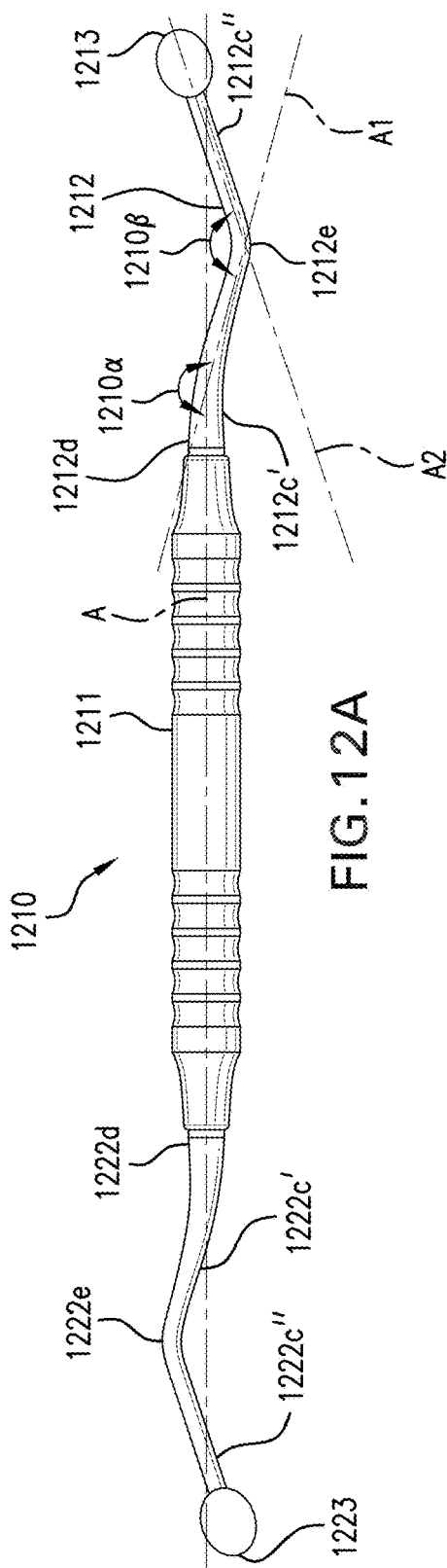
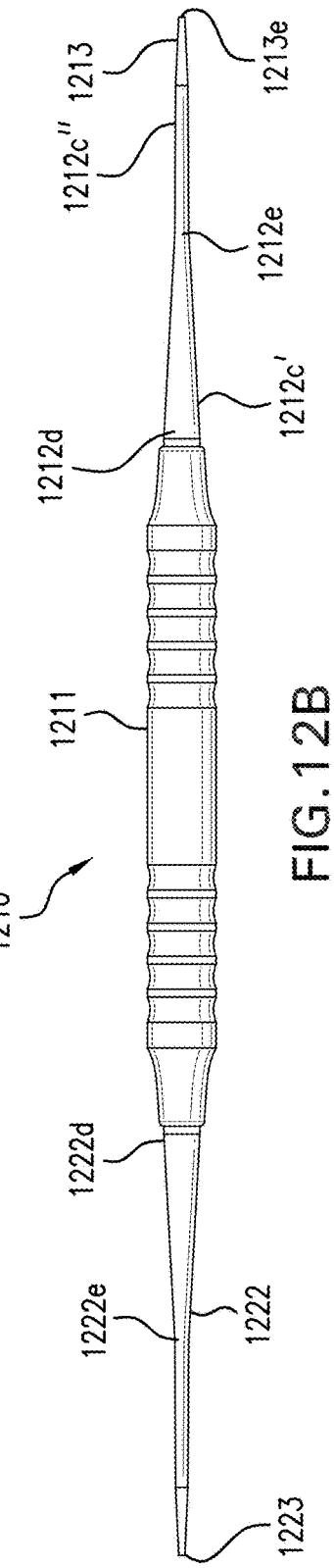
FIG.12A
FIG.12B

•Syringe 1
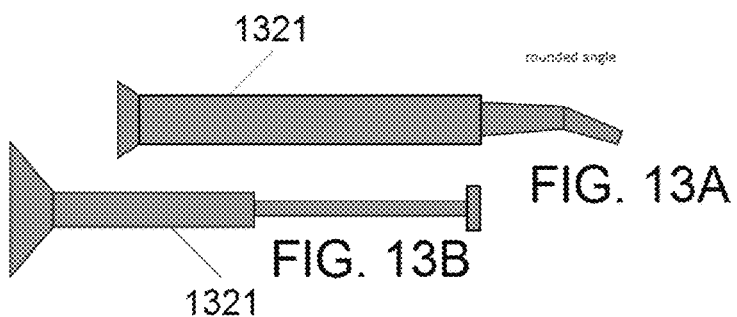
FIG. 13A
FIG. 13B
•Syringe 1a
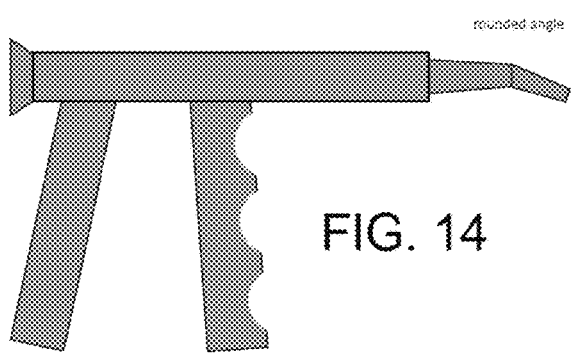
FIG. 14

METHOD, DEVICES AND ARTICLES FOR CONDUCTING SUBPERIOSTEAL MINIMALLY INVASIVE AESTHETIC JAW BONE GRAFTING AUGMENTATION

CROSS-REFERENCE TO RELATED APPLICATIONS

This patent application claims the benefit under 35 U.S.C. § 119 and 35 U.S.C. § 120 and is a continuation-in-part of International patent application Serial No. PCT/US17/25478, filed Mar. 31, 2017, and U.S. provisional application Ser. No. 62/316,140, filed Mar. 31, 2016, each entitled "Method, Devices And Articles For Conducting Subperiosteal Minimally Invasive Aesthetic Jaw Bone Grafting Augmentation", the complete contents of which are herein incorporated by reference.

BACKGROUND OF THE INVENTION

1. Field of the Invention

The present invention relates to methods, biomaterials, instruments, devices, software and digital tools for minimally invasive reconstruction of the jaw, namely bone, soft tissue, gingival papillae and the attachment apparatus whereby teeth and dental implants are attached to the jaw bone, and more particularly to subperiosteal augmentations and reconstructions, implantable jaw bone graft substrates, and apparatus for facilitating carrying out the methods; including digital tools and software that allow for surgical planning and surgical navigation to perform the jaw bone grafting method.

2. Brief Description of the Related Art

The human jaw bone is the supporting structure for teeth, and may be affected by a number of conditions, including age, congenital abnormalities, medical treatments, injuries, disease and trauma. The human lower jaw bone is referred to as the mandible, and the upper jaw is known as the maxilla. In a number of instances, the mandible and maxilla may change as a person ages. Reconstructions of the mandible and maxilla are carried out to correct physiologic and pathologic conditions, to remediate an aesthetic condition or appearance, or both. Subperiosteal augmentations with biomaterials to reconstruct the jaw bone may be used in individuals that have a shallow jaw bone, or jaw bone deficits due to congenital factors, disease or trauma.

Aesthetic outcomes in implant therapy are predominantly dependent on the peri-implant soft tissue architecture. Traditional bone grafting techniques include releasing incisions, papilla splitting, gingival flap elevation and manipulation to cover the augmented volume. Regardless of the degree of bone augmentation achieved, the soft tissue results often include gingival deformities leading to compromised esthetics. A relationship between the complexity of the augmentation procedure and the degree of peri-implant soft tissue deformity has been documented in the literature. Typically, the more complex procedures exhibit an increase in the level of deformity of the soft tissue. Therefore, although minimally invasive procedures have been advocated, there are certain problems encountered that have not been resolved (i.e. vertical bone augmentation, new attachment regeneration on natural teeth or implants, and gingival papillae reconstruction).

The present invention avoids many of the foregoing problems and permits a more effective means for minimally invasive subperiosteal augmentations and reconstructions, and minimizes the time, number of procedures, complications, morbidity and cost for treatment applications.

SUMMARY OF THE INVENTION

Methods and devices for subperiosteal minimally invasive aesthetic jaw bone augmentation and reconstruction are provided. The methods are designed to provide reconstruction of the jaws, including mandibular and maxillary reconstructions including horizontal and vertical bone augmentations. The methods, instrumentation and articles may be employed to support and restore the facial tissues, including lips, cheeks, and nose, with the implantable substrates utilized in the jaw reconstruction. The methods, instrumentation, and articles may also be employed to facilitate reconstruction and regeneration of the apparatus consisting of alveolar bone, periodontal ligament and root cementum, whereby teeth and dental implants are attached to the jaw bone, and the gingival tissue including gingival papillae also is reconstructed and/or regenerated, through the implementation of procedures that manipulate the tissue to accept implantable biomaterials. Reconstructions of horizontal and vertical jaw defects, regeneration of the structures and apparatus whereby teeth and dental implants are attached to the jaw bone in addition to the reconstruction of gingival papillae and correction of gingival recession, may be achieved with the minimally invasive method, instrumentation, and articles, including the implantable biomaterials, of the invention.

Once the jaw bone is reconstructed with the minimally invasive methods and biomaterials prescribed in accordance with the invention, dental implants (e.g., prosthetic teeth), may be placed to restore function. Dental implants are attached to the jaw bone through contact with living, ordered bone, following a healing process known as Osseointegration. Teeth are attached to the jaw bone through an apparatus consisting of alveolar bone, periodontal ligament and root cementum. Reconstruction of horizontal and vertical jaw defects, regeneration of the structures and apparatus whereby teeth and dental implants are attached to the jaw bone in addition to the reconstruction of gingival papillae, may be achieved with the minimally invasive methods, instrumentation, and articles, including implantable biomaterials, of the invention.

The present invention provides an inventive method which is for carrying out bone grafting procedures by implementing minimally invasive bone grafting procedures that include tunneling and placement of graft material carried out to produce improvements over prior grafting procedures. The present method undertakes to introduce graft material through smaller incisions (e.g., less than 6 mm wide), such as, for example, on the order of between about 5-6 mm, or even smaller. According to preferred embodiments, the entry incision is located remotely from the graft site, and preferably are located ½ to 1 tooth distance from graft site, and the graft site is reachable through a tunnel. The present method may be carried out with incisions that may be vertical or oblique. According to some embodiments, a single remote incision may be used to conduct the procedure, while according to other embodiments the number of incisions may depend on the sites to be grafted. The method preferably is carried out to create a subperiosteal tunnel with smaller lumen dimensions while avoiding damage to the periosteum, and preferably is performed using specially designed instruments. According to the present method, a subperiosteal tunnel provides laparoscopic access to the graft site. The smaller tunnel lumen, on the order of 5 to 6 mm or less, minimizes or more preferably prevents graft migration. The graft material may remain at the installation site as intended to provide the desired augmentation at the location for attachment of a dental implant (e.g., a prosthetic tooth or teeth). According to preferred embodiments, specially designed instruments are inserted through the tunnel to create a subperiosteal pouch. The method preferably involves developing the subperiosteal pouch with a clearly defined perimeter. The graft material is delivered to the subperiosteal pouch, and preferably, a specially designed carrier is used to effect delivery of the graft material to the desired location, the pouch. The method aggregates the bone graft material within the pouch confines, and preferably, through distension of the soft tissues, the bone graft material is able to remain situated within the defined area or zone of the pouch. Augmentation is achieved by aggregation of the bone material, such as xenograft particles, within the confines of the subperiosteal pouch, causing distension of the soft tissues. According to the method, the graft material is compacted, condensed and shaped while in the pouch. The method may be carried out using specially designed instruments which may be used to compact, condense and shape the graft material, including at the pouch site.

According to preferred embodiments, the method for augmentation may be carried out using specific biomaterial/biologics combination, such as, for example, bovine xenograft particles and PDGF (platelet derived growth factor). According to preferred embodiments, the method may be carried out without decortication.

The method of jaw augmentation is carried out without the use of space maintaining devices. Space maintaining devices, such as tenting screws or titanium mesh are not utilized or required. The method also preferably is carried out without the use of cell occlusive membranes. In accordance with the method direct contact between the bone material and the tissue forming the tunnel and pouch is effected. According to some embodiments, full thickness interrupted sutures are used to evert the wound edges. The remote location of the incision allows tension to be distributed over a wider area of the soft tissue, facilitating wound co-aptation. The remote incision location also minimizes or prevents periosteum injury and resulting inflammatory reaction from interfering with healing of bone graft. The method also may be carried out using particulate graft composition and formulations, as well as molded grafts to be delivered laparoscopically. Embodiments of the method also may be carried out using computer aided graft planning and design. Navigation through the periosteum may be carried out with instrumentation configured to create a remote incision, develop the tunnel and produce a subperiosteal pouch, as well as to introduce bone graft material to the site. The method may be implemented using a scope, such as a laparoscopic system, which, for example, may include a lumen that is maneuverable through the remote incision and tunnel, through which also, a camera, light source, and instrumentation may be inserted, so that the method may be conducted with visibility of the site, and access through the laparoscopic system. Embodiments of the method also may be carried out with the use of piezosurgery devices and laser tips, which may be introduced through the remote incision for stimulation of difficult sites prior to grafting.

According to some embodiments, implementations of the method may include forming customized granular or molded bone grafts or bone/collagen grafts in different configurations for use to address a specific defect or situation present in the individual. A preferred implementation includes S.M.A.R.T. granular graft biomaterial comprised by particles of a specific size and tri-dimensional shape such that will favor aggregation once delivered to the target site. ("S.M.A.R.T." as referred to herein is a proprietary trademark owned and/or used by Applicant and/or authorized licensees.) A preferred implementation includes packaging the granular material following a specified granule density into a S.M.A.R.T. subperiosteal syringe with a specially designed shape, lumen, plunger and tip; that is introduced into the subperiosteal tunnel access and engineered to deliver the particulate material at a gradual rate of deposition and with minimal to moderate pressure. Another preferred implementation includes the mixture and packaging of the S.M.A.R.T. granular graft material and a biologic agent or growth factor in specific dosages. The biologic agent may be utilized to pre-treat the granular material, or they may be mixed together at the time of surgery. This embodiment may apply to any packaging implementation of the granular biomaterial, including that loaded into the subperiosteal syringe. An additional preferred implementation includes several S.M.A.R.T. graft molds, shapes and blocks; configured in different designs, compositions and dimensions; which may be infused by or offered in combination with biologic agents or growth factors. These molds, shapes or blocks are designed specifically to be inserted into a subperiosteal tunnel, and subsequently manipulated and delivered into a subperiosteal pouch. The S.M.A.R.T. molds, shapes or blocks may be manufactured from allogenic or xenogenic bone, or a mineral or artificial bone substitute. They may be comprised of bone, mineral or artificial particles held together by collagen or a suitable biologic adhesive.

Some embodiments of the method may involve the utilization of a laparoscopic approach where a thin tube (which is preferably lighted, and may include a camera), is inserted into or beneath the oral soft tissues. For example, the light may be provided by a thin fiber which preferably is an optical fiber. The tubular instrumentation may include a lumen with one or more actuatable tools that facilitate developing a tunnel within the tissue. A lumen also may include one or more actuatable tools that may be used to manipulate the tissue, such as, for example, the periosteum tissue, to form a pouch structure therein. Some embodiments of the lumen include steering mechanisms or other surgical navigation mechanism for directing the path of the instrument through the tissue to form a passageway or tunnel in the tissue. For example, the bone graft location, extension, and laparoscopic approach may be mapped digitally. Specialized attachments may be utilized for recognition by a surgical navigation system.

Additional embodiments include a suite of digital tools and software that will allow for planning of the S.M.A.R.T. graft design, extension, subperiosteal access and navigation tri-dimensionally using tomographic images. A preferred implementation includes a software embedded algorithm to calculate the total volume of the graft. Another preferred implementation includes a library of S.M.A.R.T. graft shapes, molds or blocks of different designs and dimensions existing within the digital tools, which can be dragged and positioned into the computer aided S.M.A.R.T. graft design for virtual testing. The volume calculating algorithm will automatically and dynamically deduct the volume of the S.M.A.R.T. shape selected, and show the remaining volume of graft material required to complete the digitally designed S.M.A.R.T. graft. An additional preferred implementation includes digital tools and software tools to allow surgical planning and navigation through the subperiosteal tunnel, surgical navigation to create the subperiosteal pouch and subsequently implant the graft material in the site.

The method involves making a remote incision or incisions, which are preferably located remotely of the surgical site where the activity is to be carried out. The method further involves developing a subperiosteal access or tunnel. The tunnel, according to preferred embodiments, is developed in a location between the periosteum and the jawbone, and is formed, preferably, beginning at the remote incision, to form a passageway that advances below the periosteum from the remote incision providing access to the surgical site. Once the access to the site is developed through the remote incision and the tunnel, the method proceeds with the formation of a subperiosteal pouch. These procedures must be carried out by specially designed instruments to avoid damage to the periosteum. According to a preferred implementation, the subperiosteal pouch is created by elevating the periosteum of the site to the extent necessary to accept the volume of biomaterials to be grafted. The pouch must be created to house but also to confine the graft in such a manner that the desired volume can be achieved by aggregation of the biomaterial and expansion of the soft tissues within the target area, while limiting undesired migration of the graft. According to some embodiments, the elevation of the periosteum, creation of the tunnel and subperiosteal pouch preferably may be carried out with instruments specifically configured for implementation of the method without damage to the periosteum.

Alternative embodiments of the method include special piezosurgical inserts and tips to be introduced into the subperiosteal tunnel, and used to prepare, score or activate the bone surface within the subperiosteal pouch. According to preferred embodiments, the S.M.A.R.T. piezosurgical insert is configured having a shank exhibiting a flat, circular or elliptical cross section to facilitate maneuverability within the tunnel. A unilateral serrated or textured blade is positioned at the end of the tip to direct the piezo-energy only to the bone surface. The active serrated or textured portion of the tip may be provided at an angle relative to the long axis of the insert shank.

Additional embodiments of the method include a laser tip that is attached to a hard tissue laser unit, for the purposes of scoring, activating or stimulating the bone surface within the subperiosteal pouch. The S.M.A.R.T. laser tip is designed with a shank that facilitates maneuverability within the subperiosteal tunnel, and transmits the laser beam laterally so that it may be aimed at the bone surface of the subperiosteal pouch.

According to preferred implementations of the method, the subperiosteal pouch is formed having a suitable configuration (such as the size and shape) to house granular or molded implantable biomaterials that are to be located and installed at the site. Preferably, the pouch is configured to confine the graft and maintain the graft in a desired position.

According to preferred embodiments, the graft may be made from a mammalian or mineral material, processed with one or more agents. Preferred embodiments may be comprised from human, bovine, equine, porcine or other mammalian bone, and preferably anorganic bovine bone (e.g., non-living bone). One preferred graft composition comprises anorganic human, mammalian or mineral bone particles that are treated or mixed with biologic agents including growth factors, collagen or other binding or adhesive agents. The granular biomaterial bone graft substitute is configured with a specific particle size (or sizes) and tri-dimensional shape that favors mechanical aggregation, compaction and cell ingrowth. The bone may be processed in one or more steps, such as extractions and demineralizations, prior to the addition of a collagen, binding, or adhesive agent. According to some alternate embodiments, the bone graft is a milled or 3-D printed biomaterial, which may be combined, coated or treated with one or more substances, such as, for example, collagen or a biologic agent (e.g., growth factors). In yet other embodiments, a milled or 3-D printed bone graft is implanted in conjunction with granular biomaterial, which may be delivered to the surgical site or implantation site, and/or around the graft implantation location through the subperiosteal tunnel. One preferred embodiment comprises a milled or 3-D printed graft fabricated from mammalian bone, (i.e. human, bovine, equine or porcine bone) or mineral biomaterials. The graft may be mixed, coated or treated with biologic agents to bind the graft particles or enhance cellular response. According to some other embodiments, a graft may be formed from a graft composition that comprises anorganic bone particles (processed through extractions and demineralizations) with one or more agents, such as growth promotors, growth factors, platelet derived growth factors, or other biologic agents such as collagen, adhesives and binders. The graft architecture and composition preferably is suitably held together to allow implantation and delivery through the subperiosteal tunnel to the surgical site. Binding or adhesive agents may be mixed with the particles to form certain shapes or molds, or added at the site.

According to preferred embodiments, a specially designed carrier may be used to deliver the bone graft to the surgical site. Preferably the carrier may have a shape, dimensions and angulation that facilitates delivery of the bone graft through the remote incision and the subperiosteal tunnel that leads to the site of implantation. The specially designed carrier delivers the graft in a gradual fashion, with a plunger and handle design that controls the rate of expression of the bone graft particles. The plunger may be operated with manual pressure, or through a mechanical pump or device that may be computer assisted or controlled. A preferred implementation includes a specially designed subperiosteal syringe loaded with the granular bone graft material, which may be mixed with collagen or suitable binding or adhesive substances to create a paste. This subperiosteal syringe will be of a size, shape, cross section, lumen, plunger and tip design that will facilitate its introduction and maneuverability within the subperiosteal tunnel, to gradually deliver the particulate graft or paste to the subperiosteal pouch. According to a preferred implementation, once the bone graft is loaded into or onto a carrier (i.e., or may be held by a carrier) and delivered to the site, it is condensed and adapted to achieve the degree of bone augmentation desired. It may also be activated with biologic or chemical agents to set to a solid or semisolid form. Preferably, the condensing is carried out with the specially configured instrument, referred to as an elevator, spatula or condenser, which, according to preferred embodiments, is provided having a holding area and double or single ends, on which a condensing element is provided. The condensing element preferably is connected to the holding area with a maneuverable arm. The condenser provides maneuverability of the condensing element (which may be provided at each end thereof), so that the condensing element may be inserted into the remote incision and maneuvered through the tunnel and at the surgical site where the implantable article is positioned. The condenser is used to pack the bone graft into the site, while the spatula is used to mold it into an appropriate shape.

According to some alternate embodiments the condenser may be configured as a lumen and may be provided as a condensing tool or end that is configured with a maneuverable lumen that may be directed through a tunnel created in the tissue and leading to the graft. The condenser end may be operated through the maneuvering of the lumen to engage the bone graft and tissue at the surgical site. Preferably, the operation of the condenser end may be carried out from outside of the surgical site and incision.

According to some embodiments, the graft may be fortified with a treatment or binding substance. In some embodiments, anorganic bone particles are admitted to the site to fill in around one or more areas of the graft or pouch. Agents, such as a biologic agent, growth factors (e.g., platelet derived growth factors), collagen, adhesive or binding agent may be mixed with the graft particles or provided at the graft location. The materials may be admitted to the graft or graft site with an instrument, which may be a specially configured subperiosteal syringe. The syringe may have a special tip configuration and shape designed to elevate the mucosal tissue along the incision and facilitate insertion into the subperiosteal tunnel. The syringe may have a plunger that is specially designed to distribute its contents in a particular direction and dispense the graft particles at a certain rate. Other embodiments provide a specially configured syringe that has a maneuverable lumen end for manipulating the syringe end through the tunnel passageway and to position the end for delivery of content at desired locations in the pouch or graft site. Alternative embodiments include a specially configured syringe and plunger to express a paste like material containing the bone graft particles.

Upon completion of the installation of the bone graft and condensation and adaptation in place at the site, the incision is closed, preferably by suturing or by utilizing another suitable technique.

The present method and devices are designed to minimize or eliminate potential peri-implant soft tissue disfigurement. The method and devices also provide a way to achieve consistency in horizontal and vertical augmentation of the jaw. The method and devices are designed to be implemented without losses to bone volume, and preferably, are also designed to equal or exceed the degree of bone volume of existing flap based techniques. The predictability also is improved with the present method and devices. The number of procedures, morbidity, complications and costs are also reduced with the present method and devices.

According to some embodiments, the method may be implemented for delivering bone material provided to augment bone to strengthen or improve an already existing implant, such as, for example, a metal implant that was installed on the mandibular or maxillary structure of a patient in place of a tooth. For example, in the case of an already existing implant that is lacking in bone e.g., as a result of improper placement or bone loss that has taken place over the years, the method may be carried out to deliver bone material to the implant site in a minimally invasive manner, and in particular, to minimize the disruption of the tissue at the implant site.

The methods may be used to remediate patient conditions where the addition of bone is beneficial to correct or improve a defect, trauma, loss of bone, or to support an existing tooth (or portion thereof, e.g., a root). For example, the method may be used to deliver bone graft material to address a concavity in the bone structure, recession, bone deficit, or other developmental issue, to develop an alveolar ridge, or to enhance the permanent root of a tooth.

In addition, the method may be used to deliver bone graft material to a site contemporaneously with the placement of an implant, or may be carried out to strengthen the implant site to receive an implant at a future time.

According to preferred implementations, the method and devices may be used to carry out restorations and augmentations, including, for example, vertical augmentation applications involving the jaw, which may be performed at both, mandibular and maxillary locations. According to preferred embodiments, devices comprised from human, bovine, equine, porcine and mineral bone are provided specifically for vertical augmentation of the jaws using the present method of minimally invasive subperiosteal approach. According to preferred embodiments, these devices are designed with certain shapes and sizes to accommodate different jaw bone defects.

The present method and utilization of the devices may be carried out to provide subperiosteal augmentation of the jaw without the need for the use of a membrane, such as a cell-occlusive membrane or space maintaining membrane, and without the step of installing the membrane. The present method and devices also facilitate jaw bone augmentation without the use of tenting screws or other space maintaining devices such as a titanium mesh and titanium reinforced membranes.

According to preferred embodiments, devices are provided that facilitate carrying out the technique. In particular, the remote incision may be made using any suitable cutting device. However, preferred embodiments of instrumentation that facilitates tunneling from the remote incision to an active surgical site are provided. According to some preferred embodiments, the instruments are constructed with one or more cutting features or elements, and straight or angled shanks with specially designed tips to facilitate the elevation of the periosteum from multiple surgical approaches. Preferred embodiments preferably are maneuverable and may be utilized by moving the active portion of the instrument (e.g., cutting tool, camera and/or light) from the remote incision location, through the tunnel, and to the active surgical site. Instruments, according to the invention, may be configured to make the incision and form the tunnel. According to some preferred embodiments, the instruments include an arm (and some embodiments may include a tube or wire/cable) which may be maneuvered and steered through a direction or directions as desired by the operator (e.g., a surgeon).

Preferred embodiments of the instruments preferably include a tunneling instrument. The tunneling instrument may be utilized to make the incision, develop the tunnel, and operate at the active site by forming a pocket for the graft and carrier. The tunneling instrument may be formed with a cutting portion that is disposed on a maneuverable arm that permits the tunnel formation by maneuvering the instrument arm and cutting portion through the tissue. The tunneling instrument may be configured as a syringe, or, alternatively, may be configured as an elevator that may include specially designed tips to facilitate the separation of an intact periosteum layer in several directions. The instrumentation may incorporate shanks or handles with one or more offsets, bent at different angles and lengths to facilitate maneuverability within the tunnel. The handles and shanks may also have markings measured in linear fashion from the tip, to help the operator identify the location and extension of the elevator tip within the tunnel. For example, according to some embodiments, the tunneling instrument may be configured for use in forming a subperiosteal pouch. According to preferred embodiments, the instrument may include one or more mechanisms that may be utilized to maneuver or manipulate the periosteum to create the pouch.

The instrumentation may include a holder that has a holding mechanism, such as, for example, forceps, pliers, hemostats or other grasping mechanism, to hold the carrier and/or graft, and manipulate the carrier and/or graft from a location outside of the incision, through the tunnel, and to the remote surgical site. A preferred implementation is a specially designed subperiosteal syringe, into which the particulate bone graft material is loaded, functioning as a carrier to transport the graft material through the tunnel and deliver it into the subperiosteal pouch. The subperiosteal syringe has a special tip design beveled at a 45 degree or greater angle to facilitate its introduction into the subperiosteal tunnel and elevation of the mucosa, and to direct the expression of the granular bone graft material within the pouch. The subperiosteal syringe is designed with a specific diameter, semicircular or elliptical cross sectional shape and lumen, to facilitate its maneuverability within the subperiosteal tunnel. Preferred embodiments have a monolithic plunger manufactured to a specific stiffness and incorporating a pointed tip designed to break any aggregation of the granules and facilitate the gradual and controlled expression of the bone graft material. The subperiosteal syringe is fabricated with plastic, composite or resin materials and monolithic designs that will not separate or break, to eliminate the risk of leaving parts or fragments inside the subperiosteal tunnel or pouch. The plastic composition may also allow some flexibility to improve adaptation to the subperiosteal tunnel and maneuverability. The granular graft material may be loaded into the subperiosteal syringe at the time of surgery. According to a preferred embodiment, the subperiosteal syringe is packaged preloaded with the granular graft material, using a particle density that will prevent clogging and allow the gradual and controlled expression from the syringe into the subperiosteal pouch. The granular graft material may be mixed with binding or adhesive agents to create a paste-like consistency. The tip of the syringe is sealed with a rubber or silicone stopper. Biologic agents, growth factors, or activators may be injected through the rubber of silicone stopper to infuse the granular graft material prior to use.

The instrumentation preferably may comprise one or more instruments which are configured to allow manipulation and maneuverability of the carrier and/or graft, and provide a mechanism for manipulating the periosteum at the surgical site and forming the subperiosteal pouch. According to some preferred embodiments an elevator is provided. The elevator may include an operational portion or handle for maneuvering or guiding the instrument. According to some preferred embodiments, the elevator may be configured with a maneuverable arm extending from the body or handle, and an elevating end. The elevating end preferably is configured with a cutting edge, and may be manipulated to elevate the periosteum and form a pouch. According to some alternate embodiments, the elevator may be configured as a lumen with an elevator tool end. The elevator end may be manipulatable and actuatable from outside of the incision. An alternate embodiment may be configured with a handle that will accommodate the attachment of a positioning device to work in conjunction with surgical navigation systems. The elevator may be configured to apply pressure to the surgical site and elevate the periosteum to form or further configure the pouch.

According to some preferred embodiments, the instrumentation may be provided in the form of a kit or separate kits which includes the components and mechanisms that may be utilized for carrying out the method. According to some preferred embodiments, the instrumentation is provided as a kit or separate kits which may be adapted to pre-existing instruments, and/or steering and viewing devices. According to some other devices, the instrumentation may be a complete kit which includes one or more displays, mechanisms for steering and moving the cutting and grasping elements of the instruments.

Preferred embodiments include specially designed tips that attach to a piezoelectric surgical unit, and direct the piezoelectric energy to the surface of the bone within the subperiosteal pouch. Alternative preferred embodiments include specially designed laser tips that attach to a hard tissue laser unit (i.e. Er:YAG or Nd:YAG), and transmit the laser beam to the surface of the bone within the subperiosteal pouch. The treatment of the bone surface with the laser energy provided by the laser tip prepares, stimulate or activates the recipient site for the bone graft, which preferably, is beneficial to promote growth and adhesion of the graft in situations where delayed or difficult healing may be expected.

The pouch is created to house and confine a graft. Preferred implementations of the method configure the pouch within the periosteum, e.g., the dense layer of vascular connective tissue surrounding the mandible and/or maxilla. The instruments preferably are constructed to facilitate the pouch formation by enabling the user to manipulate the instrument, either mechanically or electronically, to elevate the subperiosteal tunnel. The elevation of the tunnel is accomplished, and preferably is elevated at the location where the bone graft is to be installed. This prepares the site for the reception of the grafting material that is to be delivered to the location (e.g., a prefabricated bone graft).

According to preferred embodiments, implantable articles may be specially configured bone or bone/collagen grafts, customized to an individual's condition and jaw structure. They may contain binding or adhesive agents. These devices may be utilized for vertical and horizontal augmentation, and may be provided in certain designs and sizes to accommodate different jaw bone defects. According to some implementations, the bone grafts may be formed by imaging the individual's jaw location where the implantable article is to be installed, and using the image to generate a customized bone graft. The bone graft preferably may be an allograft or xenograft formed from anorganic bone particles, and may also include treatment with a biologic agent. In addition, according to some alternate embodiments, the customized bone graft may be formed using 3D printing. The printing may be implemented in conjunction with the imaging of the individual, and manipulation of that image, if desired, to produce an appropriately sized and shaped article for implantation, which preferably is made from human or xenogenic bone. Some embodiments may comprise a 3D printed human, mineral or xenogenic graft. Alternate embodiments may include mixing the granular bone graft particles with binding or adhesive agents to create implantable devices of different shapes. The human, mineral and xenogenic grafts preferably may be further configurable and manipulatable at the site, in accordance with the method.

The present method and devices may be used to carry out a procedure that is designed to be less invasive than prior methods. According to preferred embodiments, the method and device usage may be implemented to carry out subperiosteal augmentations and reconstructions in the maxillary anterior region with minimal or no risk of disfigurement to the patient.

BRIEF DESCRIPTION OF THE DRAWING FIGURES

FIG. 1A is a top plan view of an exemplary embodiment of device according to the invention configured as an elevator.

FIG. 1B is a right side elevation view of the device of FIG. 1A.

FIG. 2A is a top plan view of an alternate embodiment of a device according to the invention configured as an elevator, being similar to the device of FIG. 1A, having a longer reach.

FIG. 2B is a right side elevation view of the device of FIG. 2A.

FIG. 3A is a top plan view of a third alternate embodiment of device according to the invention configured as an elevator.

FIG. 3B is a right side elevation view of the device of FIG. 3A.

FIG. 4A is a top plan view of a fourth alternate embodiment of device according to the invention configured as an elevator, being similar to the device of FIG. 3A, having a longer reach.

FIG. 4B is a right side elevation view of the device of FIG. 4A.

FIG. 5A is a top plan view of a fifth alternate embodiment of a device according to the invention configured as an elevator.

FIG. 5B is a right side elevation view of the device of FIG. 5A.

FIG. 6A is a top plan view of a sixth alternate embodiment of a device according to the invention configured as an elevator, being similar to the device of FIG. 5A, having a longer reach.

FIG. 6B is a right side elevation view of the device of FIG. 6A.

FIG. 7A is a top plan view of a seventh alternate embodiment of device according to the invention configured as an elevator.

FIG. 7B is a right side elevation view of the device of FIG. 7A.

FIG. 10A is a top plan view of a tenth alternate embodiment of device according to the invention configured as a condenser, being similar to the device of FIG. 9A, having a longer reach.

FIG. 10B is a right side elevation view of the device of FIG. 10A.

FIG. 11A is a top plan view of an eleventh alternate embodiment of device according to the invention configured as a compactor.

FIG. 11B is a right side elevation view of the device of FIG. 11A.

FIG. 12A is a top plan view of a twelfth alternate embodiment of device according to the invention configured as a compactor, being similar to the device of FIG. 11A, having a longer reach.

FIG. 12B is a right side elevation view of the device of FIG. 12A.

FIGS. 13A and 13B illustrate an exemplary embodiment of a syringe according to the invention, with the syringe barrel depicted in a top plan view in FIG. 13A and the plunger mechanism in FIG. 13B.

FIG. 14 illustrates a side elevation view of an alternate exemplary embodiment of a syringe according to the invention, shown in a side elevation view.

DETAILED DESCRIPTION OF THE INVENTION

Figure 1C:
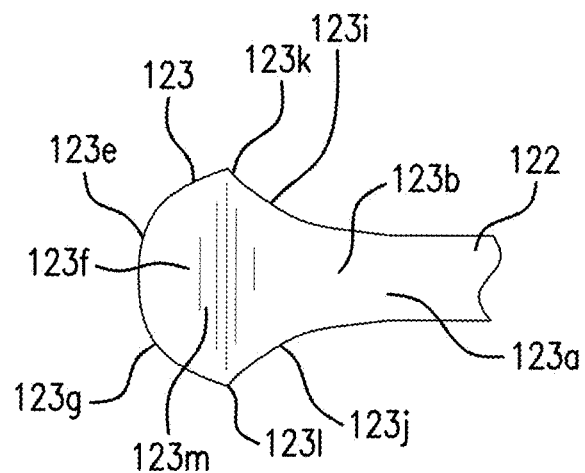
FIG. 1C is an enlarged partial view of the device of FIG. 1A, showing the tip end.

A method, implantable devices, digital planning and navigation, and instrumentation are provided for jaw reconstruction of the maxilla and mandible, and preferably for carrying out subperiosteal minimally invasive augmentations and reconstructions of horizontal and vertical defects of the jaw bone, the biologic structures that attach teeth and dental implants to the jaw bone, and the gingival papillae. The method may also be utilized to build bone before tooth movement, as in orthodontic tooth movement, when the teeth are required to be moved into an area or in a direction where bone is deficient. The method may also be utilized to build bone after tooth movement or orthodontic movement, where the teeth have been moved into an area or position where bone is deficient. Another preferred embodiment of the method includes placing the bone graft material for the purposes of supporting the cheeks, lips, and nose; and to modify facial appearance and improve facial esthetics. The present method may be implemented utilizing a subperiosteal approach, where instrumentation is maneuvered through an incision to treat a remotely situated surgical site. According to a preferred embodiment for implementing the method, procedures to prepare the patient and the surgical site are carried out. This may include cleaning and sanitizing the site, and/or localizing the site and its access paths with one or more coverings, dams, retractors, or the like. A suitable anesthetic may be applied to the patient, including general or local anesthetic, injections, topical, or combinations of these. Once the site and individual are prepared, a surgical cutting tool, such as a scalpel or blade or micro-surgical instrument, is used to make an incision or several incisions. According to some preferred embodiments, the incision may be produced using one or more specially configured instruments, such as, for example, an elevator or syringe, which may be constructed having an operating portion with a maneuverable arm and a cutting element at the end of the maneuverable arm. The location of the incision is predetermined by selection of a location on the tissue, adjacent to the surgical site that is to receive the implantable biomaterial device, but which is remotely situated in relation to the surgical site. The incision comprises a remote incision, which is remote from the surgical site where implantation of the implantable article (e.g., bone graft) is to take place. It is this remote incision location that will be the entryway through which grafting material may be admitted and transported or maneuvered to the surgical site. The surgical site preferably is located under the periosteum, at a distance from the remote incision location. Once the incision is made through the mucosal or gingival tissue, developing a tunnel in the periosteum is carried out to provide access to the surgical site. The tunnel preferably is developed using a surgical tool which elevates the periosteum, creating a path from the remote incision leading to the surgical site. The tunnel preferably is designed to admit material that is used for the reconstruction or augmentation, which may be delivered through the remote incision and ultimately to the surgical site.

Suitable surgical tools that may be used to form the tunnel include a routing tool that may be used to develop the tunnel by creating a controlled path from the remote incision to the surgical site. The tunneling tool may have a cutting element provided thereon which may be stationary, or, which according to some other embodiments, may be operably controllable to rotate (or be rotated or maneuvered) and create a path as directed by the operator (e.g., surgeon or medical personnel). According to some embodiments, the tunneling instrument may comprise a laparoscopic instrument, which may have a lumen and one or more cutting elements within the lumen, or extending or extendible outwardly therefrom. The instrument preferably is sized both in its length and diameter to be suitable to produce the desired tunnel size. The tunnel preferably is configured to allow passage of the implantable material, such as a graft, to be moved from the remote incision to the surgical site location using the tunnel passageway.

The tunneling instrument may be configured with a mechanism for maneuvering the instrument through the tissue to develop the tunnel leading to the surgical site. According to some embodiments, the tunneling instrument may be configured to comprise a steering mechanism for steering the tunneling instrument. According to some embodiments, the steering mechanism may comprise one or more of magnetic or other suitable electric or electronic steering components. For example, according to one exemplary embodiment, a steerable medical probe device, such as, for example, a lumen or catheter may be configured with a body or sheath in conjunction with a plurality of electrical conductors. The electrical conductors may be insulated, and, according to some embodiments, may be arranged to encircle the lumen body. According to some embodiments, manipulation of the tunneling instrument end, (such as the lumen end, e.g., distal end), may be accomplished by providing shape memory wires through which low current pulses are passed to cause the wire ends to contract, and effect movement of the end of the instrument or lumen. The tunneling tool provided on the lumen end may be guided and directed by operating a control that delivers the current to the wires. Accordingly, a plurality of thermally reactive wires may be controlled to manipulate the movement and directions of the instrument. The instrument preferably provides the operator (e.g., surgeon) to facilitate forming of a tunnel is a desired location within the tissue, as well as guiding the instrument by moving it through the tunnel to address the surgical site. The tunneling instrument also may be controlled to maneuver the end to manipulate the tissue at the remote surgical site. Alternatively, or additionally, the tunnel may be developed using the tools shown and described herein.

According to some embodiments, instruments, such as, for example, tunneling instruments, elevators and condensers, may be configured with a steering mechanism that includes a maneuverable steering lumen or shaft coupled to a control mechanism. The control mechanism preferably provides actuators, such as, for example, a handle and one or more elements for directing the movement of the distal end of the steering shaft or lumen. According to some embodiments, current controlled wires may be used. According to some other embodiments, the steering shaft or lumen may be constructed having a flexible coiled spring. The coil spring may have a lead spring which is fixed in position in relation to an end, such as the distal or tool end of the steering lumen or shaft. The steering arrangement also is configured having one or more steering wires connected at the distal ends thereof to the lead spring. In this type of arrangement, the steering wires are manipulated through operation of the controller (which preferably is outside of the operation site). The steering mechanism preferably disposed the steering wires within the steering shaft or lumen, and each steering wire may attach to a controller. When the controller is operated, directional signals are applied to apply tension on one or more of the steering wires. The control mechanism that applies the tension may be electronic or mechanical. In the case of mechanical arrangements, the steering wires preferably are tensioned by winding the wire in desired increments, which may be done by operating a dial which may rotate a shaft to take up and/or release the steering wire. Alternatively, a tensioning element, such as one or more wedges, may be deployed and moved by operating a control, so that the one or more wedges move the wire. In some instances the steering wires may be disposed so that they move oppositely, where actuation of a tensioning mechanism operates so that one wire (or set of wires) is tensioned and another wire (or other set of wires) is released. Alternatively, each steering wire may be regulated independently, with each wire having an independent control for its manipulation. Other embodiments, provide an actuator, such as, for example, an actuation lever or joystick, that may be moved in a plurality of directions and which maneuver the lumen or shaft end in a desired direction corresponding with the movement of the actuator. According to embodiments, the maneuverable arm portion of the instruments may be configured as a lumen or shaft, and the handle may be configured as an actuator or control. According to some other embodiments, a handle may be detachable provided for guiding the instrument end to the location of the incision. And may be removed to operate the steering mechanism to further direct and manipulate the instrument within the tissue.

Once the tunnel has been created, the surgical site, which preferably is situated remote from the incision and at the end of the tunnel, is then prepared by creating a pocket or pouch for receiving the graft. The tunnel and pouch creation may be carried out together (e.g., where the pouch is formed as an extension of the tunnel). According to some embodiments, the tunneling instrument preferably is configured for use in creating the pouch. One example of an instrument is an elevator which may be used for making the remote incision, forming the tunnel, and creating a pouch at the surgical site. A pouch is created at the surgical site to house and confine the graft. Preferably, the pouch is constructed having a suitable configuration that is receptive to accepting the graft, and also, will hold the graft by situating the graft received within the pouch in a desired orientation for the augmentation or restoration to properly take place. The creation of the pouch is carried out by manipulating instruments through the remote incision and the tunnel created. According to preferred embodiments, the pouch is created by manipulating the periosteum at the surgical site. Preferably, the instruments are operable from outside of the remote incision, and have portions, such as arms, that may be manipulated and which may pass through the tunnel. The instrument arm preferably has a cutting or shaping element at its end, which may be positioned and maneuvered at the surgical site. According to preferred embodiments, manipulating the periosteum is accomplished by elevating the periosteum at the surgical site to create a subperiosteal pouch which will house and confine the graft.

According to preferred embodiments, the instrumentation utilized in creating the pouch preferably is inserted into the remote incision, and moved along through the tunnel to the surgical site. The instrument may be used to form the pouch by manipulating the periosteum at the surgical site, which may involve elevating and positioning the periosteum at the site location. Preferred embodiments create a path from the incision to the surgical site that may be entirely within the soft tissue (e.g., oral mucosa and gingiva).

According to some alternate embodiments, the creation of the pouch may be carried out using an instrument that includes specially configured cutting and grasping elements, which allow cutting of the tissue and manipulation of the tissue to form a pouch. Preferably, the pouch is formed configured as an open area or hollow, which has an opening that communicates with the tunnel, which communicates with the remote incision.

Once the pouch has been created, the implantable article, such as the bone graft, is delivered to the surgical site. The instruments used to make the pouch (and tunnel) are removed to provide open access to the tunnel passageway. According to preferred embodiments of the invention, the bone graft preferably may comprise anorganic human, bovine, equine, porcine or mineral bone particles, and more preferably, may comprise an admixture of anorganic bone particles and biologic agents. These biologic agents may comprise one or more growth factors, or osteoinductive factors; and binding or adhesive agents. According to some embodiments, the biologic agent may comprise one or more of growth factors, cytostatic agents, antibiotics, radioactive materials and/or antibodies. According to some preferred embodiments, the bone graft comprises anorganic human or bovine bone, and, according to some embodiments, may comprise anorganic human or bovine bone particles, mixed with a biologic agent that contains one or more platelet derived growth factors (and/or other agents), and a binding or adhesive agent.

According to some embodiments of the invention, the bone graft may be prepared in advance of the procedure, and may be supplied in a package. Preferably, the package is sterile and packaged in conjunction with or separately from the biologic agent. In addition, the implantable article, such as a bone graft, may itself be sterilized prior to or in connection with its packaging, by applying a suitable sterilization technique that does not degrade or otherwise diminish the suitability of the bone graft. Examples of such sterilization may include UV light exposure, irradiation, and other treatments. The bone graft preferably is a pre-formed article, available in different designs and sizes, which according to some preferred embodiments is manufactured from bone or a combination of bone and collagen, or bone mixed with binding or adhesive agents. According to preferred embodiments, the bone graft is molded from non-human bone, and more preferably, may be formed from human, bovine, equine, porcine or mineral bone. The graft may be comprised of anorganic bone, which according to preferred embodiments, may be anorganic human, bovine, equine, porcine or mineral bone. According to some embodiments, the bone graft includes a biologic agent, such as, for example, a biologic agent containing platelet derived or other growth factors. According to some embodiments, the bone graft may comprise anorganic bone particles and a biologic agent, such as, for example, a biologic binding or adhesive substance, and a biologic agent containing platelet derived or other growth factors. According to some other embodiments, the bone graft is prepared at the location where the surgical procedure is being carried out, and may involve mixing together anorganic bone particles, which preferably comprise anorganic human, bovine, equine, porcine or mineral bone particles, with a biologic agent, such as, for example, a biologic agent containing platelet derived or other growth factors, and a binding or adhesive substance. According to some alternate embodiments, the bone graft is supplied as a conglomeration of anorganic particles, which may be formulated in combination with collagen or a binding or adhesive substance, and may be cut and further shaped prior to implantation. The bone graft also may be treated with a suitable treatment agent, such as, for example, a biologic growth factor agent.

According to some embodiments, the implantable articles comprising bone grafts, are xenogenic or mineral grafts that are customized for use to address the morphology of the individual. According to some embodiments, the bone graft may be formed by molding together anorganic bone particles, such as human, bovine, equine, porcine or mineral bone particles. The particles preferably may be processed to form an implantable article, such as, for example, those articles depicted in FIGS. 16-25 herein.

According to some embodiments, the articles depicted in FIGS. 16-25 preferably may be pre-milled from a suitable bone material, and preferably from equine, porcine or mineral bone, while according to other embodiments, they may be molded from bone material. Additional embodiments are disclosed in FIGS. 26-35, which illustrate further embodiments of grafts. According to some embodiments, the grafts are formed by milling, and are pre-milled articles. According to some other embodiments, the grafts are formed using bone granules or particles that are formed together with a binding or adhesive agent to a desired configuration. The bone grafts may be selected based on the defect of the individual and patient physiology to be addressed.

The anorganic bone particles preferably are processed together with a suitable substance that promotes binding or adhesion of the particles, for example collagen. Prior to adding the binding agent, the bone material may be processed by undergoing one or more extractions and/or demineralizations. For example, some processing of the anorganic human or bovine bone (or other bone) may include comminuting or dividing the bone to produce particles having different sizes (the particles may range in size, and size distributions, and may comprise granules or powders). The human, bovine, equine, porcine or mineral bone material, such as the particles or granules, preferably is mixed with a binder or adhesive which may comprise a biological substance (e.g., of biological origin). According to some alternate embodiments the binder may comprise collagen, a biodegradable polymer, and more preferably may comprise polymers or proteins of biologic origin. The treated or processed human, bovine, equine, porcine or mineral bone particles and agent mixture preferably are formed into certain predetermined shapes. This may be done by introducing the mixture into a suitable mold, and preferably, a mold that is sterilized. The mixture may be compressed within the mold to fill the mold, and the mixture permitted to cure to the mold form. The curing process may involve placing the mixture within the mold and applying compression thereto upon mixing the processed bone material with the agent.

According to some embodiments, anorganic human, bovine, equine, porcine or mineral bone material may be processed to form a particulate material, such as a powder or granular form. The processing may involve combining the bone particle material, such as, for example, the bone granules or powder form of the processed bone, together with a suitable binding or adhesive agent. The binding or adhesive agent may be added, for example, according to some embodiments, in an amount constituting from 1% to 99% of the total implantable mold. Suitable methods employed to process the bone preferably may comprise extracting free lipids, fatty acids, lipoproteins, associated with the bone stroma, as well as demineralizing and deproteinizing the bone (e.g., with an acid application or extraction). The particle size of the bone powder may vary, and according to some embodiments may be from 250 to 1000μ.

The processed bone powder, in accordance with some embodiments, may be mixed with 1 to 10 parts of a binder or adhesive. The final formed parts are then sterilized by irradiation and sealed in a sterile package.

According to some alternate embodiments, the bone graft is formed from anorganic bone or mineral particles, and includes a layer, which preferably may be collagen. According to some other embodiments, a bone graft may be milled from bone, and may be coated or provided with a layer of a substance, e.g., collagen, or other component that is designed to stimulate growth or healing.

According to some implementations, the method may include selecting a desired bone graft shape or structure, or, alternatively, may include shaping the bone graft. The bone graft may be pre-supplied in a variety of suitable shapes and sizes that may be selected for use based on the circumstances of the augmentation or reconstruction to be carried out using the minimally invasive subperiosteal tunnel in the current method.

Another preferred embodiment would include the use of implantable bone grafts constructed from xenogenic or mineral bone molds containing 1%-99% collagen or another binding or adhesive agent, and manufactured in a variety of shapes and sizes to be inserted through a remote incision and delivered through a subperiosteal tunnel to the recipient site.

According to one preferred embodiment, a kit is provided, in which a plurality of the bone or bone/collagen grafts are supplied, providing alternative options for use. According to preferred embodiments, the bone graft is supplied for use within a particular time period, and may be so designated. Suitable treatment agents may be provided so that the bone graft is pretreated, or alternately, where the bone graft is required to have a treatment contemporaneous with the implantation, the kit may supply the treatment. Alternatively, the treatment product or agent may be separately supplied or obtained.

Once the bone or bone/collagen graft has been selected or constructed (by any desired pre-implantation manipulation or by a customized formation, e.g., milling, compression, or 3D printing, used to produce the graft), the bone graft is then delivered to the surgical site. Delivery of the bone graft preferably takes place by delivering it to the surgical site through the remote incision and tunnel. According to a preferred embodiment for implementing the method, the bone graft is loaded onto or into a carrier and delivered from the remote incision to the surgical site. After delivery to the surgical site, the bone graft may be condensed and adapted to achieve the degree of bone augmentation desired. The manipulation of the bone graft at the surgical site preferably is carried out by utilizing suitable tools that allow for manipulation of the bone graft, and, according to some preferred embodiments, also allow for the removal from the surgical site of any excess or fragments of the graft that may have been excised during the procedure.

Condensing of the bone graft preferably may be carried out at the surgical site when the implantable article has been delivered to the site or pouch. Condensing preferably may be done using a condenser, such as, those condenser instruments configured according to embodiments of the invention. The condenser preferably includes a manipulatable arm with a condensing head on the end thereof. The condensing head may be used to apply pressure to the bone graft to adapt the graft to the orientation desired. The condenser preferably is maneuverable through the remote incision and the tunnel, where the maneuverable arm portion of the condenser may be manipulated to pass through the incision and the tunnel passageway. The condenser head or end preferably is maneuverable at the surgical site to manipulate the bone graft and tissue at the site. Following condensation, a surgical spatula may be utilized to adapt and mold the graft into an appropriate shape.

The implantable article preferably is transported to the surgical site, and preferably into the pouch formed. This preferably is accomplished using a carrier instrument. The carrier preferably may comprise an instrument that is designed to hold the bone graft and transport it through the incision, through the tunnel, and into the pouch that was created at the surgical site to receive the graft. The carrier preferably includes elements that hold the graft, and those elements, or additional elements, may be included as well for positioning the graft within a desired location in the pouch. The carrier preferably is sized to hold the graft, and the carried arms preferably are configured to maneuver through the tunnel with the graft in grasp, and deliver the graft to the surgical site, and preferably, into the pouch. The carrier may then be operated (outside of the incision) to release the grasp of the article (e.g., the graft). The carrier then is withdrawn from the surgical site and the tunnel. According to some alternate embodiments, a carrier instrument is configured to position the implantable article, such as, for example, the bone graft to be implanted at the surgical site, at the remote incision and insert the graft into the incision and into the tunnel passageway. According to some embodiments, the carrier instrument may release the article and one or more alternate instruments may be used to move the article to its intended destination at the surgical site. According to some other embodiments, the carried may be used to deliver the implantable article to the surgical site or pouch, and one or more other instruments may be used to further manipulate the article, e.g., to position or shape the article.

According to preferred embodiments, a single bone graft is installed at the surgical site for vertical or horizontal augmentation. However, according to some alternate embodiments, a plurality of grafts may be installed at the surgical site, and preferably within the pouch, to provide the desired shape or construction of the augmentation or reconstruction desired.

Once the graft is suitably manipulated within the pouch, the instrument or instruments are withdrawn from the surgical site (and the patient), and the incision at the remote site is closed off, which preferably may be done by any suitable closing means, such as for example, suturing. Prior to suturing, the tunnel or other tissue affected by the procedure may be treated with an anesthetic, cleaner or sanitizing agent.

The method may be implemented to provide augmentation and/or restoration of bone in the mandibular and maxillary areas of an individual. The method may be carried out by producing a tunnel that is oriented in a suitable direction to facilitate positioning and alignment of the graft. For example, where the structure or augmentation site being addressed is vertical in nature, additional incision designs may be utilized to create a vertical tunnel. Alternatively, a vertical tunnel may be produced to provide a suitable passageway from the remote incision to the surgical site, regardless of the orientation of the surgical site, or pouch to be created. For example, a vertical or substantially vertical tunnel may be developed for a graft that is to be vertically oriented in a substantially vertical installation tunnel leading to the site, but which may be oriented in a position other than vertical (e.g., horizontal), at the installation site.

According to some preferred embodiments, devices comprising instruments for carrying out the method are provided. According to one embodiment, an elevation device or elevator is provided to elevate the periosteum at the surgical site to create the pouch. According to some embodiments, the elevator may be configured with a handle and a maneuverable arm with an elevating element thereon. According to some embodiments, the elevator may be configured as a subperiosteal instrument, with a lumen or wire for inserting the elevator through the tunnel, and manipulating the tissue, such as the periosteum, at the surgical site where the graft is to be installed. Some elevators, according to the invention, may include ends that are suitably operable (remotely from the surgical site, and from outside of the incision) to expand or separate and cause elevation of the tissue.

Another instrument that may be used in conjunction with the method and implantable articles is a subperiosteal syringe. The subperiosteal syringe may be configured to apply material to the incision, tunnel or surgical site. Some embodiments of the syringe may be configured with an end that may be placed at the remote incision and be moved or manipulated to incise the tissue to facilitate formation or form a tunnel within the tissue. According to some embodiments, the subperiosteal syringe may have a configuration to facilitate insertion through the tunnel and to distribute its contents in a particular direction. For example, the syringe may comprise a specially configured device that has a maneuverable lumen end for manipulating the syringe end through the tunnel passageway and to position the end for delivery of material from the syringe body to desired locations in the pouch or graft site.

Further devices are provided and may include a condenser for manipulating the graft. The condenser may be used for condensing and may comprise a specially configured instrument, which, according to preferred embodiments, is provided having a holding area and at least one end (or alternatively, a double end), on which a condensing element is provided. The condensing element preferably is connected to the holding area with a maneuverable arm. The condenser is configured so that its arm and condensing element are maneuverable. Preferably, the condenser may be manipulated from outside of the incision and maneuvered through the tunnel and may be used to condense or shape the article at the surgical site. The condenser may be utilized to pack the bone graft into the defect to be treated, so that it may optimize its density and ensure its location in the appropriate site. The tips of the condenser may also be designed to facilitate the placement and packing of the implantable bone graft materials to cover exposed tooth root surfaces or exposed dental implant surfaces, for the purposes of regenerating the biologic mechanism whereby these exposed dental root or dental implant surfaces are attached to the grafted area of the jawbone. In another preferred embodiment, the condenser tips may be designed to optimize placing and packing the bone graft material into the interdental area, therefore helping to re-create and support gingival papillae. In addition, according to some alternate embodiments, the condenser may be configured to comprise a lumen and have a maneuverable condensing element, which may be disposed at the lumen end. The lumen preferably is maneuverable and may be directed through a tunnel created in the tissue leading to the graft. The condenser end may be operated through the maneuvering of the lumen to engage the bone graft and tissue at the surgical site. Preferably, the operation of the condenser end may be carried out from outside of the surgical site and incision.

The bone graft may be referred to as a block or mold, and a device, such as a carrier or holder, preferably is provided for holding the graft (mold or block) to secure the graft and maneuver the graft through the passageway or tunnel leading to the surgical site, and into the pouch created at the site. The device preferably is configured with a holding mechanism, which may comprise a holding element such as, for example, a tab or arm, which may clamp or otherwise hold the graft or block while it is being transported from the remote incision to the pouch, and while it is maneuvered into position within the pouch. The holding element preferably is releasable to release the graft or block, once it has been suitably positioned within the pouch. According to some preferred embodiments, the holding mechanism may be actuated to re-grasp a graft or block, when repositioning is desired. The holding device preferably is configured as a maneuverable device, which may be constructed having a lumen or other maneuverable lead that is insertable through the incision, tunnel, and at the surgical site, and includes one or more operable actuators for controlling the grasping and releasing of the graft or block. The tips of the holding device may incorporate Teflon, or other suitable and autoclavable plastic materials, that will allow firmly grasping the bone block or mold, while minimizing the potential for damage.

Preferred exemplary embodiments of instruments for carrying out the method are depicted in figures attached hereto.

Figure 1D:
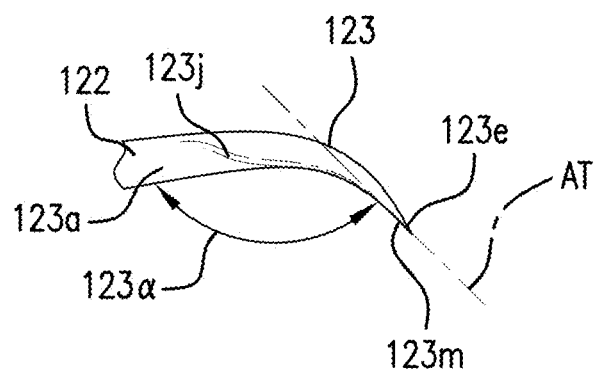
FIG. 1D is an enlarged partial view of the device of FIG. 1A, shown rotated about 90 degrees from the position in FIG. 1B.

FIGS. 1A-1D are views of an exemplary embodiment of an elevator 111 according to the invention, FIG. 1A showing a top plan view, FIG. 1B showing a side elevation view, and FIGS. 1C and 1D showing respective end views of the element of the respective instrument end.

Referring to FIGS. 1A to 1D, what is illustrated is a device comprising a dental surgical instrument 110 for use in carrying out a subperiosteal augmentation or reconstruction procedure involving the creation of an incision, insertion of the instrument 110 through an incision remotely situated from a surgical site where bone is to be implanted, and the maneuvering of the instrument 110 through the tissue to develop a tunnel within the periosteum that leads to the surgical site. The instrument 110 includes cutting edges provided on the tip 113, and may be used to prepare the surgical site to receive bone graft material.

The dental instrument 110 is shown configured as an elevator. The dental instrument 110 includes a handle 111, an elongate shank 112 connected to the handle 111 at the proximal end 112a of the shank 112 and being shown extending from the barrel shaped handle body 111a. A tip 113 is provided at the distal end 112e of the elongate shank 112. The handle 111 may be provided with a surface treatment or structure to facilitate holding and grasping of the instrument, some examples of which include knurlings, flutings or other elements to enhance gripping of the instrument. In the exemplary embodiment illustrated, the device 110 is shown having a knurled surface structure, such as the bands 114, provided on the exterior of the cylindrical or barrel shaped handle body 111a to facilitate holding and grasping the instrument 110 (e.g., from a package, tray and/or during use). The barrel shaped handle body 111a includes a reduced diameter portion 111b provided at the handle end where the shank 112 is shown connecting with the handle 111. According to some embodiments, the shank 112 preferably may be elongated to span inside the handle 111, and preferably is secured within the handle 111. According to some embodiments, the shank 112 may be coextensive with a portion of the handle 111, or all of the handle 111, and according to embodiments, may span through the handle 111 to provide a second shank 122 extending from the opposite side of the handle 111. For example, the first shank 112 and second shank 122 may be separate, or may be formed from a single elongated structure. According to some alternate embodiments, the first shank 112 or the second shank 122, or both, may be formed with the handle 111, as a single piece. Alternatively, the instrument 110, although shown having a shank 112, 122 at each end thereof, may be constructed with a single shank (112, or 122), and may be provided as two separate instruments.

The shank 112 has a larger diameter portion 112a closest to where the shank 112 joins the handle 111. The shank diameter is shown tapering to a smaller diameter 112b, moving from the handle 111 to the distal end of the shank 112 where the tip 113 is located. The tip 113 is provided on the distal end 112e of the shank 112 and is shown at the end of the shank shaft 112c. Referring to FIG. 1B, as seen from the side view, the shank 112 has a slight gentle curvature 112d to the shank shaft 112c. As shown in the exemplary embodiment of the instrument 110, the shank shaft 112c is free from sharp angles.

In the instrument embodiment illustrated in FIGS. 1A-1D, the first tip 113 at the shank distal end 112e is shown having a triangular shape. The tip 113 extends at an angle to the central axis A of the shank shaft 112c, as shown in the side view in FIG. 1B. Preferably, the angular disposition of the tip relative to the shank shaft 112c central axis A is from about 20 to 70 degrees, and more preferably from between about 40 to 60 degrees. The tip preferably has a concave or flat bottom surface 113a (FIG. 1B) and has a convex top surface 113b (FIG. 1A). According to some preferred embodiments, the shank shaft 112c, as shown in the side view of FIG. 1B, curves above the central axis A and returns below the central axis A. Preferably the tip 113 is provided to reside below the central axis A when the device 110 is oriented as shown in the side view of FIG. 1B. The tip 113 is configured with curved edges, which preferably are sharp along the perimeter and comprise a cutting edge or curved cutting periphery designed to be used for cutting when manipulating the tool (through tissue or into bone). The tip 113 has a proximal edge 113f that meets the distal end 112e of the shank shaft 112c, which preferably may be rounded and smooth. According to a preferred configuration, the top plan view of FIG. 1A shows the tip tapering from a narrow width where the tip joins the shank shaft 112c, widening toward a location 113d just before the tip end 113e. According to some preferred embodiments, the widest portion of the tip 113 is located about two thirds of the distance from the start of the tip 113 to the tip end 113e, which in the embodiment illustrated is represented by the tip location 113d. The tip 113 is shown having a preferred shape which is triangular, and preferably a rounded or curved triangle, such as a tear drop shape.

The shank 112 preferably is provided having a suitable length that provides sufficient penetration depth to pass through a subperiosteal tunnel and reach the intended surgical site. According to some preferred embodiments, the shank 112 may have lengths between about 30 to 85 mm, and more preferably from between about 35 to about 65 mm. According to an exemplary embodiment, the instrument 110 may be configured having a shank radial dimension from about 1 mm to about 2 mm, with the large diameter shank portion (112a) being about 3 to 8 mm in diameter, and the narrower shank portion (112b) diameter, where the shank shaft 112c joins with the tip 113, being about 1 to 5 mm, and preferably about 2.5 mm. The bottom tip surface concavity 113a preferably has a radius of curvature and the upper or convex top surface 113b preferably has a radius of curvature, examples of which are illustrated in the exemplary embodiment shown in FIGS. 1A-1D.

Although the instrument 110 may be constructed with a shank 112 having a length suitable to reach the intended surgical site through the incision and the length of the tunnel, according to some embodiments, the shank 112 may be from about 30 to 60 mm. The instrument 110 may be constructed in different sizes to provide shank lengths that are longer or shorter. The medical personnel user may select an instrument based on the length required for the procedure. Referring to FIGS. 1A and 1B, the shank 112 may be provided having a length of from about 30 to 60 mm, and according to one preferred embodiment, the shank length is about 35 mm. The tip 113 preferably may be provided with a suitable diameter or width for use, and according to a preferred embodiment, may have a width at its widest dimension to be about 4.5 mm.

The outer surface of the shank 112 preferably may include a series of evenly spaced markings which may be visibly provided thereon to mark the depth from the tip end 113e to the marking indicia of the shank 112, so as to provide a depth indication to the user when the instrument 110 is inserted in a subperiosteal tunnel, as to the instrument penetration depth.

The elevator instrument 110 preferably provides the specially configured tip 113 at its leading end for elevating the mucosal tissue along the incision, which preferably involves elevating the mucosal tissue along the tunnel leading to the surgical site or pouch, the tunnel being the pathway through which the bone graft material will be delivered to the surgical site (which is the pouch to receive the bone graft material). The tip may be presented to the tissue to form an incision using the sharp peripheral tip edge. The instrument tip 113 may be further guided through the tissue by the user, so that the instrument 110 is moved along with the tip and shank entering the tissue, and elevating the tissue as the user maneuvers and manipulates the instrument to form a tunnel in the periosteum.

As shown in the figures, the tip 113 preferably is offset from the instrument 110 central axis A (see FIG. 1B) to facilitate elevation of the mucosal tissue bordering the tunnel. The shank 112 preferably is smooth and has rounded edges, and may be cylindrical or radial in configuration so as to further facilitate insertion and maneuvering of the shank 112 through the mucosal tissue.

According to preferred embodiments, the shank 112 may be configured having a larger cross-sectional diameter at the shank 112 proximal end 112a (the shank portion nearest to the handle 111), which may taper or narrow over the length of the shank 112 to the tip 113, or, alternatively, which may taper to a location along the shank 112, proximal from the tip 113.

According to preferred embodiments, the instruments may be constructed with two usable ends. The instrument 110 shown in the exemplary embodiment includes a second shank 122 provided at the instrument end opposite the first shank 112. The second shank 122 has a tip 123, and in the embodiment illustrated, has a configuration that is different from the first tip 113 on the opposite end. The second tip 123 may be formed on the end of the second shank 122, and the second shank 122 may be the same as the first shank 112 in terms of dimensions and configurations, or, may be different. Preferably, the second shank 122 is configured to have suitable dimensions, like the first shank 112, so as to be useful to develop a tunnel within the periosteum and maneuver therein. In the exemplary embodiment depicted, the second shank 122 extends from the barrel shaped handle body 111a in the direction opposite the extension of the first shank 112. The tip 123 is provided at the distal end of the elongate second shank 122. The second shank 122, similar to the first shank 112, is shown having a larger diameter portion 122a closest to where the second shank 122 joins the handle 111, preferably, at the handle second reduced diameter portion 111c (provided at the handle end opposite the first reduced diameter portion 111b). The diameter of the second shank 122 is shown tapering to a smaller diameter 122b, moving from the handle 111 to the distal end of the shank 122 where the tip 123 is located. The tip 123 is provided on the shank distal end 122e and is shown at the end of the shank shaft 122c. Referring to FIG. 1B, as seen from the side view, the second shank 122 is provided with a slight gentle curvature 122d to the shank shaft 122c, and, preferably, is free from sharp angles.

In the embodiment illustrated, the second tip 123 at the second end of the handle 111 is shown configured as a fan shape, where the proximal tip portion 123a joining with the shank shaft 122b is configured as a narrower portion, and, from that point distally, the tip 123 widens, fanning out, so that the wider portion of the tip 123 is located at a point along the tip axis that is between the distal end of the tip 123e and the proximal end 123a that joins with the shank 122. As shown best in FIG. 1C, the second tip 123 has a proximal tip portion 123b and a distal tip portion 123c. For example, the enlarged view of the tip 123 is shown in FIG. 1C, and illustrates the tip having a wide portion formed by a diameter, and a leading portion or distal portion 123c with an arcuate profile 123f. The arcuate profile 123f comprises a sharp edge 123g for cutting (e.g., soft and hard tissue, and bone) which, in the exemplary embodiment illustrated, may be defined by a radius. For example, according to some preferred embodiments, the diameter may form a width of the fan shaped tip 123, and may form the widest point, and the leading or distal portion 123c may be formed as a divergent body, such as for example, having a semi-circular, arcuate, curved partial oval, or partial elliptical shape, and in particular, having a periphery of such a shape. The proximal portion 123b of the tip 123, located between the wide width (where, in the embodiment illustrated, edges 123i, 123k are located) and the shank 122, preferably may be inwardly tapered, and preferably may be configured with inwardly directed curved edges, such as the curved edges 123i, 123j, which are concave relative to a central axis of the tip 123. Referring to FIG. 1D, the tip 123 also is illustrated having a preferred bend or angle 123α, which preferably is relative to the central axis A of the portion of the shank 122c to which the tip 123 joins. The angle 123α is formed by the central axis A of the shank portion 122c and the central axis of the tip AT, and is shown measured relative to the upper surface 123m. Preferably, the angle 123α is less than 180 degrees, and more preferably is between about 120 to 170 degrees. The tip 123 provides the instrument 110 with the capability to cut through tissue and bone by maneuvering the instrument 110, via manipulation of the handle 111 (e.g., forward, axially right or left, or angularly). The instrument 110, for example, may be used to construct a tunnel in the mucosal tissue that leads to the surgical site within the periosteum where implantable bone graft material will be deposited. The instrument tip 123 facilitates moving the instrument 110 in a forward direction to move the shank forward in the structure, such as tissue, and directing the tunnel formation along a desired path, which may be linear or non-linear. For example, the instrument 110 may be used to develop a tunnel within the periosteum of the tissue, and the divergent end of the tip 123 is configured to elevate the tunnel when forming the tunnel so as to facilitate directing the location where the tunnel will be developed. The instrument tip 123 also includes edges 123k, 123l on opposite ends where the arcuate fan like portion 123f, or distal portion of the tip 123, meets with the proximal arcuate portions 123i, 123j, respectively. The edges 123k, 123l facilitate manipulations of the instrument 110 to direct cutting in a desired path, such as occlusal or lingual direction. The edges 123k, 123l preferably may be sharp corners, or alternately may be curved edges, and sharp corners, or alternative curved edges, may be provided with a cutting periphery. The proximal arcuate portions 123i, 123j, respectively, preferably are not required but could be provided with a cutting periphery. For example, the instrument 110 may be used to develop a tunnel in the mucosal tissue that may be directed along a non-linear path. According to a preferred embodiment, the tip 123 has an upper surface 123m and a lower surface 123n. As shown in the exemplary embodiment, the upper surface 123m may be concave, and the lower surface 123n may be flat or preferably may be convex.

As discussed above in connection with the first shank 112, the second shank 122 may have a similar dimension or length. For example, embodiments of the instrument 110 may provide the second shank 122 having a length of from about 30 to 60 mm. According to one preferred embodiment, the shank length may be about 35 mm. The tip 123 preferably may be provided with a suitable diameter or width for use, and according to a preferred embodiment, may have a width at its widest dimension, where the fan is spread out, to be about 4.5 mm. According to some embodiments, the instrument 110 may be constructed with different tips, such as the first end tip 113 and second end tip 123 shown in the instrument 110. The tips also may be provided having the same width dimension at their widest point, such as the 4.5 mm dimension, referenced in an exemplary embodiment for the triangle or tapered first tip 113 and for the fan shaped second tip 123.

According to an alternate embodiment, as illustrated in FIGS. 2A-2B, an embodiment of an elevator instrument 210 is shown. The elevator instrument 210, in the exemplary embodiment, is similar to the instrument 110 of FIGS. 1A and 1B, except that the shank 212 is longer, and has a longer shank shaft 212c. The shank shaft 212c on the first end of the instrument 210 is longer in relation to the embodiment depicted in FIGS. 1A and 1B, so as to position the tip 213 distally further from the handle 111. According to some embodiments, the length of the shank 212 may be provided from between about 40 to 80 mm, and in an exemplary embodiment, the length of the shank 212 may be about 45 mm. The second end of the instrument 210 includes a second shank 222, which is longer than the second shank 122 of the instrument 110 shown in FIGS. 1A and 1B. The second shank 222 also may be provided having a dimension similar to the first shank 212. The embodiment of the instrument 210 is shown having shanks 212, 222 of equal length. The second end of the instrument 210 includes shank 222 that is comprised of a shank shaft 222c provided with a tip 223 at the distal end. The tip 223 is configured as a fan shape, where the proximal tip portion 223b joining with the shank shaft 222 at the proximal tip end 223a is configured as a narrower portion, and, from that point distally, the tip 223 is shown widening and fanning out, so that the wider portion of the tip 223 is the tip distal portion 223c.

The first tip 213 of the instrument 210 is shown configured having a triangular shape, being wider at the tip proximal portion 213b where the tip 213 joins the shaft 212. The tip 213 tapers and is shown converging from the proximal end 213a toward the distal portion 213c, where the tip 213e is provided having a point. According to preferred embodiments, the lateral edges 213f, 213g are sharp cutting edges that may be used to cut through soft and hard tissue as well as bone. As shown in the side view of FIG. 1B, the first tip 213 preferably is angularly bent relative to the central axis A of the first shaft 212c. In the embodiment illustrated, the first tip 213 is shown being angularly disposed relative to the shank second portion 212c", and away from the central axis A. The second shank portion 212c" is itself shown being angularly disposed relative to the first shank portion 212c', and bent away from the central axis A. According to a preferred embodiment, the shank first portion 212c' and second shank portion 212c" and bend 212d may lie in the same axial plane. The second tip 223 also may be provided with a bend 222d, similar to the bend 212d, which may be provided along the central axis A, with the shank first portion 222c' and shank second portion 222c" forming an angular relation at the bend 222d.

Referring to FIGS. 3A and 3B, an alternate embodiment of an elevator instrument 310 according to the invention is illustrated. The instrument 310 preferably is constructed having a handle 311, with a handle body 311a and a reduced diameter portion 311b, 311c, at each end thereof. The first shank 312 is shown extending from the handle body, which in this embodiment is from the handle tapered portion 311b, and terminating in a tip 313. The shank 312 is provided having two bends, including a first bend 312d, which in the top view of FIG. 3A turns to the left of, or away from, the central axis A, and a second bend 312e that bends back toward the axis A, to the right. According to a preferred embodiment, as depicted in the side view of FIG. 3B, the first shank 312, and second shank 322 have bends that lie within a plane. For example, according to an exemplary embodiment illustrated, the first bend 312d and second bend 312e bend to the left or right of the axis A (relative to the top view of FIG. 3A), but remain in the same axial plane.

The first tip 313 and second tip 323, in the instrument 310, preferably are mirror images of each other. The tip 313 is illustrated having an elliptical configuration. Preferably, the elliptical tip 313 has an elliptical length that is greater than the elliptical width, with the elliptical length spanning in the same direction as the axis of the shank shaft 312c to which the tip 313 is connected. The elliptical width of the tip 313 preferably is the widest width of the tip taken perpendicular to the shank shaft 313c. According to some embodiments, the elliptical tip 313 may form a tapered portion at its proximal end where it joins with the shank second portion 312c". The instrument 310 is configured with a second end having a second tip 323 provided at the end of the second shaft 322. The second shaft 322 is shown extending from the handle body 311a and in particular from a tapered end portion 311c. The bends in the shank 312 preferably are provided as discussed and shown in connection with the first shank 312. A first bend 322d and second bend 322e are provided, but with mirrored orientation relative to the bends of the first shank 312. The shank shaft 322c moves axially away and to the right (looking from the top view in FIG. 3A) of the axis A, and, at the second bend 322e, the shank shaft 322c moves toward the axis A, toward the left, and crosses the axis A, and then terminates at the tip 323. An elliptical tip 323 is provided at the distal end of the shank shaft 322c. According to a preferred embodiment, the second tip 323 is the same as the first tip 313, and preferably is an elliptical tip. According to some embodiments, the first tip 313 and second tip 323 are mirror images of each other. The first tip 313 is shown having a concave surface 313a on one side thereof, and preferably, has a flat surface or convex surface 313b (FIG. 3B) on the other side. The second tip 323 is shown having a flat or convex surface 323b on one side thereof, and preferably, has a concave surface on the other side 323a. According to preferred embodiments, the first bend 312d and second bend 312e form two portions of the shank shaft 312c, including a first portion 312c' and a second portion 312c". The first portion 312c' is shown shorter than the second portion 312c". According to preferred embodiments, the shank 312 at the first bend 312d is angled away from the central instrument axis A, represented by angle alpha, 310α. The shank first portion 312c' meets the shank second portion 312c" at the second bend 312e, and the shank second portion 313c" bends inwardly toward the central axis A, relative to the first portion 312c', at an angle represented by angle beta, 310β. According to a preferred embodiment, the first angle, angle alpha, 310α, that the first portion 312c' makes with the axis A is relatively smaller than the angle beta, 310β, that the first portion 312c' makes with the second portion 312c". According to a preferred embodiment, the first angle alpha (310α) is about 30 degrees, whereas the second angle beta (310β) is about 120 degrees. The angular ratio between the first angle alpha (310α) and second angle beta (310β) preferably may be about 1:4. As illustrated in FIGS. 3A and 3B, the second shaft 322 preferably is provided with angular bends similar to the bends described in connection with the first shaft 312, which preferably may be provided with similar angular relationships.

According to a preferred embodiment, an elevator 310 is constructed with the portion of the shank shaft 312c between the first bend 312d and second bend 312e being about 14 mm, and with the portion between the second bend 312e to the tip 313, and inclusive of the tip length, being about 22 mm. Similarly, the second shank 322c may be constructed with similar dimensions. Each elliptical tip 313, 323, preferably is about 5.5 mm in length, and has a width of about 4 mm.

According to alternate embodiments, the instrument 310 may be configured with a fan like tip, such as, the fan tips shown and described herein, including, for example, the tip 123 shown and described in connection with FIGS. 1A-1D. The instrument 310 may be configured with the bends and shank provided with a fan like tip at one or both ends.

An alternate embodiment of an elevator 410 is shown in FIGS. 4A and 4B. The elevator 410 is similar to the elevator to the instrument 310 of FIGS. 3A and 3B, except that each shank 312, 323 is longer, and the angles of the shank bends, the first angle alpha (410α) and second angle beta (410β) in the instrument 410 are provided to produce less of a bend. The first angle alpha (410α) of the instrument 410 is less than the corresponding angle (410α) of the instrument 310. The second angle beta (410β) of the instrument 410 is greater than the second angle beta (410β) of the instrument 310. The shank shaft first portion 412c' on the first end of the instrument 410 is longer in relation to the shank shaft first portion 312c' in the instrument 310 depicted in FIGS. 3A and 3B, as is the second shank portion 412c" which is longer than the corresponding shank second portion 312c" of the instrument 310. In the longer instrument 410, the tip 413 is distally further from the handle 411. The shank 412 is constructed to have less pronounced angular bends at the first bend 412d and second bend 412e so as to provide a maximum instrument width that includes deviations from the central axis A, on either side. According to some embodiments, the axial width or window for the instrument 310 may be the same window as for the instrument 410, with the additional shank length being accommodated by a reduction in the outward deviation of the shaft relative to the central axis A. The second instrument end includes a second tip 423 provided at the end of the second shaft 422. The second shaft 422 extends from the handle 411, and preferably from the tapered portion 411c and to where it joins the tip 423 at the distal shank end. Similar to the first shaft portion 412c' and shank second portion 412c" of the first shaft 412, the second shank shaft 422 includes a shaft first portion 422c' and shaft second portion 422c".

According to a preferred embodiment, the elevator 410 is constructed with the portion of the shank shaft 412c between the first bend 412d and second bend 412e being about 19 mm, and with the portion between the second bend 412e to the tip 413, inclusive of the tip length, being about 27 mm. Similarly, the second shank 422c may be constructed with similar dimensions. In a preferred embodiment, each elliptical tip 413, 423, preferably, is about 5.5 mm in length, and has a width of about 4 mm.

According to alternate embodiments, the instrument 410 may be configured with a fan like tip, such as, the fan tips shown and described herein, including, for example, the tip 123 shown and described in connection with FIGS. 1A-1D. The instrument 410 may be configured with the bends and shank provided with a fan like tip at one or both ends.

Referring to FIGS. 5A and 5B, an alternate embodiment of an elevator instrument 510 for use in subperiosteal augmentation procedures is shown. The instrument 510 includes a handle 511, a shank 512 extending from the handle 511, with a tip 513 at the end of the shaft 512. The shank 512 includes a plurality of shank shaft portions, which in the embodiment depicted are first through fourth shank shaft portions 512c', 512c", 512c''' and 512c'''', respectively. The shank 512 includes a plurality of bends, which from the proximal shank end to the distal shank end where the tip 513 is located, are depicted as a first bend 512d, a second bend 512e, and a third bend 512f. The first bend 512d and second bend 512e are on the same axis, which is in a plane parallel to the central axis A. The third bend 512f is provided transverse to the central axis A. Preferably, the third or distal bend 512f is provided on a transverse axis, the transverse axis being represented by axis A2. The first shank first portion 512c' is provided coaxial with the central axis A. The shank second portion 512c" bends relative to the shank first portion 512c' at the first bend 512d, and is in the same axial plane as the shank first portion 512c'. The shank third portion 512c''' bends relative to the shank second portion 512c" at the second bend 512e, and then joins the shank fourth portion 512c'''' at the third bend 512f. At the third bend 512f, however, the shank fourth portion 512c'''' bends relative to the shank third portion 512c''' in a different axial plane than the shank first portion 512c', shank second portion 512c" and shank third portion 512c''' and the respective first and second bends 512d, 512e. The instrument 510 is shown having a tip 513 that is configured similar to the fan like second tip 223 shown and described in connection with the instrument 210. According to a preferred embodiment, the fan like tip 513 has an inner surface 513a that is concave. The tip 513 may be constructed as described and shown in relation to the tip 223. In the instrument 510 depicted, the concave surface 513a preferably is substantially almost parallel to the handle 511. According to a preferred embodiment, the second end includes a second shank 522, which includes first through fourth shank portions 522c', 522c", 522c''' and 522c'''', respectively, and respective bends 522d, 522e and 522f, similar to the arrangement of bends and shank portions shown in the first end of the instrument 510. A tip 523 is provided at the distal end of the shank 522. The tips 513 and 523, are depicted being constructed similar to the second tip 223 of the instrument 210 shown in FIGS. 2A and 2B, but are oriented as shown in FIG. 5A, 5B. The angular bend of the fourth portion 512c'''' orients the tip 513 in a preferred direction for utilization during the subperiosteal augmentation and reconstruction procedures. The tip 523 is configured as a fan shape, where the tip proximal portion 523b joining with the shank shaft 522 at the proximal tip end 523a is configured as a narrower portion, and, from that point distally, the tip 523 widens and fans out over the wider tip distal portion 523c. The tip end 523e preferably has a cutting edge or periphery, similar to the tip 223 of the instrument 210.

According to embodiments, the instrument 510 preferably is constructed with preferred angular dimensions, including a first angle defining a first bend 512d, which is a bend between the first portion 512c' and the second portion 512c", and a second angle defining a second bend 512e which is the bend between the second portion 512c" and the third portion 512c''', and a third angle defining a third bend 512f which is the bend between the third portion 512c''' and the fourth portion 512c''''.

According to a preferred embodiment, the instrument 510 preferably is constructed with the fourth portion 512c'''' being longer than each of the other three portions (512c', 512c" and 512c'''). The first portion 512c', second portion 512c" and third portion 512c''', may each have similar lengths. For purposes of describing the length of the first portion 512c', the tapered portion 511c of the handle 511 is included in this measurement portion. According to a preferred embodiment, the first, second and third shank portions 512c', 512c'', and 512c''', respectively, are each about 10 mm in length. The fourth portion 512c'''' inclusive of the tip 513 preferably is about 20 mm. The tip 513 preferably has a length of about 4.5 mm.

Figure 6C:
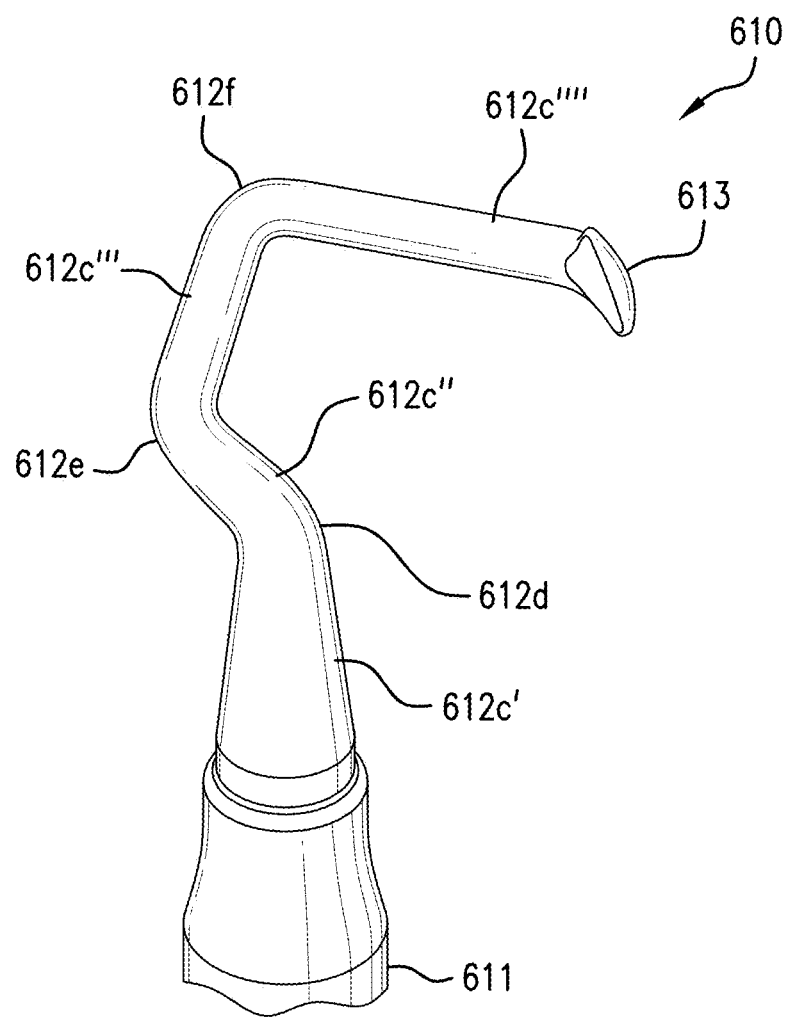
FIG. 6C is an enlarged partial view showing the shank end and tip of the device of FIG. 6A.

Referring to FIGS. 6A and 6B, an alternate embodiment of an elevator instrument 610 is shown. The instrument 610 is similar to the instrument 510, except that the first shank portion 612c' is longer than the second and third shank portions, 612c'' and 612c''', respectively, providing an extended reach of the instrument to develop a longer subperiosteal tunnel or to extend the reach within a subperiosteal tunnel. According to a preferred embodiment, the first shank portion 612c' may be about 20 to 40 percent longer than the length of the respective second and third shank portions 612c'' and 612c'''. According to a preferred embodiment, the length of the second, third and fourth shank portion, respectively, 612c'', 612c''', and 612c'''', are similar to dimensions discussed in connection with the instrument 510, with the first portion 612c' being provided having a length of about 14 mm. Alternatively, the second portion 612c'' may be provided having a greater length, and, according to a preferred embodiment, may be about 12 mm in the example depicted in FIGS. 6A and 6B, where the first portion 612c' is about 14 mm, the third portion 612c''' is about 10 mm and the fourth portion 612c'''' including the tip 613 is about 20 mm.

Referring to FIGS. 7A and 7B, an alternate embodiment of an elevator instrument 710 for use in subperiosteal augmentation procedures is shown. The instrument 710 includes a handle 711, a shaft 712 extending from the handle 711, with a tip 713 at the end of the shaft 712. The shaft 712 includes a plurality of shank sections, which in the embodiment depicted are first through fourth shank portions 712c', 712c'', 712c''', 712c'''', and 712c''''', respectively. The shank 712 includes a plurality of bends, which from the proximal shank end to the distal shank end where the tip 713 is located, are depicted as a first bend 712d, a second bend 712e, and a third bend 712f, and a fourth bend 712g. The first bend 712d and second bend 712e are on the same axis, which are in a plane parallel to the central axis A. The third bend 712f is provided transverse to the central axis A. Preferably, the third or distal bend 712f is provided on a transverse axis, the transverse axis being represented by axis A2. The first shank portion 712c' is provided coaxial with the central axis A. The second shank portion 712c'' bends relative to the first portion 712c' at the first bend 712d, and is in the same axial plane as the first portion 712c'. The third shank portion 712c''' bends relative to the second shank portion 712c'' at the second bend 712e, and then joins the fourth shank portion 712c'''' at the third bend 712f. At the third bend 712f, however, the fourth portion 712c'''' bends relative to the third portion 712c''' in a different axial plane than the first portion 712c', second portion 712c'' and third portion 712c''' and the respective first and second bends 712d, 712e. The fifth shank portion 712c''''' bends relative to the fourth shank portion 712c'''', at the fourth bend 712g. The fifth shank portion 712c''''' bends at the fourth bend 712g relative to the fourth shank section 712c''''. The relative bend is along angle Z represented in FIG. 7B, between the fourth shank portion 712c'''' and the fifth shank portion 712c'''''. As illustrated in the top view of FIG. 7A, the fourth shank portion 712c'''' and the fifth shank portion 712c''''' may have shaft segments that are coplanar, although other shaft segments may bend making at least some of the respective lengths of the fourth shank portions 712c'''' and the fifth shank portion 712c''''' in different planes. The bend of the third portion 712c''' which is on a transverse axis A2, is shown in FIG. 7B represented by the angular bend where the third portion 712c''' makes an angle Y relative to the second portion 712c'' and the central axis A.

The instrument 710 is shown with a tip 713 at the end of the fifth shank portion 712c'''''. The tip preferably is configured to provide an engaging structure for engaging one or more of the tissue or the bone graft material. According to the exemplary embodiment shown, the tip 713 is configured in a fan like configuration, similar to the tip 513, having an inner surface 713a that is concave. The concave surface 713a preferably is substantially almost parallel to the handle 711. The back of the surface 713b may be convex or flat.

According to a preferred embodiment, the second end includes a second shank 722, which includes first through fifth shank portion 722c', 722c'', 722c''', 722c'''' and 722c''''', respectively, and respective bends 722d, 722e, 722f and 722g, similar to the arrangement of bends and shank sections shown in the first end of the instrument 710. A tip 723 is provided at the distal end of the shank 722. The tips 713 and 723, are depicted similar to the tip 523 of FIGS. 2A and 2B, but are oriented as shown in FIGS. 7A and 7B. The angular bend of the fifth portion 712c''''' orients the tip 713 is a preferred direction for utilization during the subperiosteal augmentation and reconstruction procedures. The tip 723 is configured as a fan shape, where the tip portion 723a joining with the shank shaft 722 at the proximal tip end is configured as a narrower portion, and, from that point distally, the tip 723 widens and fans out so that the wider portion of the tip 723 is at the tip end 723e.

According to embodiments, the instrument 710 preferably is constructed with preferred angular dimensions, including a first angle defining a first bend, which is a bend between the first portion 712c' and the second portion 712c'', and a second angle defining a second bend which is the bend between the second portion 712c'' and the third portion 712c''', and a third angle defining a third bend which is the bend between the third portion 712c''' and the fourth portion 712c'''', and a fourth angle defining a fourth bend which is the bend between the fourth portion 712c'''' and the fifth portion 712c'''''.

According to a preferred embodiment, the instrument 710 preferably is constructed with the fifth portion 712c''''' being longer than each of the other four portions (712c', 712c'', 712c''' and 712c''''). The first portion 712c', second portion 712c'', third portion 712c''', and fourth portion 712c' '', may each have similar lengths. For purposes of describing the length of the first portion 712c', the tapered portion 711b of the handle 711 is included in this measurement portion. According to a preferred embodiment, the first, second, third and fourth shank portions 712c', 712c'', 712c''' and 712c'''', respectively, are each about 10 mm in length. According to a preferred embodiment, the fourth portion may be slightly longer than the first, second or third portions (such as 12 mm for the fourth portion length and 10 mm for each of the first, second and third portion lengths). The fifth portion 712c'''' inclusive of the tip 713 preferably is about 20 mm. The tip 713 preferably has a length of about 4.5 mm. The fifth portion 712c''''', may extend in a longitudinal direction relative to the fourth portion 712c'''' (as shown by the portion of the fifth portion 712c''''' in FIG. 7A between the fourth portion 712c'''' and the tip 713), so that about 40 percent of the fifth shank portion 712c''''' is radially outward relative to (or beyond) the relatively axial outward reach of the fourth shank portion 712c''''. For example, the fifth shank portion 712c"" shown in FIG. 7B may be about 20 mm, whereas, the portion of the fifth shank portion 712c"" shown in FIG. 7A represents about 8 mm of that portion.

Figures 8A, 8B:
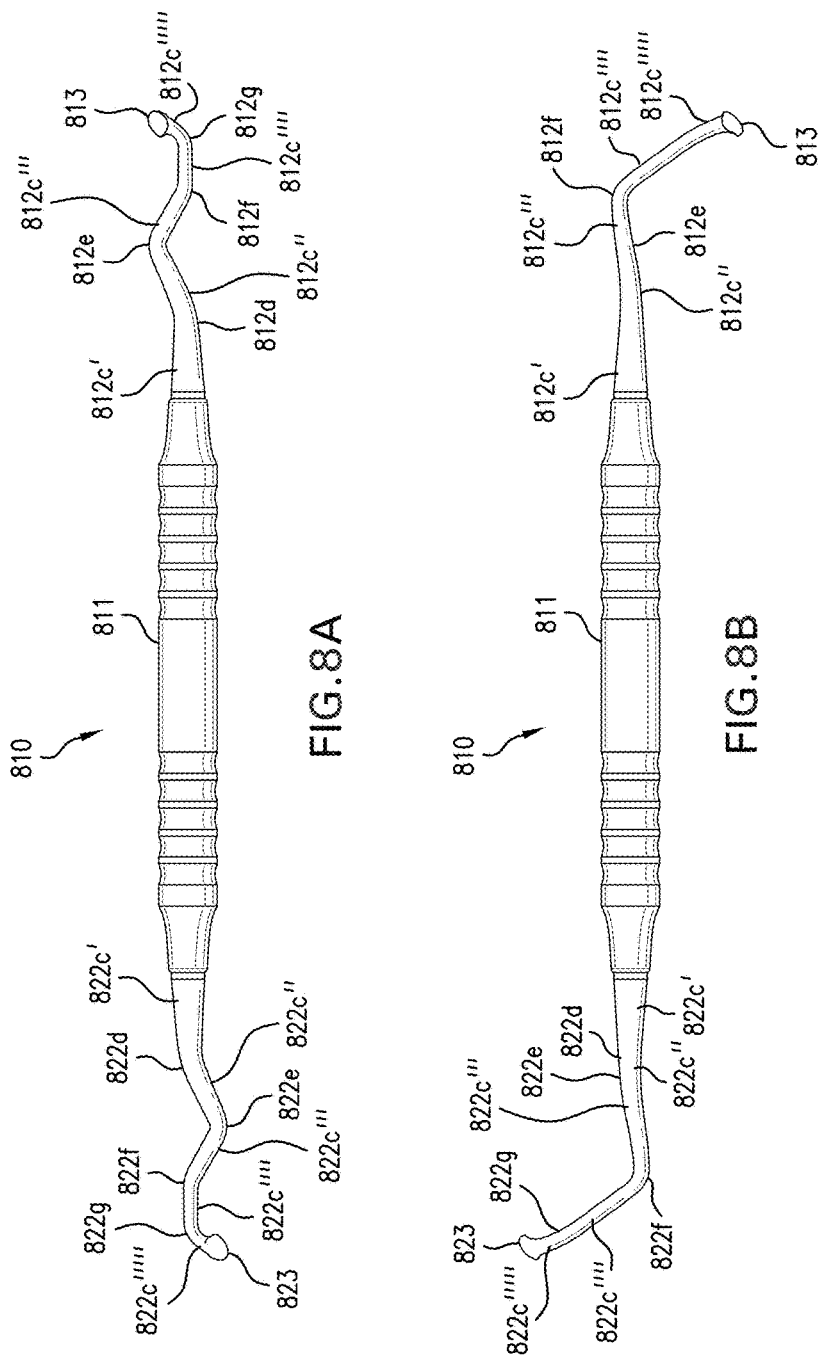
FIG. 8A is a top plan view of an eighth alternate embodiment of device according to the invention configured as an elevator, being similar to the device of FIG. 7A, having a longer reach.
FIG. 8B is a right side elevation view of the device of FIG. 8A.

Referring to FIGS. 8A and 8B, an alternate embodiment of an instrument 810 is shown. The instrument 810 is similar to the instrument 710, except that the first shank portion 812c' is longer than the second, third and fourth shank portions, 812c", 812c''', 812c'''', respectively, providing an extended reach of the instrument within a subperiosteal tunnel. The bends shown facilitate positioning and maneuvering the instrument through a subperiosteal tunnel, and to present the tip 813 for engagement with the structure within the tunnel or at the surgical site. According to a preferred embodiment, the first portion 812c' may be about 20 to 40 percent longer than the length of the respective second, third and fourth shank portions 812c", 812c''' and 812c''''. According to a preferred embodiment, the length of the second, third and fourth and fifth shank portions, respectively, 812c", 812c''', 812c'''' and 812c''''', may be similar to dimensions discussed in connection with the instrument 710, with the first portion 812c' being provided having a length of about 14 mm, that is, a length longer than the second through fourth portions. Alternatively, one or more of the second, third or fourth portions may be provided having a greater length. For example, the fourth portion 812c'''' may be provided having a greater length, and, according to a preferred embodiment, may be about 12 mm in the example depicted in FIGS. 8A and 8B, where the first portion 812c' is about 14 mm, the second and fourth portions 812c" and 812c'''', are each about 12 mm, and the third portion 812c''' is about 10 mm. The fifth portion 812c''''' including the tip 813 is about 20 mm.

Figure 9A:
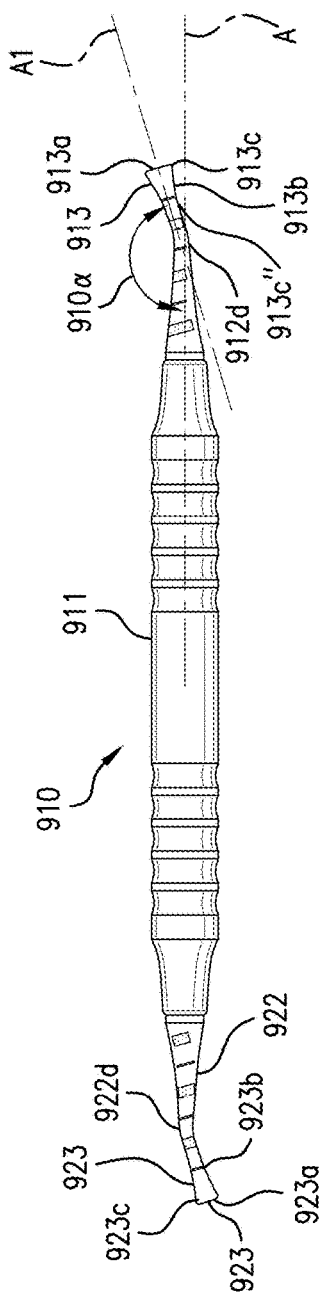
FIG. 9A is a top plan view of a ninth alternate embodiment of device according to the invention configured as a condenser.
Figure 9B:
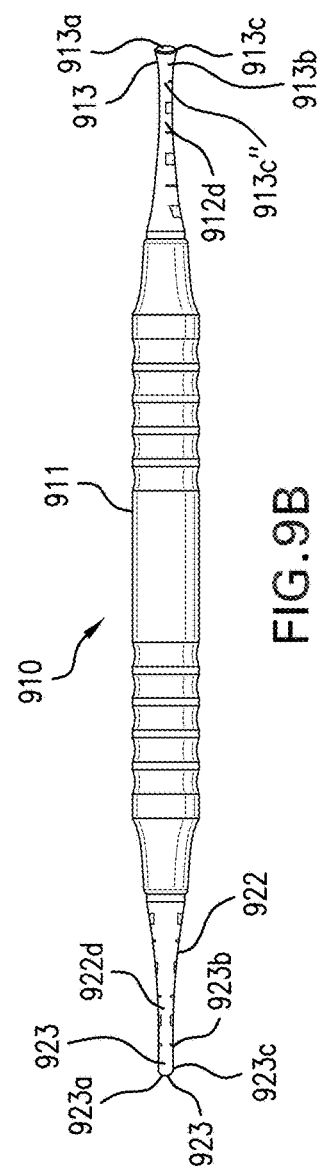
FIG. 9B is a right side elevation view of the device of FIG. 9A.
Figure 9C:
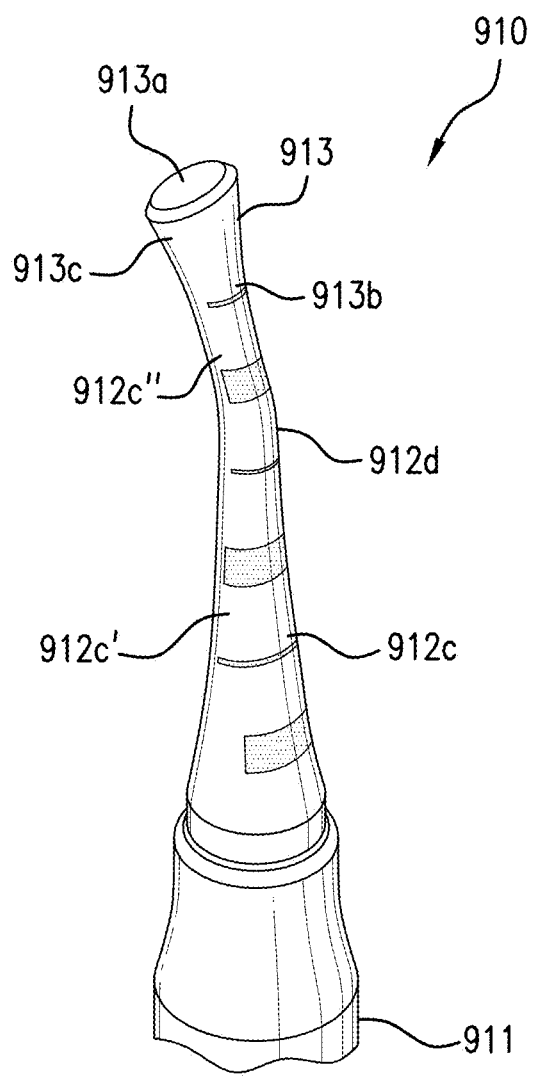
FIG. 9C is an enlarged partial view showing the shank end and tip of the device of FIG. 9A

Referring to FIGS. 9A, 9B and 9C, an instrument for conducting subperiosteal augmentation and reconstruction procedures is depicted, configured as a condenser instrument 910 is shown having a handle 911 with a body 911a, a first tapered portion 911b at one end of the body 911a, and a second tapered portion 911c at the other end of the body 911a. The condenser has a shank 912, with a first shank shaft portion 912c' and a second shank shaft portion 912c". The second shank shaft portion 912c" bends relative to the first shank shaft portion 912c' at an angle relative to the central axis A of the instrument 910. According to a preferred embodiment, the bend is along the central axis A and the central axis A2 of the second shaft portion 912c", with angle alpha 910 (α910) representing the angle of the bend. The instrument 910 depicted preferably includes a rounded tip 913, which, according to a preferred embodiment, is oval shaped, with an oval face 913a. The tip 913 preferably extends from a narrower portion 913b from the location where the tip 913 joins the distal end of the second shank shaft portion 912c". The tip 913 widens from the narrower proximal portion 913b distally to the tip end 913c. Preferably, the instrument tip 913 may have an oval shape, which may comprise an oval body with a thickness. The thickness preferably may be cross-sectionally oval, or, according to some embodiments, may be a flattened oval shape, with the oval shape being more pronounced closest to the distal tip end 913c supporting the tip surface 913a. Alternate views in FIGS. 9B-9C depict the condenser instrument 910 and tip 913.

According to a preferred embodiment, an oval tip, such as, for example, the oval tip 913, may be constructed to have a ratio of a long diameter width to the short diameter (height) of about 9 to 5, and more preferably from about 9 to 7 in the exemplary embodiment depicted. According to a preferred configuration, a condenser instrument 910 may be configured with an oval tip 913 which, preferably at the tip surface 913a, has a long width diameter of 4.5 mm and a shorter or height diameter of about 3.5 mm. The thickness of the long width preferably narrows from the tip surface 913a toward the tip proximal end 913b. The thickness of the short or height diameter also may narrow from the tip surface 913a at the distal tip end 913c to the proximal end 913b.

The instrument 910 preferably has a second shank 922 on the opposite handle end, shown comprising a first shank portion 922c' and second shank portion 922c" with a second tip 923 joining the distal end of the second shank portion 922c". In the embodiment illustrated in FIGS. 9A to 9C, the second tip 923 is provided as a smaller tip relative to the first tip 913. For example, according to a preferred embodiment, the second tip may be provided having a ratio of a long diameter width to the short diameter (height) of about 9 to 5, and more preferably, in the exemplary embodiment depicted, from about 7 to 5. According to a preferred configuration, the second tip 923 may be constructed having a long width diameter of 3.5 mm and a shorter or height diameter of about 2.5 mm. The thickness of the long width preferably narrows from the tip surface 923a toward the tip proximal end 923b. The thickness of the short or height diameter also may narrow from the tip surface 923a at the distal tip end 923c to the proximal end 913b. A beveled or angled edge may be provided at the tip end 923e near the tip surface 923a. A similar beveled end (not shown) may also be provided on the first tip 913. The shank 922 preferably also has a bend 912d therein similar to the shank 912 of the first end.

Referring to FIG. 10A, an alternate embodiment of an instrument 1010 configured as a condenser is shown. The condenser instrument 1010 is similar to the instrument 910 shown in FIG. 9A, but having an elongated shank shaft 1012, with a bend 1012d. The shank shaft first portion 1012c' preferably may be provided similar to the shank shaft portion 912c' of the instrument 910, but in the embodiment illustrated in FIG. 10A, the instrument 1010 has a longer reach due to a longer shank shaft second portion 1012c". The tip 1013 may be the same as the tip 913 shown and described herein, which according to a preferred embodiment is configured as an oval shape. The instrument 1010 also has a handle 1011, with a handle body 1011a, a tapered first portion 1011b, and tapered second portion 1011c. According to the embodiment illustrated, the instrument 1010 is configured as a condenser, and the angle alpha 1010 (α1010), is greater than the corresponding angle (α910) of the instrument 910, to provide an extended reach. Preferably, the extension of the tip 1013 may be axially away from the central axis A, an equal distance as the axial distance of the tip 913 in the instrument 910 of FIG. 9A, away from the central axis A of the instrument 910. The instrument 1010 also includes a second end, having a second shank 1022 on the opposite side of the handle 1011. The second shank 1022 includes a shank shaft first portion 1022c', providing a longer reach similar to the shank shaft first portion 1012c', and includes a second shank shaft portion 1012c" with a second tip 1023. The second tip 1023 preferably is configured similar to the second tip 923 provided in connection with the instrument 910.

Features discussed and shown herein in conjunction with one or more embodiments of the devices may be combined with one or more features and implemented together. In addition, although instruments are depicted with shanks that may be of similar length at each handle end, shanks of different lengths may be provided, according to some alternate embodiments. In addition, as discussed above in connection with the shank 112, the outer surface of the instruments shown and described herein, including on the shanks, may include a scale thereon that provides a depth indicator. Shanks preferably may have a series of evenly spaced markings which may be visibly provided thereon to mark the depth at a point along the shank, from the tip end. The marking depth indication provides a depth indication to the user when the instrument is inserted in a subperiosteal tunnel or otherwise penetrates tissue, so the user will know the penetration depth of the instrument (when the instrument portion, such as the shank, is within the tunnel and not visible to the user). While the devices of the invention have been disclosed in detail, and the preferred embodiments and best mode for practice of the invention have been similarly disclosed, the scope of exclusive rights to which the invention is entitled is defined by the claims appended hereto and by equivalents that perform substantially the same function in substantially the same way to achieve the same result.

Figure 11C:
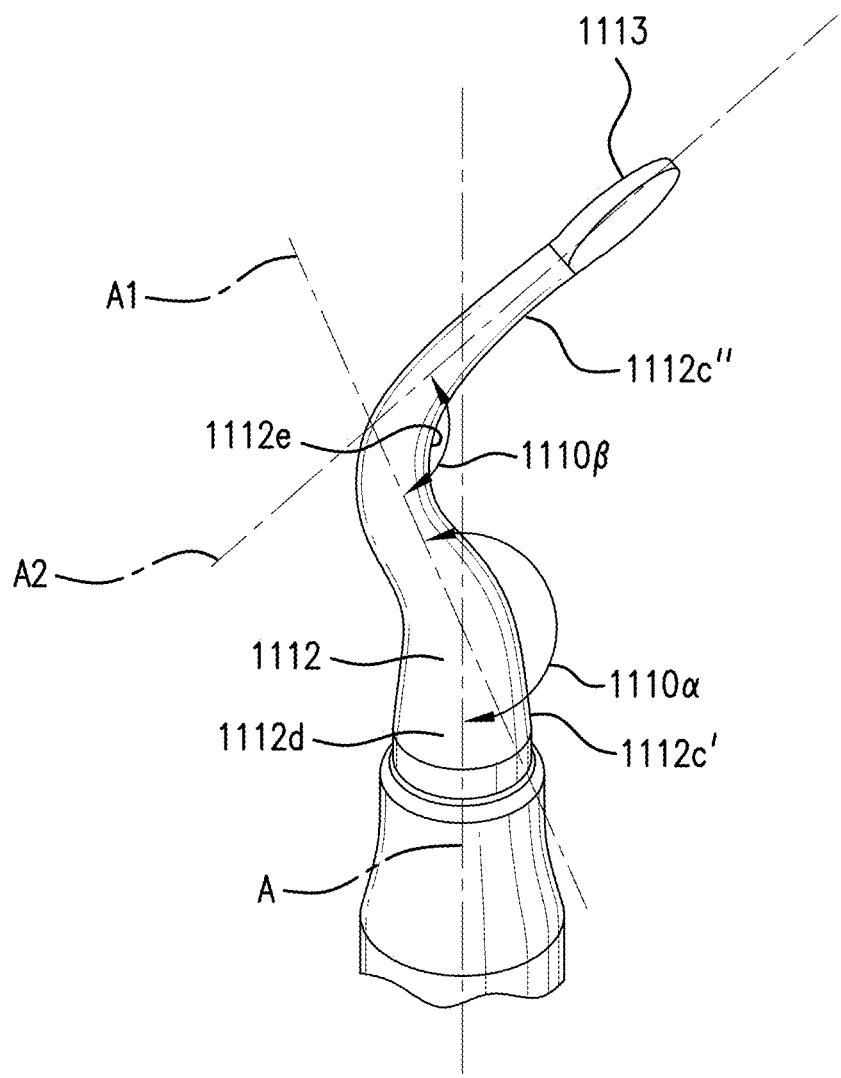
FIG. 11C is an enlarged partial view showing the shank end and tip of the device of FIG. 11A.

Referring to FIGS. 11A to 11C, a compactor 1110 is shown having a handle 1111 with a first shank 1112 at the first handle end, and a tip 1113 at the distal end of the shank 1112. The shank 1112 is shown comprising a first shank portion 1112c' and a second shank portion 1112c'', with a first bend 1112d at the first shank portion 1112c' joining the handle 1111, and a second bend 1112e where the first shank portion 1112c' and second shank portion 1112c'' join. The tip 1113 is shown at the distal end of the second shank portion 1112c''. The instrument 1110 is configured as a compactor, which may be utilized in a subperiosteal tunnel and/or surgical site to compact tissue or bone material, including bone graft material. The instrument 1110 preferably is configured to be maneuverable within the mucosa and/or subperiosteal tissue to apply a force in a desired direction that may be directed by movements of the handle 1111. For example, the handle 1111 may be manipulated by moving it forward or rearward angling it, and/or rotating it, or by combinations of these movements consecutively, or simultaneously, to direct the tip 1113. As shown in FIGS. 11A, 11B, 11C, the tip 1113 is oval in configuration with a substantially flat profile, having a thickness substantially less than the length and width of the oval. The tip 1113 and shank 1112 (or portion thereof) may be introduced in a subperiosteal tunnel and may be maneuvered to compact the graft. For example, where graft material is introduced at a remote surgical site, the instrument shank 1112 may be directed through a tunnel and to the surgical site, where the tip 1113 can be manipulated, preferably via the handle 1111, to engage the graft material at the surgical site. Preferably, the tip 1113 is linear and is aligned with the axis of the second shank portion 1112c'' to which the tip 1113 is joined.

According to preferred embodiments, the instrument 1110 may be provided with markings on the shank. Preferably, the markings are provided on a linear scale to mark the linear distance from the tip to a location on the shank 1112. For example, according to a preferred embodiment, the markings may be designated in units, such as millimeters, and may be marked periodically, such as every 1 mm, 3 mm, 5 mm, or other arrangement. The marking indicia may be etched, engraved, or applied by other suitable marking methods, suitable for being able to insert the marked shank 1112 into tissue, including a subperiosteal tunnel and surgical site. The linear markings, for example, measure a length along the instrument central axis, from the tip end 1113e. As shown in FIG. 11B, the markings are linear, and therefore, any measurements are continued to be measured linear, along the central axis, and in the embodiment illustrated, are not necessarily measured from the axis of the shank 1112 (which has a greater length than the portion of the instrument central axis that the shank 1112 spans).

According to a preferred embodiment, the oval tip 1113 may be provided having a length that is axially longer than the width, as illustrated in FIGS. 11A-11C. One preferred ratio of the length to width is about 11 to 8. For example, according to a preferred instrument embodiment, the oval may have a length of 5.5 mm and a width of about 4 mm. The instrument 1110 is shown having a thickness that is less than the width of the oval. Some preferred embodiments provide a thickness that is about 1 to 3 mm in thickness, and more preferably from about 1.5 to 2.5 mm.

The compactor instrument 1110 preferably is configured with a second shank portion 1112c'' that is longer than the first shank portion 1112c'. The first shank portion 1112c' preferably, at the first bend 1112d is angularly bent relative to the handle 1111, as measured in reference to the instrument central axis A and the central axis A1 of the first shank portion 1112c' at an angle alpha (1110α). The first angle 1110α preferably is provided to be less than about 45 degrees, and more preferably, between about 15 and 35 degrees.

The second shank portion 1112c'' preferably, at the second bend 1112e is angularly bent relative to the first shank portion 1112c', at an angle beta (1110β), as measured between the central axis A2 of the second shank portion 1112c'' and the central axis A1 of the first shank portion 1112c'. The second angle 1110β preferably is provided to be greater than the first angle alpha (1110α). The second angle 1110β preferably is less than 180 degrees, and more preferably is between about 120 to 170 degrees. According to preferred embodiments, the compactor 1110 preferably may have a second end with a second shank 1122 extending from the handle 1111. According to some embodiments, the second shank 1122 may be constructed similar to the first shank 1112, with a second tip 1123 provided on the second shank portion 1122c'', and with the second shank portion 1122c'' being provided at a bend 1122d where the second shank portion 1122c'' joins the first shank portion 1122c'. The first shank portion 1122c' is shown extending from the handle 1111. The second tip 1123 may be configured to be the same as the first tip 1113. According to some alternate embodiments, the second tip 1123 may be different than the first tip 1113. For example, the second tip may be provided having a different size, where the tip is relatively smaller or larger. The second tip may maintain proportions of the first tip oval configurations (and/or thicknesses) although it may be smaller or larger in some alternate embodiments. According to some other embodiments, the second tip may be provided with different proportions, and/or thicknesses.

According to a preferred embodiment, the compactor 1110 is constructed with the portion of the shank shaft 1112c between the first bend 1112d and second bend 1112e being about 14 mm, and with the portion between the second bend 1112e to the tip 1113, inclusive of the tip length, being about 22 mm. Similarly, the second shank 1122c may be constructed with similar dimensions.

Referring to FIGS. 12A and 12B, an alternate embodiment of an instrument 1210 configured as a compactor is shown. The compactor instrument 1210 is similar to the compactor instrument 1110 of FIGS. 11A, 11B and 11C, except that each shank 1212, 1223 is longer, and the angles of the shank bends, the first angle alpha (1210α) and second angle beta (1210β) in the instrument 1210 are provided to produce less of a bend. The first angle alpha (1210α) of the instrument 1210 is less than the corresponding angle (1110α) of the instrument 1110. The second angle beta (1210β) of the instrument 1210 is greater than the second angle beta (1110β) of the instrument 1110. The first shank shaft portion 1212c' on the first end of the instrument 1210 is longer in relation to the first shank shaft portion 1112c' in the instrument 1110 depicted in FIGS. 12A and 12B, as is the second shank portion 1212c" which is longer than the corresponding second shank portion 1112c" of the instrument 1110. In the longer instrument 1210, the tip 1213 is distally further from the handle 1211. The shank 1212 is constructed to have less pronounced angular bends at the first bend 1212d and second bend 1212e so as to provide a maximum instrument width that includes deviations from the central axis A, on either side. According to some embodiments, the axial width or window for the instrument 1110 may be the same window as for the instrument 1210, with the additional shank length being accommodated by a reduction in the outward deviation of the shaft relative to the central axis A. The second instrument end includes a second tip 1223 provided at the end of the second shaft 1222. The second shaft 1222 extends from the handle 1211, and preferably from the tapered portion 1211c and to where it joins the tip 1223 at the distal shank end. Similar to the first shaft portion 1212c' and second shaft portion 1212c" of the first shaft 1212, the second shaft 1222 includes a first shaft portion 1222c' and second shaft portion 1222c".

According to a preferred embodiment, the compactor 1210 is constructed with the portion of the shank shaft 1212c between the first bend 1212d and second bend 1212e being about 19 mm, and with the portion between the second bend 1212e to the tip 1213, inclusive of the tip length, being about 27 mm. Similarly, the second shank 1222c may be constructed with similar dimensions. In a preferred embodiment, each oval tip 1213, 1223, preferably, is similar to the oval tip 1113 and 1123 of the instrument 1110. According to a preferred embodiment, the tips 1213 and 1223, may be about 5.5 mm in length, with a width of about 4 mm.

According to preferred embodiments, the instrument tips, such as, for example, the tips 1113, 1123, 1213, and 1223, preferably are oval in configuration and may have a tapered thickness, which may be wedge shaped, as illustrated in the side views of FIGS. 11A and 12A, for the respective instruments 1110 and 1210. The tapered tip 1113, for example, may be provided with both sides being tapered to converge. For example, according to the embodiment illustrated in FIG. 11B, the tip surfaces are shown converging toward the axis A from the proximal tip end to the distal tip end. Similarly, the tip 1213 of the instrument 1210 shown in FIG. 12B is shown with the converging surfaces. The tips of the other ends of the instruments (1123 and 1223) also may be similarly configured. According to some alternate embodiments, a single side of the tip 1113 may converge and the other side may remain axially straight. Preferably, the tip 1113 includes an end portion with a surface 1113e for engaging with material, such as, for example, bone graft material, to position or compact the material into place.

FIG. 13A illustrates an exemplary embodiment of a syringe 1321 according to the invention, which includes a first syringe embodiment 1321 depicted in a top plan view in FIG. 13A, and in a side view in FIG. 13B.

FIG. 14 illustrates another alternate exemplary embodiment of a syringe 1422 according to the invention, which is shown in a side elevation view.

Figure 15:
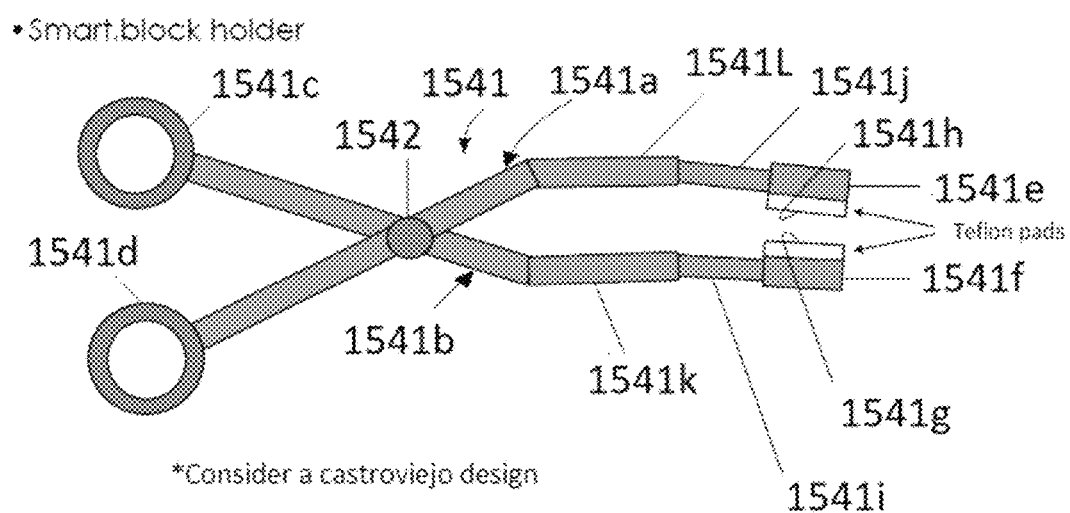
FIG. 15 illustrates a side elevation view of an exemplary depiction of a holder in accordance with the invention.

FIG. 15 illustrates an exemplary embodiment of a holder 1541 configured in accordance with an embodiment of the invention. The holder 1541 may also be referred to as a carrier for carrying the graft. The holder 1541, includes a pair of arms 1541a, 1541b, handles or loops 1541c, 1541d for grasping by the medical personnel (e.g., surgeon), and clamping ends 1541e, 1541f. The clamping jaws or ends 1541e, 1541f, preferably include respective clamping surfaces, 1541g, 1541h, thereon. According to preferred embodiments, the clamping surfaces, 1541g, 1541h, preferably are constructed from tough synthetic resin, such as, for example, polytetrafluoroethylene, or other suitable durable material that may be sterilized (e.g., where high temperature resistance is required), and which is able to grip the graft and hold the graft without damaging it during the time that the graft is maneuvered through the tunnel. The holder 1541 may be used to position the graft at the surgical site, and within the pouch. According to some preferred embodiments, the holder arms 1541a, 1541b, may be pivotally connected with a connector 1542. The holder 1541 is shown having a first plurality of arm segments, such as those upper or first arm segments 1541i, 1541j on the upper arm 1541a, and those lower or second arm segments, 1541k, 1541L on the lower arm 1541b. The arm segments 1541i, 1541j and 1541k, 1541L are configured to provide maneuverability thereof for facilitating maneuvering and manipulation of the bone graft through a tunnel created in the tissue, for moving the graft from the remote incision through the tunnel and to the surgical site or pouch. According to preferred embodiments, the holder 1541 preferably has a clamping mechanism that maintains the clamping force applied to provide continuing grasp of an object, such as the graft being held and maneuvered. According to some embodiments, the clamping may be accomplished by providing a ratchet mechanism that engages when the arm handles or loops are moved together to actuate the clamping ends, such as those ends 1541e, 1541f, to engage the graft. According to preferred embodiments, the clamping force is maintained while the arm segments are maneuverably manipulated to change direction as the instrument is directed to move the graft along the tunnel passageway. Arm segments may be linked together for multi-directional maneuvering within the tunnel passageway.

Implantable articles may comprise a pre-milled block, 3D printed grafts, molded bone/collagen grafts, or particulate formed grafts held together by a binding or adhesive agent. According to some embodiments, the invention further provides blocks that are usable as graftable implants, which, may be applied using the method disclosed herein. According to preferred embodiments, the invention provides implantable media comprising pre-shaped xenograft or mineral blocks, and pre-shaped xenograft or mineral blocks with 1%-99% content of collagen or a binding or adhesive substance. The implantable media preferably comprises anorganic bone, and may comprise anorganic human, bovine, equine, porcine or mineral bone. The pre-milled or pre-molded xenograft or mineral blocks are configured having different shapes or designs, and preferably, are designed for application to treat vertical and horizontal jaw bone defects of different morphologies. The pre-milled xenograft blocks preferably may be configured to be installed at a surgical site. According to some embodiments, where a vertical approach is carried out, such as, for example, where a vertically oriented tunnel is developed for transport of the desired appropriate block to the surgical site. In addition, embodiments of the invention may implement computer assisted and photographic imaging techniques to design and fabricate custom xenograft blocks. Preferably, the xenograft block may be fabricated to be configured having a suitable shape, such as a depth or thickness, and contour, which is individually suited for the procedure, such as, an augmentation or restoration for a particular individual.

The block may be custom fabricated also to take into account the location from which the block will be installed, and the configuration of the surgical site when the block is to be installed. According to some embodiments, the image of an individual (e.g., a patient) may be obtained using any suitable imaging technique (e.g., radiography, ultrasound, or the like), and the graft may be designed based on the physiology of the individual at the treatment location, where the implantable article, the bone graft, is to be installed. For example, individualized, customized xenograft blocks may be custom fabricated to produce a block having a configuration to treat a specific defect. Advanced imaging and CAD/CAM techniques may be utilized to obtain visual information (about the individual), and the design of the implant that is desired for use. According to some embodiments, milling may be carried out to produce the customized xenograft block, and according to some alternate embodiments, the xenograft or mineral blocks may be 3D printed. In addition, the xenograft or mineral blocks and collagen containing blocks, according to the invention, may be produced in multiple shapes and sizes to treat defects of different dimensions. These shapes may also be achieved by mixing the bone graft particles with a binding or adhesive agent creating a paste or putty like compound that can be molded into different shapes.

Figure 16:
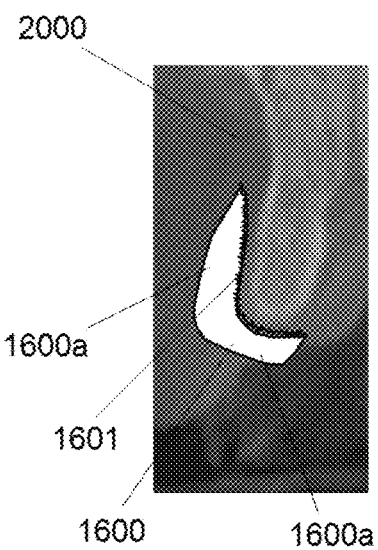
FIGS. 16-35 illustrate exemplary embodiments of grafts provided according to the invention, shown installed in an environment in a patient's mouth, in particular, in the periosteum of the maxilla.

According to some preferred embodiments, the xenografts and mineral grafts are constructed having a textured intaglio surface for enhanced angiogenesis. According to some embodiments, the xenograft or mineral graft surface, including, for example, the textured intaglio surface, may be provided with or treated with biologic modifiers. (i.e. tissue adhesives, growth factors, or any other osteoinductive agents) According to a preferred embodiment. As shown in FIG. 16, an implantable article configured comprising a xenograft 1600 is illustrated according to an exemplary embodiment of the invention. The xenograft 1600 is shown having an inner surface 1601 that is configured with a texturized contour. The contour is shown comprising surface treatment. The surface treatment according to preferred embodiments is configured to increase the surface area to promote healing of the graft when installed in the individual. According to some preferred embodiments, the surface configuration is carried out to enhance the permeability of the graft surface. For illustration purposes, the graft surface contour shown in FIG. 16 may be depicted larger than the surface texture actually may appear in embodiments. In the illustration in FIG. 16, the xenograft 1600 is illustrated installed in an environment, which is below the periosteum tissue of an individual's maxilla 2000. In accordance with preferred embodiments, the xenograft 1600 is seated within a pouch of the tissue. The xenograft 1600 illustrated includes a length portion 1600a and a base portion 1600b. The xenograft 1600 is shown depicted in an exemplary illustration, where the xenograft 1600 has its length portion 1600a substantially vertically oriented, along the substantially vertical portion of the maxilla 2000.

Figures 17, 18, 19:
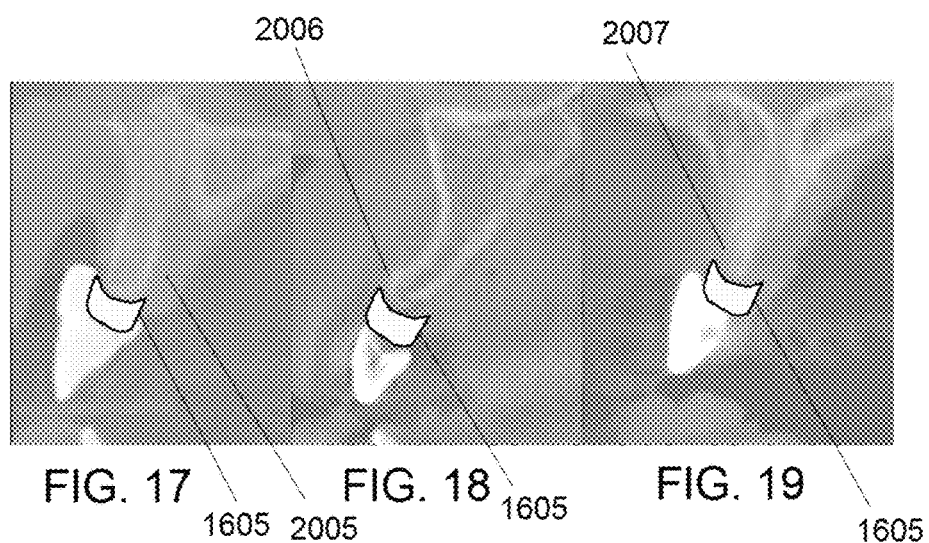
Figures 20, 21, 22:
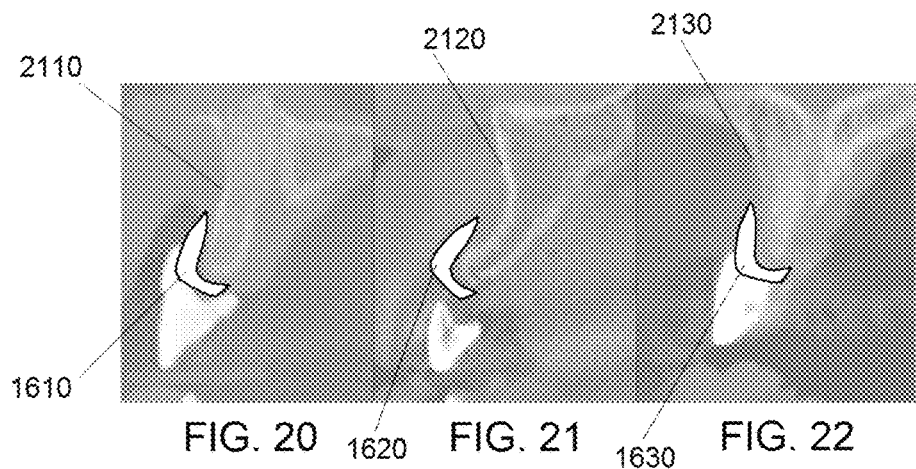
Figures 23, 24, 25:
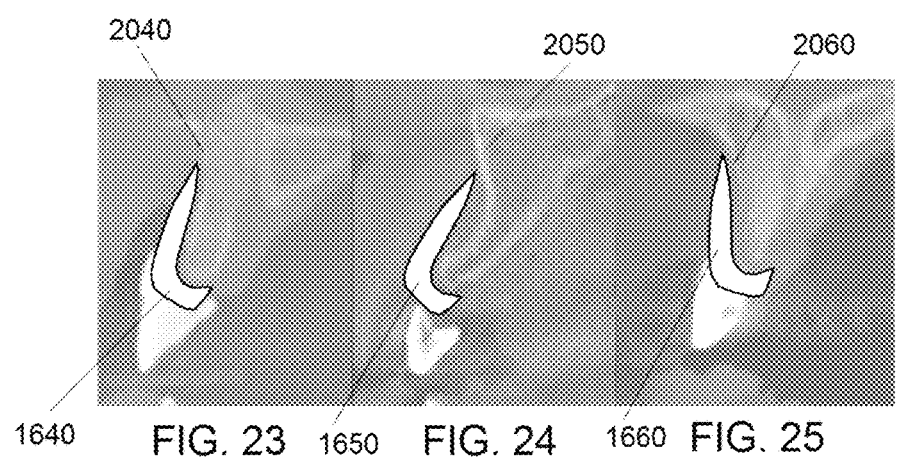

FIGS. 17-25 are illustrations depicting exemplary installations of xenografts in accordance with the invention. Referring to FIGS. 17-19, a xenograft block 1605 is shown having a base 1605a and is shown in an exemplary environment in which it is installed, which is below the periosteum tissue of an individual's maxilla 2005. In accordance with preferred embodiments, the xenograft 1605 is seated within a pouch of the tissue, and includes a base portion 1605b, and two upstanding portions 1605a, 1605c, on each respective end thereof. The positioning of the xenograft 1605 is shown in conjunction with the patient environment, installed the respective maxilla 2005, 2006, 2007, of FIGS. 17-19. Referring to FIG. 20 an exemplary embodiment of a xenograft block 1610 according to the invention is shown. The xenograft block 1610 is illustrated in an environment installed in a maxilla 2010, and preferably is seated within a pouch formed below the periosteum. Referring to FIG. 21 another exemplary embodiment of a xenograft block 1620 according to the invention is shown. The xenograft block 1610 is illustrated in an environment installed in a maxilla 2020, and preferably is seated within a pouch formed below the periosteum. Referring to FIG. 22, an exemplary embodiment of a xenograft block 1630 according to the invention is shown. The xenograft block 630 is illustrated in an environment installed in a maxilla 2030, and preferably is seated within a pouch formed under the periosteum. FIGS. 23, 24 and 25 illustrate xenograft blocks 1640,1650,1660, respectively, where each is shown in an environment installed in a respective maxilla 2040,2050,2060, and preferably being seated within a respective pouch formed under the periosteum. According to a preferred embodiment, the xenograft blocks 1600, 1610, 1620, 1630, 1640, 1650, 1660, preferably may be pre-formed, and supplied as illustrated. According to some preferred embodiments, the xenografts may be provided with a biological agent, or pre-treated with biologic surface modifiers or adhesives. According to some alternate embodiments, the surface modifiers or adhesives may be applied together with the xenograft, and applied prior to application.

Figure 26:
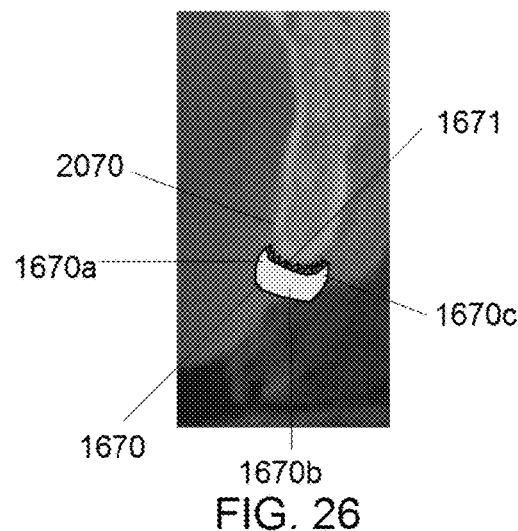

FIG. 26 illustrates a further example of a xenograft block 1670, which preferably may be a pre-milled xenograft block, and may be formed from a suitable bone, such as, for example, human, bovine, equine, porcine or mineral bone. As illustrated in FIG. 26, the xenograft 1670 is shown in an exemplary environment in which it is installed, which is under the periosteum tissue of an individual's maxilla 2070. In accordance with preferred embodiments, the xenograft 1670 is seated within a pouch of the tissue, and includes a base portion 1670b, and two upstanding portions 1670a, 1670c, on each respective end thereof. The xenograft 1670 is shown having an inner surface 1671 that is configured with a texturized contour. The contour is shown comprising surface treatment. The surface treatment according to preferred embodiments is configured to increase the surface area to promote healing of the graft when installed in the individual. According to some preferred embodiments, the surface configuration is carried out to enhance the permeability of the graft surface. The surface treatment may comprise collagen or other suitable materials, and the surface treatment may provide benefits similar to the xenograft 1600 shown and described herein in connection with FIG. 16. Although not depicted, the grafts illustrated in FIGS. 17 through 35 may be provided with a surface treatment, which may be similar to the surface treatments shown and described herein in connection with the grafts 1600 and 1670 of FIGS. 16 and 26, respectively.

Figures 27, 28, 29:
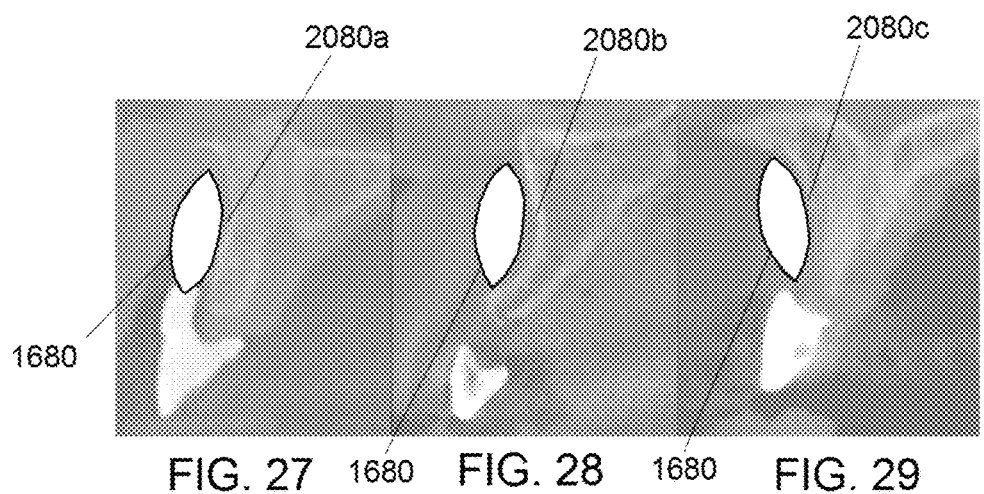

As illustrated in FIGS. 27, 28 and 29, another embodiment of a xenograft 1680 is illustrated. The xenograft may be formed from a suitable process, which, according to some embodiments, may include milling, and according to other embodiments, may include forming the xenograft 1680 from bone material, such as granules, or bone particles. For example, the xenograft 1680 may be formed by molding bone material, such as particles or granules, which may comprise human, bovine, equine, porcine or mineral material. The xenograft 1680 may be formed in accordance with a suitable molding method, and, according to some embodiments, may be formed in accordance with the molding methods disclosed herein. The configuration of the xenograft, is illustrated having a substantially tapered configuration, and is shown in a bi-tapered embodiment, with tapers formed at each end thereof, and preferably having a larger mid-section diameter, tapering smaller from the mid-section to each respective end thereof. The xenograft 1680 may be dimensionally configured to have a thickness, which in some embodiments may be provided as a flattened configuration, while in other embodiments, may be radially or substantially radially configured. The xenograft 1680, according to preferred embodiments, may be molded with one or more agents, and preferably, includes collagen or another binding or adhesive agent. According to preferred embodiments, the collagen is present in an amount by weight of preferably less than about 10%. Referring to FIGS. 27, 28 and 29, the xenograft 1680 is illustrated installed in three representative exemplary environments, which, comprise the subperiosteal area of the maxilla of a respective individual, referenced as 2080*a*, 2080*b*, 2080*c*, respectively. In accordance with preferred embodiments, the xenograft 1680, in each of the respective exemplary environments 2080*a*, 2080*b*,2080*c*, in the respective FIGS. 27, 28 and 29, is seated within a pouch of the tissue. The xenograft 1680 is illustrated in accordance with a preferred configuration having a substantially symmetrical shape, but other embodiments of the xenograft may have a configuration that is close to symmetrical, asymmetric, or slightly asymmetric. The symmetry may be longitudinal or equatorial. The xenograft 1680 illustrated in FIGS. 27, 28 and 29, is shown representative of an exemplary embodiment that is or is substantially equatorially and longitudinally symmetrical. In embodiments where the xenograft is configured to be asymmetric or slightly asymmetric, or close to symmetric, orienting of the xenograft may be accomplished to provide the most beneficial positioning for treatment to take effect. In each respective one of the FIGS. 27, 28 and 29, there is an environment where the pouch formation, in accordance with the method preferably is created at locations corresponding with the desired placement of the graft 1680. The xenograft 680 may be constructed with a surface treatment, such as the surface treatments shown and described herein, including those in connection with the xenograft 1600 and 1670 of FIGS. 16 and 26.

Figures 30, 31, 32:
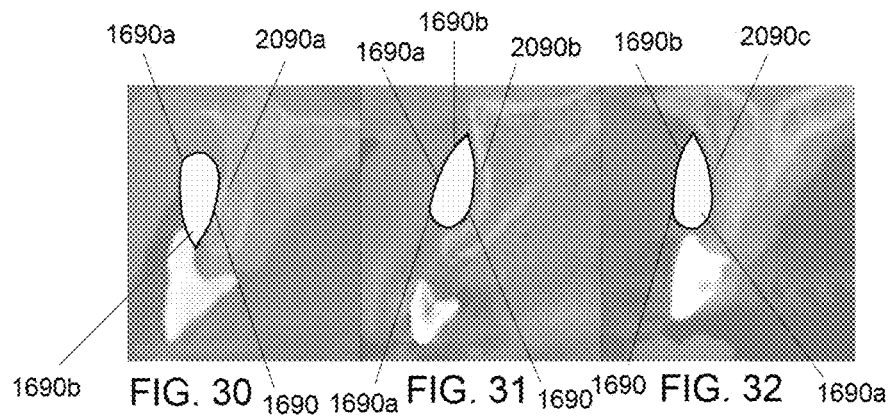

Referring to FIGS. 30, 31 and 32, an alternate embodiment of a xenograft 1690 is illustrated. The xenograft 1690 may be similar to the xenograft 1680 shown and described herein in connection with FIGS. 27, 28 and 29, but is illustrated in FIGS. 30, 31 and 32 having a configuration that does not have equatorial symmetry, but may have longitudinal symmetry. The configuration of the xenograft 1690 is shown having a tear-drop like shape, and having a larger end 1690*a*, and a smaller end, which, according to a preferred configuration is a tapered end 1690*b*. The xenograft 1690 is illustrated installed in three representative exemplary environments, which, comprise a subperiosteal area of the maxilla of a respective individual, referenced as 2090*a*, 2090*b*, 2090*c*, respectively. In accordance with preferred embodiments, the xenograft 690, in each of the respective exemplary environments 2090*a*,2090*b*,2090*c*, in the respective FIGS. 30, 31 and 32, is seated within a pouch of the tissue.

Figures 33, 34, 35:
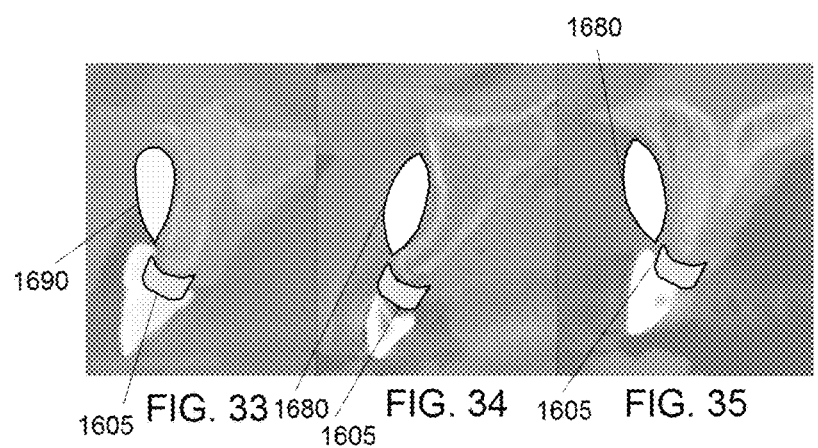

Combinations of xenografts may be implanted using the methods disclosed herein. For example, referring to FIGS. 33, 34 and 35, an exemplary depiction of a combination of xenografts is illustrated. In FIGS. 33, 34 and 35, the xenograft 1605 (which also is shown in FIGS. 17, 18 and 19), is illustrated in an implementation of the method where a combination of xenografts, preferably one or more combinations, for example, of xenografts are installed at a surgical site. In FIG. 33, the xenograft 1605 is illustrated implanted along with the xenograft 1690 (see e.g., FIGS. 30-32). In FIGS. 34 and 35, the xenograft 1605 is shown implanted with the xenograft 1680 (see e.g., FIGS. 27-29), which are implanted to remediate conditions of the jaw, mandible and/or maxilla, and preferably, as shown and described herein, are implanted under the periosteum (to remediate conditions of the jaw e.g., mandible and/or maxilla). According to preferred implementations of the method, the xenografts, when used in combination, may be implanted through a single tunnel or multiple tunnels. For example, the tunnel may have a first pouch at one location thereof for receiving a first xenograft, and may have a second tunnel at another location thereof, for receiving a second xenograft. Alternatively, according to some other implementations of the method, separate tunnels may be developed for each xenograft. According to some implementations, the implantable articles comprising the xenografts, such as, for example, those illustrated in FIGS. 16-35, may be installed within a pouch, in accordance with the method, and additional material, such as, bone particles, which may be treated or untreated bone particles, may be inserted around the xenograft block or mold (e.g., though injection or other introduction method). The introduction of the treated or untreated bone particles, which may comprise, human, bovine, equine, porcine or mineral material (which in some embodiments, may be treated with an agent, such as, collagen, binding agent, tissue adhesive, growth factor, or other biologic substance to promote growth, and/or viability), may be introduced to the site, and preferably the pouch, through the tunnel developed under the periosteum.

The methods and xenografts shown and described preferably facilitate the further treatment of a condition, which may involve re-attaching exposed surface areas of teeth and dental implants to the jaw bone, and providing for the reconstruction and regeneration of gingival papillae.

Although described in connection with delivering bone material to augment the existing bone by developing a tunnel and pouch at a location to deliver bone graft material between the patient's existing bone and the periosteum, alternatively, bone material may be delivered to an already existing implant, such as, for example, a metal implant that was installed on the mandibular or maxillary structure in place of a tooth. The delivery of bone is designed to strengthen or improve the support for the implant, which may be lacking in bone. A remote incision, as discussed herein, a tunnel and pouch are developed as shown and described herein, except that the pouch is on one side exposed to the implant surface, or alternatively, to the implant surface and possible bone structure that may be present and in need of augmentation. An instrument, such as, for example, a syringe, and preferably a specially designed syringe, may be used to deliver bone material to the site of the already existing implant via the remote incision and subperiosteal tunnel, and into the pouch formed to support the implant, which preferably has one side or portion exposed to the implant, and the other portion bounded by the periosteum. The bone graft material may be delivered to the pouch as discussed herein, and preferably manipulated to provide the desired arrangement in the pouch for supporting the implant. The remote incision preferably may be closed in accordance with the techniques and steps described herein.

The methods for delivering bone material to a patients jaw may also be done in conjunction with the addition of bone in instances where a natural tooth is present at the site, but where the existing bone requires further support or development, such as, for example, in the case of trauma or a natural defect (e.g., a concavity in the bone structure, recession, bone deficit, or other developmental issue). The remote incision, tunnel, and pouch may be employed to create a pouch at the site where the bone material is desired (e.g., the defect site), and bone graft material may be admitted to the site and manipulated into position. For example, the methods may be carried out to deliver bone graft material to develop the alveolar ridge, or to enhance the permanent root of a tooth.

In addition, in accordance with an alternate embodiment, the methods disclosed herein may be implemented to deliver bone graft material to a site that is to receive an implant, while in other instances, the methods may be carried out to deliver bone graft material to a site contemporaneously with the placement of an implant. For example, in this latter implementation, the method may comprise the placement of bone graft material buccal or lateral to the implant.

According to some alternate embodiments, the xenograft or mineral blocks may be formed from granular bone particles that are assembled together, through compaction and/or with a binding agent, for example collagen or a biologic adhesive.

According to some preferred embodiments, blocks according to the present invention may be provided having a surface layer, treated surface, or with a treatment. According to a preferred embodiment, the xenograft, allograft or mineral block is provided having a collagen layer on the tissue-facing side. According to some preferred embodiments, the xenografts may be formed from granular material, such as, for example, granular human, bovine, equine, porcine or mineral material.

According to some embodiments, the method may include using a syringe to supply a granular bone material to the surgical site. The introduction of the biologic agent or particulate bone material may be done in addition to the xenograft, allograft or mineral block provided by the invention. The biologic agent may be delivered according to the method, through the remote incision, via the tunneling procedure, and into the pouch.

In a preferred embodiment, the biologic agent may be mixed or added to the granular graft material. In an alternative embodiment, the bone or bone/collagen block may be treated with the biologic agent.

Figure 37:
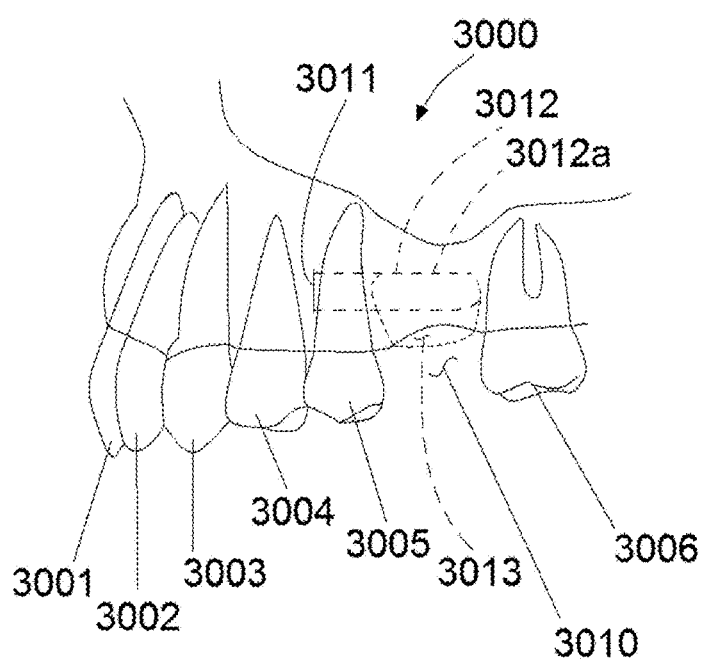
FIG. 37 is a left side perspective view of the upper portion of the jaw, or maxilla, shown in an example representing an implementation of the method.

According to one example, the method is illustrated as carried out on the maxilla of a patient, where the jaw is to be augmented with implantable bone material to build up the area to receive an implant. Referring to FIG. 37, an exemplary depiction of a portion of a patient's jaw 3000 is illustrated. The jaw 3000 includes teeth, comprising a left maxillary central incisor 3001, a left maxillary lateral incisor 3002, left maxillary cuspid 3003, left maxillary first bicuspid 3004, left maxillary second bicuspid 3005, left maxillary second molar 3006. As shown, the left maxillary first molar is missing, and the molar space 3010 is shown proximate to the location where an implant is to be installed. A remote incision 3011 is made, and, preferably is a 5 to 6 mm vertical or oblique full thickness incision. The remote incision is located to one tooth distance away from the site that is to receive the graft. As is illustrated in FIG. 37, the remote incision 3011 is situated at a location that ensures that periosteal injury and subsequent inflammatory reaction are minimized and do not interfere with the healing of the bone graft. A subperiosteal tunnel 3012 is developed avoiding damage to the periosteum. The tunnel provides laparoscopic access to the graft site 3013, which in the example illustrated, is at the distal end 3012a of the tunnel 3012. The tunnel 3012 is shown having controlled dimensions, and, according to preferred embodiments, is developed so as to avoid the potential for migration of graft particles. In the embodiment illustrated, the tunnel 3012 is narrower than the graft site or pouch 3013 that is to receive the graft. The subperiosteal pouch 3013 is developed to house the bone graft. The method preferably is carried out to leave the periosteum intact, or substantially intact, so as to provide a source for regenerative cells. As shown in FIG. 37, the confines of the pouch 3013 are delineated in order to avoid migration of the bone graft/biomaterial. Instrumentation is inserted into the remote incision 3011 and maneuvered through the tunnel 3012, and is manipulated to develop the pouch 3013 at the site that is to receive the graft. In the example depicted, the graft site is located where a left maxillary second molar space 3010 is located. The remote incision 3011 is shown provided slightly mesial of the adjacent tooth, which in this example, is the left maxillary second bicuspid 3005. The incision 3011 is remote from the pouch 3013, and the pouch allows for the aggregation of bone material to result in horizontal or vertical bone augmentation. The aggregation of the material results in the distension of the soft tissues at the remote site or pouch 3013. In the example illustrated, the location of the remote incision allows for the distribution of tension over a wider soft tissue area, facilitating co-aptation of the wound edges over the augmented bone volume. According to preferred embodiments of the method, the remote incision preferably is closed using stitches. The closing of the remote incision may be done with a thickness layer of the mucosa, or alternately, may be done by suturing together layers of the periosteum and mucosa thickness. Preferably, the incision edges are everted, with the inner layers meeting to effect a facilitation of the healing of the incision wound. The tunnel configuration and placement preferably allows for tension to be provided on the tissue so as to facilitate securing the graft material in the desired location in the site or pouch 3013.

According to some alternate embodiments, a system is provided that images the instrument or tool or instrument or tool tip at locations within the tissue of the patient to provide enhanced guidance. According to some embodiments of the invention, the system is configured to track the surgical tool, such as the tool used to develop the tunnel and surgical site (e.g., the pouch). The tool is represented on a display such as a monitor, and an image of the patient is generated and displayed, which, according to preferred embodiments, may be a tomographic image of the patient (that includes the surgical site), which preferably, has been obtained previously (e.g., at a prior visit). Alternatively, images such as, for example, MRI, stereotactic, and x-ray may be utilized to provide a patient image. Embodiments may display the tomographic image or may process and manipulate the image to another form that contains the represented imaged contours of that patient, and preferably at the desired location where the procedure is to be performed. According to some embodiments, the subperiosteal jaw reconstruction may be carried out by viewing a representation of the surgical tool or instrument, for example, the tool tip, on the image display screen. The tool location is provided on the screen to represent its location in the patient's mouth, which is the jaw area, and, more particularly, in the tissue where the procedure will be carried out. The instrument tip is illustrated and is viewed as it entered the subperiosteal tissue at a remote location from the surgical site. The imaging also provides for the viewing of the tool (tool tip) where the tool tip enters the subperiosteal tissue and is no longer visible to the surgeon who is maneuvering the tool. The system tracks the position of the tool, and preferably also identifies the tool depth, and its location in regard to the patient's physiology.

The method may be carried out by registering the presurgical image with the patient's mouth, and in particular the surgical site. Registration, according to some implementations, is carried out to estimate a transformation or coordinate mapping between two different coordinate systems. The surgical tool (or tool portion, such as the tip) may be viewed within parameters that permit maneuvering of the tool to create and develop the surgical site at the desired location in the patient's jaw where the procedure is to be carried out. According to some implementations, the image displayed provides the tool tracking, and the tool may be represented with a graphic representation. In the instance where the surgical site is also presented for display on the image, a target for the tool may be displayed, and when the tool is determined to be within the appropriate range (for example, when it is in the patient's tissue), the target, such as cross-hairs, or a bullseye are confirmed on the image displayed. According to one implementation, the registration takes place using an alignment element that is provided on the patient, and which may be tracked during the procedure. According to some implementations, the tool is tracked by providing the tool with a trackable element, such as a tool alignment element. The tools orientation and location may be monitored so that movement of the tool is recorded. Preferably, the tool movements are recorded, and a trackable target, such as an alignment element positioned relative to the patient, also is recorded. Relative tool movement may be determined, and represented on the screen image. In some implementations, the surgical tools are provided with an alignment element, which reduces the need for time involved in attaching an element to the tool. According to alternate embodiments, the tool may be fitted with an attachment that includes an alignment element. The surgical tool may be tracked in real-time by processing the real-time movements of the tool. Real-time processing of the surgical tool (or tool tip) location/orientation information which is dynamically integrated with the display image (e.g., of the patient's prior CT, MRI, stereotactic, or x-ray scan), provides the position of the tool or tool tip on the image. The tool location, while it is in the patient's mouth and within the tissue of the patient, as a representation in real-time on the display screen in conjunction with the previously obtained patient image.

According to some embodiments, the image information may be determined using a pixel coordinate system that provides a set of spatial coordinates for the patient image, and a set of spatial coordinates for the tool location. The stored patient image may have pixel coordinate locations (x,y) or (x,y,z), and the tool location may provide location coordinates (x,y) or (x,y,z), that are identified to correspond with the image pixel coordinates, based on the relative adjustment between the patient and tool (which may include a transformation as a result of the tool/patient registration, which may be done using the alignment elements). The pixels may be provided to be tagged for a region along a border or within the determined virtual procedure location, and in particular the surgical site (e.g., the incision, tunnel and pouch location). The system may be configured with software that processes the tool location and compares the tool location so that when the tool is within a designated region, such as a surgical site border or predetermined space within the tissue or mouth, then the image will provide a corresponding indication representation on the display screen on the patient image. The pixel coordinates forming the image, may be overridden or combined with the tool pixels or the representation while the tool is in that location. This provides the user/surgeon to guide the tool and make the appropriate manipulation or maneuvering (e.g., cutting, tunneling, placement of a graft, and/or depositing of implantable material) at the desired location. The pixel images of the patient scan image preferably are stored, and a virtual procedure may be overlaid to provide pixel images that appear for display with the patient image. According to some embodiments, the pixels are combined so that the image overlay of the procedural markings may permit viewing of the underlying image portions (including in the pixel coordinate location where the procedure marking is placed).

According to some implementations, the system includes a guide which is positioned on the patient. Some examples of the guide include a device that is worn or attached to the outside of the patient's head, or a device that is attached to the jawbone (outside of the patient's mouth) and also worn. The guide devices may have sensors that relate to the tool itself, or to other sensors or sensing elements provided on the tool. The guide facilitates tracking of the tool by correlating the patient with the image taken of the patient. According to some other embodiments, a guide is provided and comprises one or more elements that may be temporarily installed on the patient. For example, an element may be removably placed on one or more of the patient's teeth to provide a reference point when the patient's jaw (surgical site area) is imaged. The element is used to align the patient's mouth with the image that the system will display and on which the tool representation will be generated and displayed. In addition, the element may be used to provide a reference for other components that are used to provide location determination and tracking of the surgical tool. For example, according to some embodiments, the surgical procedure may be carried out where an alignment element temporarily attached to a patient (e.g., a patient's tooth or teeth), may be connected to an imaging reference (which for example, may be a pattern), that is detected by a detection component, such as a camera. The tool may also include an imaging reference. The patient alignment reference and the tool alignment reference preferably are used to identify the respective locations of the patient and tool. For example, in embodiments where the image scan already has been obtained with the patient reference (the element installed on the patient, e.g., on the patient's tooth), may be aligned with the patient element (now reinstalled on the position), and the relative positioning of the tool, which is the actual tool location is monitored and tracked. As the tool moves, the tool representation on the image display also correspondingly moves. The tool may be used to develop a tunnel in the mucosa and to produce a subperiosteal pouch at the desired surgical site location within the tissue of the patient. The tool may be monitored on the image display screen and the system is configured to process the information from the tool movement and the patient location, as determined by the alignment mechanisms and/or sensors employed. The system also may include markings which an operator, such as the physician using the tool, may provide on the image displayed to represent a proposed virtual procedure, identifying the location or locations for the remote incision, the subperiosteal tunnel and pouch. The surgical site may be pre-defined, as well as the implantable articles that will be used (e.g., a shaped bone graft block and bone particles). The surgeon, in this example, may determine a procedure to be carried out, position graphics on the display and on the patient image to represent the location where the remote incision is to be made, as well as to define the tunnel path, and the location, depth and volume of the pouch where the implantable materials will be placed. The system is designed to record and store the procedure markings of the virtual procedure which may be manipulated and saved. In this manner, the system may also offer or make available proposed graft shapes and sizes. This may be done by providing a graft block toolbox which may appear on the display screen with the image. For example, grafts represented in the toolbox may be dragged and positioned on the screen image at the virtual surgical site. The grafts may be maneuvered and positioned, tried and replaced in the virtual environment on the image displayed until a desired treatment option has been determined. The system may be configured to process the virtual procedure inputs and undertake a determination of the pouch size and dimensions (including the dimensional depth) and determine the pouch size. The system may provide proposed implantable articles, including shapes and sizes, based on the surgical site dimensions determined via the virtual procedure. The system may save the selections and recall them upon implementation of the treatment procedure when the actual procedure is carried out, or at any time prior to that, should the virtual procedure and treatment selection need to be reviewed. According to some preferred embodiments, the system may provide one or more proposals for treatment. For example, an incision, tunnel and surgical site pouch may be developed on the image by a user (e.g., a surgeon who will perform the procedure). The system processes the user designated proposal for the surgical incisions and area. The system makes proposals which utilize as part of the proposal an implantable article. The implantable article preferably comprises one or more of a shaped graft block or blocks, and bone particles (which preferably are provided in an injectable form, e.g., with a carrier or substrate such as a growth factor or other substance). For example, in the jaw restoration procedure, the shaped graft is designed to be positioned in the pouch by inserting it through an entry incision, such as a remote incision, and maneuvering it into position at the surgical site in the pouch. Preferably, the shaped graft is maneuvered through the tunnel that is developed between the remote incision and the pouch. The system may provide a shaped graft for use with the pouch designed.

According to preferred embodiments, the system also may be configured to dispense and control the implantable article. This may be provided as part of the above described system or may be separately provided (and may be linked to communicate with one or more other components such as for example the virtual planning and/or guidance system). For example, where the implantable article comprises bone particles (or synthetic bone) in an injectable form, which, typically, will be placed around the shaped graft block, the system may identify the volume of implantable article material required. According to some embodiments, the system includes a control mechanism, which for example, may include a processor, and software configured with instructions for determining the volumes for the surgical site or pouch and the implantable article (such as the shaped graft block and bone particles). The system may determine residual volume after selections of one or more graft blocks have been selected and positioned in place within the virtual procedure. In addition, the system also may perform volume determinations during the actual procedure, so that once the graft block is positioned within the pouch, the remaining volume to be taken up by bone particles/agent composition, is determined. According to some embodiments, a passageway is provided to admit the bone particles (and substrate) to the surgical site. For example, a tool comprising a lumen may be provided. A supply, such as, a reservoir, may be provided to hold the bone particles (and agents) for delivery to the surgical site. The system may control a propulsion mechanism, such as, a pump (e.g., a peristaltic pump), which is connected to deliver the bone particles through the lumen. The flow rate, volume, and total amount (total volume) may be controlled by the system. The user may regulate the flow (on/off, flow rate—fast to slow over a controllable range), and, as the graft particles (or material) are delivered to the site, the system determines the remaining volume and the remaining amount of material to be delivered. This dynamic volume determination is repeated during the delivery of the particles (or bone graft material) to continuously track the particle (or material) amounts (so that as the volume is being delivered, the remaining volume is decreasing). The system may provide an indicator of the volume on the display screen, including one or more graphic icons to show one or more of a level of volume, a level delivered and a level remaining to be delivered. In addition, or alternatively, audible sounds, lights/diodes or other indicators, may be provided in connection with the volume, flow rate, or other operations of the system to provide indications when reaching thresholds, identifying a correlating or non-correlating position (e.g., for the tool location in the patient's mouth). Alternately, or in addition thereto, a volume indicator may be provided on the tool or tool holder for ease of reference.

The graft particulate material preferably may be bone particles which may be mixed with or delivered with one or more other compounds, such as, for example, growth factors, collagen, binders, fillers, adhesives or other substances. An implantable article according to some preferred embodiments comprises bone that may be implanted into the jaw of an individual, and preferably below the periosteum. According to embodiments, the implantable article may comprise a bone graft block that has a particular shape that is desired for placement in the surgical site (or pouch formed in the periosteum at the site). The implantable article may include a bone graft block and also may include bone particles. The implantable article may be delivered at the surgical site, and may be carried out by delivering the bone graft block and bone particles separately from each other, or together, where an instrument positions the bone graft block and may also introduce bone particles (which may be a mixture with an agent such as a growth factor). For example, surgical instruments provided by the invention, according to some embodiments, may be used to position and shape the bone graft block within the pouch at the surgical site, and other instruments may be used to deliver the particulate bone implant to the site.

The system may include software programmed with instructions for determining a site volume and volume for delivery of implantable articles, such as, a graft block (which may have a preferred shape) and bone particulate material. For example, the surgical site has a surgical site volume ($V_s$) for receiving graft material. The implantable article to be installed at the surgical site location is designed to include a graft block having a graft shape and also includes particulate graft material. The implantable article comprises a graft shape comprising a graft block and particulate graft material. The software preferably is configured with instructions for determining the surgical site volume ($V_s$) for receiving graft material. The graft shape has a graft shape volume ($V_{gs}$). The site volume ($V_s$) less the graft shape volume ($V_{gs}$) provides the remaining volume of graft material ($V_{gr}$) to complete the graft at the surgical site. Formula (1) below illustrates the relationship.

$$Vs - Vgs = Vgr \qquad (1)$$

The software is configured with instructions for determining the site volume (Vs) and the graft shape volume (Vgs) of a graft block or blocks selected and is configured with instructions to dynamically track the volume of graft material delivered from the delivery apparatus to the surgical site. The software also regulates the delivery of the implantable bone particles (including the substrate carrying them or mixed therewith) to the surgical site via an article delivery source (such as, for example, a pump) by deducting the delivered volume (Vd) from the remaining volume of graft material (Vgr). The implantable article is installed at the surgical site by delivering the selected graft shape block of volume (Vgs) to the surgical site of volume (Vs) and delivering from said delivery apparatus a volume of graft material. Formula (2) below expresses this relationship.

$$Vgr - Vd = Vtbd \qquad (2)$$

According to a preferred embodiment, the system includes a processor and software as components of a computer, and has a frame on which the system components may be mounted or connected. The system may be linked to access information, and plans for a procedure may be configured by the user (a surgeon) remotely from the system. For example, the plan may be configured by access to the system from a remote link (Internet, VPN or the like), or alternatively, the plan may be generated apart from the system by the surgeon/user (e.g., on a tablet or laptop) and uploaded to the system.

According to some embodiments, the tools may also include indicia, such as sensing elements provided thereon, which provide identification of the specific tool type (e.g., routing or tunneling instruments, elevators and condensers, injectors, lumens, cameras, etc.). The tool therefore may be represented on the screen, and an indication of the tool type provided. In addition, in accordance with a virtual procedure plan, the system may identify particular tools for use at particular stages of the procedure (e.g., a tunneling tool for developing the tunnel), and call for a tool to be utilized. If that tool is not being used (tool type, tool size, etc.), based on the sensed tool information, the system may be programmed to react and provide a response by ceasing further movement (in the case of a tool with motility), alerting the user (surgeon). This feature may be overridden, selected or deselected.

According to some embodiments, the system has a sensing component which is provided to sense the movement of any alignment elements, including, for example, an alignment element provided on the patient (on the patient's body, tooth or an extension therefrom), provided on the tool, and at a fixed location relative to the fixed sensing component. For example, the sensing component may comprise a camera that records images of the alignment elements and provides that information to the system. The system is configured to process the imaged information, and preferably does so dynamically with the information from the alignment elements continually being monitored by the camera (at a high frame rate) and processed to provide information, which may be shown graphically on the display screen image, representing the tool position, as well as other attributes of the procedure and/or measurable components. Although this is one implementation, other implementations to represent the tool and its movement during the procedure may be carried out.

According to another embodiment, the element that is temporarily attached to the patient may be connected with, or configured to include sensing circuitry or components that may include a GPS, accelerometer, combinations thereof, as well as other tools for providing a reference. The reference data is monitored by the system, as described by providing GPS location information. The location information may be sensed for the tool, patient and/or a reference aligner. Alternative embodiments provide discrete GPS sensors on the tool and on the patient or a device tracking the relative movement of the patient. The GPS sensing may be done with circuitry and provide real-time location information for the tool and patient. For example, the GPS location sensors may be provided at a distal location from the tool tip (the tool tip comprising the cutting or forming end of the tool), and the sensing information may be attenuated by a translational component to provide the location of the tip. In addition to GPS components a gyro, which may be configured on a chip or microcircuitry, so orientation and position of the tool may be determined and represented (e.g., on the display) as the tool is maneuvered within the patient's periosteum. Other embodiments of the tool may include a display on the tool, so that the visual indication of the tool relative to the patient surgical site location, a bullseye or target is also displayed. The tool display may be removably detachable (and may clip to a nearby structure or individual (e.g., garment, sleeve, etc.).

Graft blocks may be produced, as needed, based on the procedure plan developed by the user (e.g., surgeon) who prepares a virtual plan. In some instances, the system may provide the graft requirements to a lab that constructs the graft needed based on the procedure directives selected by the user. The system also may provide a service that involves producing one or more implantable articles for use in a jaw reconstruction procedure. The user may subscribe to the service and may be required to have a subscription for each patient (e.g., a patient account).

Figure 36:
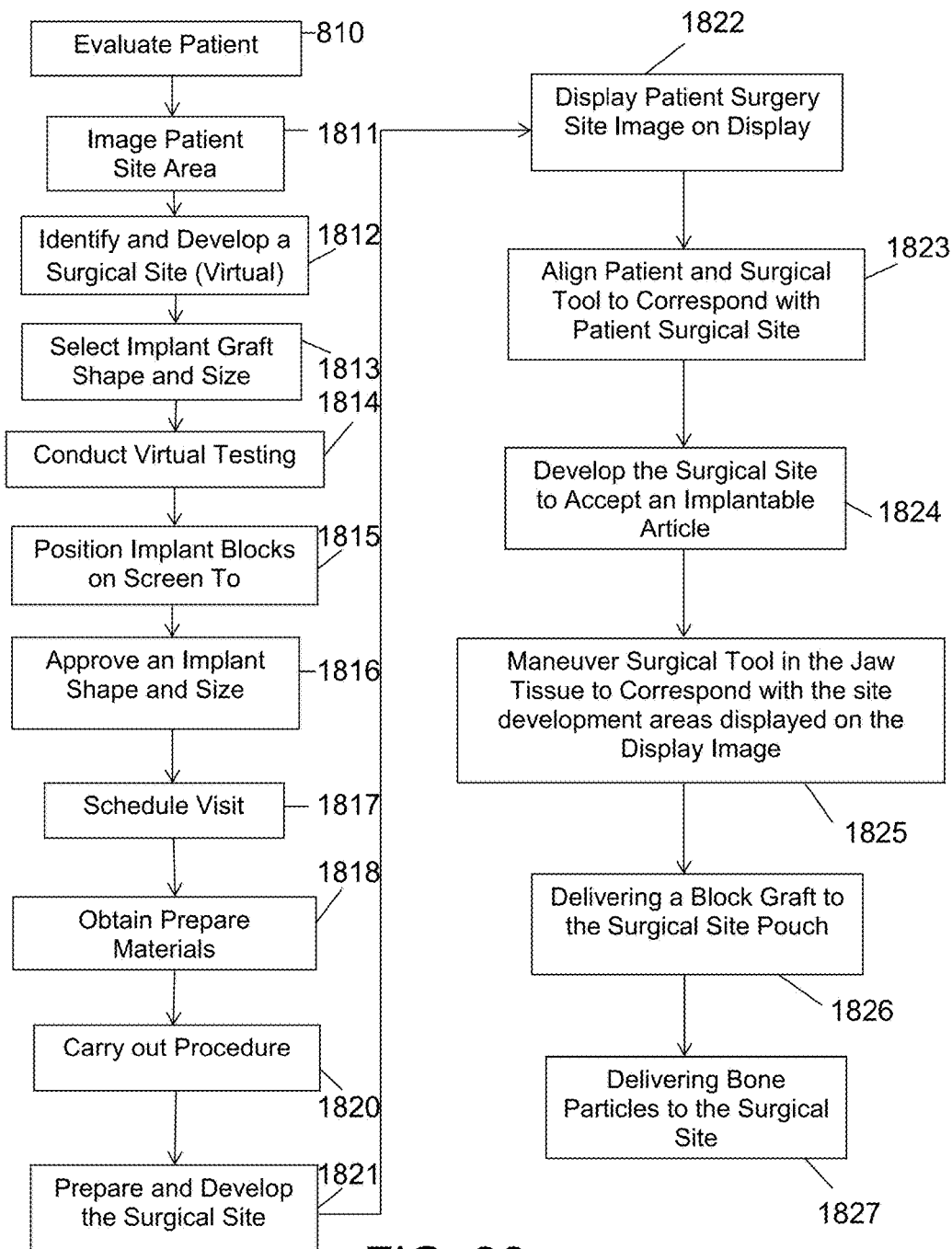
FIG. 36 is a flow diagram of an exemplary implementation of method steps that may be carried out in accordance with embodiments of the invention to reconstruct the jaw of an individual.

Referring to FIG. 36, a schematic illustration of a flow diagram of the system and method for conducting a subperiosteal jaw reconstruction procedure is carried out in accordance with an exemplary implementation of method. The method illustrated is carried out in conjunction with a display screen that depicts the patient surgical site via a previously obtained image of the patient (e.g., CT scan). In the exemplary depiction, the method commences with a patient evaluation, block 1810, which preferably is done by medical personnel, and preferably a surgeon, and more preferably the surgeon that will perform the procedure. The patient operating site will be designated and imaged, block 1811. The surgeon therefore may load the patient image on the system, and the system presents the image on a display. The surgeon then identifies and develops a surgical site on the image or with reference thereto, block 1812. The surgeon user in this example, then uses the on screen tools, which may be selected and moved in accordance with an input device, such as a mouse, stylus, touch screen, and the like, to design a proposed treatment procedure that comprises an identification of the location and the size and shape of a tunnel and pouch that are to receive an implant. The surgeon then selects the shape and size of a suitable graft block for the surgical site, block 1813. This may be done by dragging a virtual graft displayed on the display screen to test fit the graft within the pouch space, tunnel, and other surgical designs that the surgeon has developed in reference to the displayed image and virtual procedure (e.g., block 1812). In this example, the surgeon conducts virtual testing of the graft block to determine whether it is suitable for the procedure and the site location, block 1814. This may be done by positioning a block of a particular shape in the pouch location, and within the tunnel to determine suitability, block 1815. The system tools also may provide different sizes of graft blocks to try, or, according to some embodiments, the surgeon may manipulate the block size with a tool to fit the graft shape into one or more spaces. Once the desired graft shape and size has been determined, and approved by the surgeon, the system is prompted to save the desired setting, block 1816, and the implantable article shape and size is stored. The system may generate an order for processing of the block, and may send the order to a suitable location (a remote lab) for construction of the graft. Other embodiments of the system are linked with a lab to provide the information and upload the graft required to the system laboratory. The system laboratory may include an interface for placing an order which may be done as part of the software used to process and display the virtual procedure information. Users, such as surgeons, also may subscribe to a service that designs the implantable article. For example, the system may provide a design service that processes the patient information, and returns a virtual treatment designed for that patient, with proposed site and site development, and proposed graft blocks. The surgeon may evaluate the proposed procedure and accept it, and generate an order for the implantable article to be produced and provided.

Once the procedure and articles are determined, the patient visit is scheduled, block 1817, preferably at a time suitable for the graft materials to be prepared and provided to the surgeon. The surgeon obtains the material and prepares them for implanting into the jaw of the patient, block 1818. Some material preparation, according to some embodiments, may be done at the time of the procedure, where one or more substances is added or mixed together. The procedure is carried out on the patient to provide a jaw restoration, block 1820. In the procedure, the surgeon prepares and develops the surgical site for the implantable material, block 1821. The patient site image is brought up on the display, block 1822. In embodiments where the system is utilized to provide imaging of the patient and tools, including the tool potion during the procedure, the optional step of aligning the patient and surgical tool to correspond with the surgical site is implemented, block 1823. The surgical site is developed to accept an implantable article, block 1824. One or more tools are maneuvered to develop the surgical site (e.g., an incision, tunnel and pouch). In embodiments where the system tracks tool movement and positioning, the tool (or tools) is maneuvered to correspond with the image displayed and the virtual plan for the procedure that also appears with the displayed image, block 1825. The tools are maneuvered in accordance with the identified development areas appearing on the image display. Once the site is developed, the graft block is delivered to the surgical site, block 1826. Additional bone material, such as bone particles with a substrate carrier, are delivered to the surgical site, block 1827. The procedure is completed by closing the entry incision, or other procedure to promote healing of the wound and site.

The method disclosed and illustrated may be implemented to provide restoration of degenerated gingival papillae which have receded. For example, interdental recession typically is a result of the loss of the interdental papilla. The loss of this papilla typically diminishes the interproximal attachment with a tooth surface, a dental implant surface, or between adjacent teeth or implants. According to some preferred embodiments, the method may be implemented to regenerate the papillary loss, and provide restorative functions not only to the jaw bone, but also to adjacent teeth. In addition to the jaw bone and papillae improvements, the soft tissue also may be restored to improve the health and aesthetics.

Features discussed and shown herein in conjunction with one or more embodiments of the method, implantable articles, and instrumentation, may be combined with one or more features and implemented together in an article, instrument, or method. While the method and devices of the invention have been disclosed in detail, and the preferred embodiments and best mode for practice of the invention have been similarly disclosed, the scope of exclusive rights to which the invention is entitled is defined by the claims appended hereto and by equivalents that perform substantially the same function in substantially the same way to achieve the same result.

What is claimed is:
1. A method for reconstruction of a jaw comprising:
   a) selecting a surgical site at which implantable bone material is to be installed;
   b) making at least one incision at a location in a tissue of an individual that is remote from said surgical site;
   c) developing a subperiosteal tunnel from the remote incision leading to the surgical site by detaching the periosteum from the bone surface;
   d) forming a pouch below the periosteum at the surgical site for receiving the implantable bone material;
   e) delivering the implantable bone material at the surgical site by passing the implantable bone material through the remote incision and through the tunnel; and
   f) maneuvering the implantable bone material at the surgical site to position the implantable bone material in a desired condition within the pouch between the patient bone and the periosteum;
   g) wherein, when implanting the implantable bone material at the surgical site between the patient bone and the periosteum, the implantable bone material is implanted to directly contact the bone without a membrane therebetween.

2. The method of claim 1, including condensing the implantable bone material at the surgical site.

3. The method of claim 1, wherein forming the pouch comprises detaching and elevating the periosteum from the bone surface at the surgical site.

4. The method of claim 1, wherein said implantable bone material comprises particulate bone graft, bone graft molded with a binding agent, or bone/collagen composite graft.

5. The method of claim 4, wherein said implantable bone material comprises a xenograft, allograft, autograft or mineral graft used individually or in combination with each other.

6. The method of claim 5, wherein said implantable bone material comprises human bone particles or a xenograft formed from bovine, equine or porcine anorganic bone particles and a binder, adhesive or biologic agent.

7. The method of claim 6, wherein said implantable article comprises human bone particles or a xenograft formed from anorganic bovine, equine or porcine bone particles that are mixed with a biologic agent containing growth factors.

8. The method of claim 7, including generating an image of the jaw; identifying the surgical site at which the implant is to be installed, and producing a bone graft configured based on the image generated and the surgical site.

9. The method of claim 8, wherein said bone graft is formed by 3D printing anorganic bone particles.

10. The method of claim 1, including providing a periosteal elevator having a tip with a sharp cutting edge and being maneuverable to cut through and separate the periosteum from the bone surface with said tip.

11. The method of claim 10, including developing said subperiosteal tunnel with said periosteal elevator.

12. The method of claim 11, wherein forming the subperiosteal pouch includes maneuvering said elevator below the periosteum to form said pouch, and wherein at least a portion of said periosteal elevator comprises a shank that is configured to fit within the tunnel when the elevator is maneuvered to form the pouch.

13. The method of claim 12, wherein said implantable bone material comprises an article that is maneuvered from the incision to the pouch at the surgical site with a holder that releasably grasps the implantable article.

14. The method of claim 12, including condensing the implantable bone material at the surgical site, wherein said implantable bone material is condensed at the surgical site with a condenser that shapes the implantable bone material.

15. The method of claim 1,
wherein the subperiosteal tunnel is less than 6 mm in width.

16. The method of claim 1, wherein said surgical site comprises a location where at least one tooth is damaged or missing, and wherein said remote incision is made a distance from said surgical site which is a distance between the location of an adjacent tooth and a location before the location where the at least one tooth is damaged or missing.

17. The method of claim 1, including closing said remote incision.

18. The method of claim 16, wherein said remote incision comprises the entry point for accessing said tunnel and said pouch.

19. The method of claim 1, including closing the remote incision, wherein said bone material is enclosed within said pouch and wherein said incision closes off said tunnel and said pouch.

20. The method of claim 1, wherein said periosteum is in direct contact with said bone material at said surgical site and provides cells for bone regeneration at the surgical site.

21. The method of claim 1, wherein said pouch is defined by at least one first portion and at least one second portion, wherein said pouch is developed under the periosteum and includes exposed bone bordering the first portion of said pouch, and the periosteum defining the second portion of the pouch.

22. The method of claim 1, wherein said pouch is defined by at least one first portion and at least one second portion, wherein said pouch is developed under the periosteum and includes an exposed implant or portion thereof bordering the first portion of said pouch, and the periosteum defining a second portion of the pouch.

23. The method of claim 1, wherein said pouch is defined by at least one first portion and at least one second portion, wherein said pouch is developed under the periosteum and includes an exposed portion of a tooth bordering the first portion of said pouch, and the periosteum defining a second portion of the pouch.

24. The method of claim 1, wherein the subperiosteal tunnel is narrower than the pouch.

25. The method of claim 1,
wherein the pouch has a first portion comprising exposed bone on one side thereof and a second portion comprising the periosteum on the other side thereof, wherein said implantable bone material is placed between both said pouch portions in a manner that distends said second portion horizontally, vertically, or in both directions.

26. The method of claim 1,
wherein the pouch has a first portion that includes an exposed implant or portion thereof on one side, and a second portion comprising the periosteum on the other side thereof, wherein said implantable bone material is placed between both said pouch portions in a manner that distends said second portion horizontally, vertically, or in both directions, over the exposed portion of the implant.

27. The method of claim 1,
wherein the pouch has a first portion that includes an exposed portion of a tooth on one side, and a second portion comprising the periosteum on the other side thereof, wherein said implantable bone material is placed between both said pouch portions in a manner that distends said second portion horizontally, vertically or in both directions, over the exposed portion of the tooth.

* * * * *